(12) United States Patent
Hackett et al.

(10) Patent No.: US 6,489,458 B2
(45) Date of Patent: *Dec. 3, 2002

(54) DNA-BASED TRANSPOSON SYSTEM FOR THE INTRODUCTION OF NUCLEIC ACID INTO DNA OF A CELL

(75) Inventors: Perry B. Hackett, Shoreview, MN (US); Zoltan Ivics, Amsterdam (NL); Zsuzsanna Izsvak, Amsterdam (NL)

(73) Assignee: Regents of the University of Minnesota, Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/142,593

(22) PCT Filed: Mar. 11, 1998

(86) PCT No.: PCT/US98/04687

§ 371 (c)(1),
(2), (4) Date: Sep. 10, 1998

(87) PCT Pub. No.: WO98/40510

PCT Pub. Date: Sep. 17, 1998

(65) Prior Publication Data

US 2002/0016975 A1 Feb. 7, 2002

Related U.S. Application Data

(60) Provisional application No. 60/040,664, filed on Mar. 11, 1997, provisional application No. 60/053,868, filed on Jul. 28, 1997, and provisional application No. 60/065,303, filed on Nov. 13, 1997.

(51) Int. Cl.[7] .................... C07H 21/02; C07H 21/04; C07K 1/00; C12N 5/00; C12N 15/00
(52) U.S. Cl. ............. 536/23.2; 536/23.1; 536/23.5; 530/350; 435/325; 435/440; 435/445
(58) Field of Search ............... 536/23.1, 23.5; 530/350; 435/325, 320.1, 440, 455; 514/44

(56) References Cited

U.S. PATENT DOCUMENTS

| | | |
|---|---|---|
| 4,631,259 A | 12/1986 | Clewell et al. |
| 5,464,758 A | 11/1995 | Gossen et al. |
| 5,677,170 A | 10/1997 | Devine et al. |
| 5,814,618 A | 9/1998 | Bujard et al. |
| 5,879,933 A | 3/1999 | Hodgson |
| 6,013,240 A | 1/2000 | Behr et al. |
| 6,051,430 A | 4/2000 | Plasterk et al. |

FOREIGN PATENT DOCUMENTS

| | | |
|---|---|---|
| EP | 0 485 701 A1 | 5/1992 |
| EP | 0 756 007 A2 | 1/1997 |
| WO | WO 88/01646 | 3/1988 |
| WO | WO 95/01095 | 1/1995 |
| WO | WO 96/01313 | 1/1996 |
| WO | WO 96/40892 | 12/1996 |
| WO | WO 97/15679 | 5/1997 |
| WO | WO 97/29202 | 8/1997 |
| WO | WO 98/24479 | 6/1998 |
| WO | WO 98/56903 | 12/1998 |
| WO | WO 99/25817 A2 | 5/1999 |
| WO | WO 00/30687 A1 | 6/2000 |
| WO | WO 01/30965 A2 | 5/2001 |
| WO | WO 01/81565 A2 | 11/2001 |

OTHER PUBLICATIONS

Amsterdam et al., "The *Aequorea victoria* green fluorescent protein can be used as a reporter in live zebrafish embroyos," *Dev. Biol.*, 171(1):123–9 (1995).

Bandyopadhayay et al., "Enhanced gene transfer into HuH–7 cells and primary rat hepatocytes using targeted liposomes and polyethylenimine," *Biotechniques*. 25(2):282–92 (Aug., 1998).

Bandyopadhyay et al., "Nucleotide exchange in genomic DNA of rat hepatocytes using RNA/DNA oligonucleotides. Targeted delivery of liposomes and polyethyleneimine to the asialoglycoprotein receptor," *J Biol Chem.*, 274(15):10163–72 (1999).

Blazar et al., "In utero transfer of adult bone marrow cells into recipients with severe combined immunodeficiency disorder yields lymphoid progeny with T–and B–cell functional capabilities," *Blood*, 86(11):4353–66 (1995).

Boussif et al., "A versatile vector for gene and oligonucleotide transfer into cells in culture and in vivo: polyethylenimine," *Proc. Natl. Acad. Sci. USA*, 92(16):7297–301 (1995).

Chowdhury et al., "Gunn rat: a model for inherited efficiency of bilirubin glucuronidation," *Adv. Vet. Sci. Comp. Med.*, 37:149–73 (1993).

Clark et al., "Development of Dicistronic Vectors for Analysis of Transgene Expression in Zebrafish," Abstract presented at the 1998 meeting of "Zebrafish Development and Genetics," Cold Spring Harbor Laboratory, Cold Spring Harbor, NY (Apr. 29–May 3, 1998).

Dubois et al., "Colorimetric Method for Determination of Sugars and related substances," *Anal. Chem.* 28(3), 350–6 (1956).

Dupuy et al., "Adapting the Sleeping Beauty Transposon for Insertional Mutagenesis in the Mouse," Abstract presented at the 1998 meeting on "Mouse Molecular Genetics," Cold Spring Harbor Laboratory, Cold Spring Harbor, NY (Sep. 2–Sep. 6, 1998).

(List continued on next page.)

*Primary Examiner*—Deborah Crouch
*Assistant Examiner*—Joseph Woitach
(74) *Attorney, Agent, or Firm*—Mueting, Raasch & Gebhardt, P.A.

(57) ABSTRACT

This invention relates to a system for introducing nucleic acid into the DNA of a cell. The system includes the use of a member of the SB family of transposases (SB) or nucleic acid encoding the transposase and a nucleic acid fragment that includes a nucleic acid sequence with flanking inverted repeats. The transposase recognizes at least a portion of an inverted repeats and incorporates the nucleic acid sequence into the DNA. Methods for use of this system are discussed.

64 Claims, 13 Drawing Sheets

OTHER PUBLICATIONS

Economy Polymers and Chemicals, "Economy Products—Polyethyleneimine," product literature [online]; Houston, TX; [retrieved on 2001–05–10]; Retrieved from the Internet: URL:<http://www.economypolymers.com/polethyl.htm>; 2 pages.

Erbacher et al., "Transfection and physical properties of various saccharide, poly(ethylene glycol), and antibody-derivatized polyethylenimines (PEI)," *J. Gene Med.*, 1(3):210–22 (1999).

Fletcher et al., "Mariner transposon mediated stable integration of adenoviral sequences for use as gene thereapy vector system," Abstract 608, American Association of Hematology, Dec., 1998; in Miami, FL.

Gray, "The direct coupling of oligosaccharides to proteins and derivatized gels," *Arch. Biochem. Biophys.*, 163(1):426–8 (1974).

Hackett et al., "Sleeping Beauty Transposon For Gene Therapy," Grant Abstract, Grant No. 2P01HD032652–060006 [online]. National Institute of Child Health and Human Development, National Institutes of Health, project dates Jan. 10, 1995–Dec. 31, 2002 [retrieved on Jun. 19, 2001]. Retrieved from the Internet: URL: http://commons.cit.nih.gov/crisp3/crisp_lib.getdoc?textkey=6325542&p_grant_n um=2P01HD032652–060006&p_query=&ticket=1664&p_audit_session_id=38 1420&p_keywords=, 2 pages.

Hackett et al., "Zebrafish as a Model System For Biomedical Research," Grant Abstract, Grant No. 5R01RR006625–06 [online]. National Center for Research Resources, National Institutes of Health, project dates Aug. 1, 1991–Aug. 31, 2000 [retrieved on Jun. 19, 2001]. Retrieved from the Internet: URL: http://commons.cit.nih.gov/crisp3/crisp_lib-.getdoc?textkey=2772010&p_grant_n um=5R01RR006625–06&p_query=&ticket=1664&p_audit_session_id=381420 &p_keywords=, 2 pages.

Kircheis et al., "Coupling of cell–binding ligands to polyethylenimine for targeted gene delivery," *Gene Ther.*, 4(5):409–18 (1997).

Klotz et al., "Macromolecule–small molecule interactions. Strong binding and cooperativity in a model synthetic polymer," *Biochemistry*, 8(12):4752–6 (1969).

Kren et al., "Alterations in mRNA stability during rat liver regeneration," *Am. J. Physiol.*, 270(5 Pt 1):G763–77 (May, 1996).

Kren et al., "Correction of the UDP–glucuronosyltransferase gene defect in the Gunn rat model of Crigler–Najjar Syndrome type I with a chimeric oligonucleotide," *Proc. Natl. Acad. Sci. USA.* 96(18):10349–54 (1999).

Li et al., "Inversion and transposition of Tc1 transposon of *C. elegans* in mammalian cells," *Somat. Cell Mol. Genet.*, 24(6):363–369 (Nov. 1998).

Linehan–Stieers et al., "Uniform distribution and long–term expression of GFP in liver mediated by the Sleeping Beauty transposon system," abstract presented at Fourth Annual Meeting of the American Society of Gene Therapy, Seattle, Washington, May 30–Jun. 3, 2001 (1 page).

Lönngren et al., "Aldonate coupling, a simple procedure for the preparation of carbohydrate–protein conjugates for studies of carbohydrate–binding proteins," *Arch. Biochem. Biophys.*, 175(2):661–9 (1976).

Marshall, E., "Gene Therapy on Trial," *Science*, 288, 951–957 (2000).

Meng et al., "Promoter analysis in living zebrafish embryos identifies a cis–acting motif required for neuronal expression of GATA–2," *Proc. Natl. Acad. Sci. USA.*, 94(12):6267–72 (1997).

Mohn et al., "Transposon–Mediated Transgenesis allows stable expression following germ–line transmission," Abstract presented at the 1998 meeting on Zebrafish Development & Genetics, Cold Spring Harbor Laboratory, Cold Spring Harbor, NY (Apr. 29–May 3, 1998).

Monsigney et al., Colorimetric determination of neutral sugars by a resorcinol sulfuric acid micromethod, *Anal. Biochem.*, 175(2):525–30 (1988).

Morral et al., "Administration of helper–dependent adenoviral vectors and sequential delivery of different vector serotype for long–term liver–directed gene transfer in baboons," *Proc. Natl. Acad. Sci. USA.* 26;96(22):12816–21 (Oct. 1999).

National Institutes of Health, "Blast 2 Sequences," [online] Bethesda, MD [retrieved Apr. 9, 2002]. Retrieved from the Internet: <http:www.ncbi.nlm.nih.gov/gorf/bl2.html>; 1 page.

Snyder et al., "An improved 2,4,6–trinitrobenzenesulfonic acid method for the determination of amines," *Anal. Biochem.*, 64(1):284–8 (1975).

Suh et al., "Ionization of poly(ethylenimine) and poly(allylamine) at various pH's," *Bioorg. Chem.*, 22(3):318–327 (1994).

Trembley et al., "Differential regulation of cyclin B1 RNA and protein expression during hepatocyte growth in vivo," *Cell Growth Differ.*, 7(7):903–16 (1996).

Weinberg, Eric, S., "Zebrafish genetics: Harnessing horizontal gene transfer," *Current Biology*, 8, R244–R247 (1998).

Yant et al., "The development of new recombinant adenoviral vectors capable of stable integration into mammalian genomes," Abstract 922, p. 232a, 2nd Annual Meeting of the American Society of Gene Therapy, Jun. 9–13, 1999; in Washington, DC.

Yoon et al., "Targeted gene correction of episomal DNA in mammalian cells mediated by a chimeric RNA–DNA oligonucleotide." *Proc. Natl. Acad. Sci. USA.*, 93(5):2071–6 (1996).

Borman et al., "Comparison of picornaviral IRES–driven internal initiation of translation in cultured cells of different origins," *Nucleic Acids Res.*, 25, 925–932 (1997).

Borman et al., "Picornavirus internal ribosome entry segments: comparison of translation efficiency and the requirements for optimal internal initiation of translation in vitro," *Nucleic Acids Res.*, 23, 3656–3663 (1995).

Clarke et al., "pPV: a novel IRES–containing vector to facilitate plasmid immunization and antibody response characterization," *Immunotech.*, 3(2):145–153 (1997).

Cormack et al., "FACS–optimized mutants of the green fluorescent protein (GFP)," *Gene*, 173, 33–38 (1996).

Craig, "Target Site Selection in Transposition," *Annu. Rev. Biochem.*, 66, 437–474 (1997).

Cusick, "Jumpy Gene Brought Back to Life," *ScienceNOW*, 1 page (Nov. 19, 1997).

Fire et al., "A modular set of lacZ fusion vectors for studying gene expression in *Caenorhabditis elegans*," *Gene*, 93(2):189–198 (1990).

Ghattas et al., "The Encephalomyocarditis Virus Internal Ribosome Entry Site Allows Efficient Coexpression of Two Genes from a Recombinant Provirus in Cultured Cells and in Embryos," *Mol. Cell. Biol.*, 11, 5848–5859 (1991).

Gurtu et al., "IRES bicistronic expression vectors for efficient creation of stable mammalian cell lines," *Biochem. and Biophys. Res. Comm.*, 229(1):295–298 (1996).

Hackett et al., "Construction of a Transposon System Active in Human Cells," *Keystone Symposia on Molecular & Cellular Biology*, Abstract and Poster (Jan. 20, 1998).

Hackett et al., "Development of Genetic Tools for Transgenic Animals," in: Murray et al., *Transgenic Animals in Agriculture*, (CABI Publishing, New York, 1999), Chap. 2, pp. 19–35 (Presentation from a conference held in California in Aug. 1997).

Hallet et al., "Transposition and site–specific recombination: adapting DNA cut–and–paste mechanisms to a variety of genetic rearrangements," *FEMS Microbiology Reviews*, 21, 157–178 (1997).

Hellen et al., "Translation of Encephalomyocarditis Virus RNA by Internal Ribosomal Entry," *Curr. Top. Microbiol. Immunol.*, 203:31–63 (1995).

Ivics et al., "Genetic Applications of Transposons and Other Repetitive Elements in Zebrafish," *Meth. Cell Biol.*, 60, 99–131 (1999).

Izsvak et al., "Two–Stage Ligation–Mediated PCR Enhances the Detection of Integrated Transgenic DNA," *BioTechniques*, 15, 814,816, and 817 (1993).

Jang et al., "Cap independent translation of encephalomyocarditis virus RNA: structural elements of the internal ribosomal entry site and involvement of a cellular 57–κD RNA–binding protein," *Genes Dev.*, 4, 1560–1572 (1990).

Kaminski et al., "Translation of encephalomyocarditis virus RNA: parameters influencing the selection of the internal initiation site," *EMBO J*, 1673–1681 (1994).

Kaufman et al., "Improved vectors for stable expression of foreign genes in mammalian cells by use of the untranslated leader sequence from EMC virus," *Nucleic Acids Res.*, 19(16):4485–4490 (1991).

Liu et al., "Development of Expression Vectors for Transgenic Fish," *BioTechnol.*, 8, 1268–1272 (1990).

Liu et al., "Isolation and characterizationof β–actin gene of carp (*Cyprinus carpio,*)" *DNA Sequence–J. DNA Sequencing and Mapping*, 1, 125–136 (1990).

Lewin, *Genes VI*, "Eukaryotic mRNAs have a methylated cap at the 5' end," Oxford University Press, pp. 171–172 (1997).

Lewin, *Genes VI*, "Nuclear splicing proceeds through a lariat," Oxford University Press, pp. 891–893 (1997).

Mountford et al., "Internal ribosome entry sites and dicistronic RNAs in mammalian transgenesis," *Trends Genet.*, 11:179–184 (1995).

Padgett et al., "Splicing of Messenger RNA Precursors," *Ann. Rev. Biochem. J.*, 55, 1119–1150 (1988).

Pelletier et al., "Internal initiationof translation of eukaryotic mRNA derived from poliovirus RNA," *Nature*, 334, 320–325 (1988).

Petrov et al., "Diverse transposable elements are mobilized in hybrid dysgenesis in *Drosophila virus,*" *Proc. Natl. Acad. Sci. USA*, 92(17):8050–8054 (1995).

Raz et al., "Transposition of the nematode *Caenorhabditis elegans* Tc3 element in the zebrafish *Danio rerio,*" *Current Biology*, 8, 82–83, 85, 87–88 (Dec. 12, 1997).

Schouten et al., "Transposon Tc1 of the nematode *Caenorhabditis elegans* jumps in human cells," *Nucleic Acids Research*, 26(12):3013–3017 (1998).

Szekely et al., "P element mediated germ line transformation of *Drosophila melonogaster* with the Tc1 transposable DNA element from *Caenorhabditis elegans.*" *Genome*, 37(3):356–366 (1994).

Urabe et al., "A novel dicistronic AVV vector using a short IRES segment derived from hepatitis C virus genome," *Gene: An International Journal on Genes and Genomes*, 200(1–2):157–162 (1997).

von Melchner et al., "Identification of Cellular Promoters by Using a Retrovirus Promoter Trap," *J. Virol.*, 63, 3227–3233 (1989).

Weber et al., "An SV40 'Enhancer Trap' Incorporates Exogenous Enhancers or Generates Enhancers from Its Own Sequences," *Cell*, 36, 983–992 (1984).

Westerfield, *The Zebrafish Book*, University of Oregon Press, Eugene, OR (1995), Title Page & Table of Contents only; text is available at zfish.uoregon.edu/zf_infoo/zfbook/zfbk.html.

Youngman et al., "Rte–1, a retrotransposon–like element in *Caenorhabditis elegans,*" *FEBS Letter*, 380, 1–7 (1996).

Zambrowicz et al., "Disruption and sequence identification of 2,000 genes in mouse embryonic stem cells," *Nature*, 392, 608–611 (1998).

Clark, K.J., et al., "Development of Dicistronic Vectors for Analysis of Transgene Expression in Zebrafish," Abstracts presented at 1998 meeting on "Zebrafish Development & Genetics," Cold Spring Harbor Laboratory Press, Cold Spring Harbor, NY, p. 280 (Apr. 29–May 3, 1998).

Dupuy, A., et al., "Adapting the Sleeping Beauty Transposon for Insertional Mutagenesis in the Mouse," Abstract presented at the 1998 meeting on "Mouse Molecular Genetics," Cold Spring Harbor Laboratory, Cold Spring Harbor, NY, p. 95 (Sep. 2–Sep. 6, 1998).

Fahrenkrug, S.C., et al., "Dicistronic Gene Expression in Developing Zebrafish," *Mar. Biotechnol.*, 1, 552–561 (1999).

Hackett, P.B., et al., "Sleeping Beauty Transposon for Gene Therapy," Grant Abstract, Grant No. 2P01HD032652–060006 [online], National Institute of Child Health and Human Development, National Institutes of Health, project date Jan. 10, 1995–Dec. 31, 2002 [retrieved on Jun. 19, 2001]. Retrieved from the Internet: URL:<http://commons.cit.nih.gov/crisp3/crisp_lib.getdoc-?textkey=6325542&p_g rant_num= 2P01HD032652–060006&p_query=&ticket=47000&p_audit_session_i d=690753&p_keywords=>, 2 pages.

Hackett et al., "Zebrafish as a model system for biomedical research," Grant Abstract, Grant No. 5R01RR006625–06 [online], National Center for Research Resources, National Institutes of Health, project dates Aug. 1, 1991–Aug. 31, 2000 [retrieved on Jun. 19, 2001]. Retrieved from the Internet: URL:<http://commons.cit.nih.gov/crisp3/crisp_lib.getdoc?textkey=2772010&p_g rant_num= 5R01RR006625–06&p_query=&ticket=46992&p_audit_session_id=69 0675&p_keywords=>, 2 pages.

Izsvák, Z., et al., "Sleeping Beauty, a Wide Host–range Transposon Vector for Genetic Transformation in Vertebrates," *J. Mol. Biol.*, 302, 93–102 (2000).

Weinberg, E.S., "Zebrafish Genetics: Harnessing Horizontal Gene Transfer," *Current Biology*, 8, R244–R247 (1998).

Yant, S.R., et al., "Somatic Integration and Long–term Transgene Expression in Normal and Haemophilic Mice Using a DNA Transposon System," *Nature Genetics*, 25(1), 35–41 (May 2000).

Becker et al., "Chapter 8: Use of Recombinant Adenovirus for Metabolic Engineering of Mammalian Cells," *Methods in Cell Biology*, vol. 43: Protein Expression in Animal Cells, Roth, ed., Academic Press, New York, Title page, publication page, table of contents and pages 161–189 (1994).

Beckwith, "lac: The Genetic System," *The Operon*, second edition, Miller et al., eds., Cold Spring Harbor Laboratory Press, New York, Title page, publication page, table of contents, and pp. 11–30 (1980).

Bellon et al., "Aerosol Administration of a Recombinant Adenovirus Expressing CFTR to Cystic Fibrosis Patients: A Phase I Clinical Trial," *Human Gene Ther.*, 8(1):15–25 (1997).

"Bidirectional Tet Expression Vectors, Simultaneous control expression of two genes with one tet–responsive element," http://www.clontech.com/archive/OCT96UPD/pBIVectors.html, 3 pages (Available on or before Apr. 25, 2000).

Blast 2 Sequences, http://www.ncbi.nlm.nih.gov/gorf/bl2.html, 1 page (Available on or before May 11, 2000).

Burcin et al., "Adenovirus–mediated regulable target gene expression in vivo," *Proc. Nat'l. Acad. Sci. USA*, 96:355–360 (Jan. 19, 1999).

Carey, "On the Trial of the Jumping Genes," *Business Week*, 89 (Jun. 29, 1998).

Curcio et al., "Regulation of retrotransposition in *Saccharomyces cerevisiae*," *Mol. Microbiol.*, 5(8):1823–1829 (1991).

Essner et al., "Expression of Zebrafish connexin43.4 in the Notochord and Tail Bud of Wild–Type and Mutant no tail Embryos," *Developmental Biology*, 177:449–462 (1996).

Essner et al., "The zebrafish thyroid hormone recptor α1 is expressed during early embryogenesis and can function in transcriptional repression," *Differentiation*, 62:107–117 (1997).

Fadool et al., "Transposition of the mariner element from *Drosophila mauritiana* in zebrafish," *Proc. Nat'l. Acad. Sci. USA*, 95(9):5182–5186 (Apr. 1998).

Ferry et al., "Liver–Directed Gene Transfer Vectors," *Human Gene Ther.*, 9(14):1975–1981 ((Sep. 20, 1998).

Fieck et al., "Modifications of the *E. coli* Lac repressor for expression in eukaryotic cells: effects of nuclear signal sequences on protein activity and nuclear accumulation," *Nuc. Acids Res.*, 20(7):1785–1791 (1992).

Finkelstein et al., "The use of bi–cistronic transfer for the baculovirus expression system," *J. Biotechnol.*, 75(1):33–44 (Sep. 24, 1999).

Fletcher et al., "Mariner Transposon Mediated Stable Integration of Adenoviral Sequences for Use as Gene Therapy Vector System," Abstract 608, Fortieth Annual Meeting, American Society of Hematology, Miami Beach, Dec. 4–8, *Blood*, 92(10 Supp. 1, Part 1 of 2):151a (Nov. 15, 1998).

Gluzman et al., "Helper–free Adenovirus Type–5 Vectors," *Eukaryotic Viral Vectors*, Gluzman, ed., Cold Spring Harbor Laboratory Press, New York, title page, publication page, and pp. 187–192 (1982).

Gossen et al., "Tight control of gene expression in mammalian cells by tetracycline–responsive promoters," *Proc. Nat'l. Acad. Sci. USA*, 89(12):5547–5551 (1992).

Gossen et al., "Transcriptional Activation by Tetracyclines in Mammalian Cells," *Science*, 268:1766–1769 (1995).

Gueiros–Filho et al., "Trans–kingdom Transposition of the Drosophila Element mariner Within the Protozoan Leishmania," *Science*, 276:1716–1719 (1997).

Hackett et al., "Zebrafish as a model system for biomedical research," Grant Abstract, Grant No. 2R01RR06625–05A1 [online]. National Center for Research Resources, National Institutes of Health, project dates Aug. 1, 1991–Aug. 31, 2000 [retrieved on Apr. 11, 2001]. Retrieved from the Internet: URL: http://commons.cit.nih.gov/crisp_historical/crisp_lib.getdoc?textkey=2397786&p _grant_num= 2R01RR06625–05A1&p_p_query=&ticket=73379&p_ audit_session_i d=425461&p_keywords=, 2 pages.

Hardy et al., "Construction of Adenovirus Vectors through Cre–lox Recombination," *J. Virol.*, 71(3):1842–1849 (1997).

Hartl et al., "Construction sails into Leishmania," *Science*, 276(5319):1659–60 (1997).

Hirt, "Selective Extraction of Polyoma DNA from Infected Mouse Cell Cultures," *J. Mol. Biol.*, 26(2):365–369 (1967).

Hu et al., "The Inducible lac Operon–Repressor System Is Functional in Mammalian Cells," *Cell*, 48(4):555–566 (1987).

Ivics et al., "Development of Tc1–like transposable elements as genetic tools for Zebrafish (*Danio rerio*)," Abstract presented at "Second Biennial Meeting on Zebrafish Development and Genetics", Cold Spring Harbor Laboratory, Cold Spring Harbor, NY (Apr. 24–28, 1996).

Izsvak et al., "Nucleic acid sequence alignment and a predicted consensus sequence of the salmonid subfamily of Tc1–like transposable elements isolated from eight fish species," [online]. [retrieved Jun. 5, 2001]. Retrieved from the Internet:<URL:ftp://ftp.ebi.ac.uk/pub/databases/embl/align/ds30090.dat.; 10 pages.

Larregina et al., "FasL induces Fas/Apo1–mediated apoptosis in human embryonic kidney 293 cells routinely usedto generate E1–deleted adenoviral vectors," *Gene Ther.*, 5(4):563–568 (Apr. 1998).

McGrory et al., "A Simple Technique for the Rescue of Early Region I Mutations into Infectious Human Adenovirus Type 5," *Virol*, 163(2):614–617 (1988).

Moav et al. "Regulation of expression of transgenes in developing fish," *Transgenic Research*, 2:153–161 (1993).

Moerman et al., "Chapter 22: Mobile Elements in *Caenorhabditis elegans* and Other Nemotodes," *Mobile DNA*, Berg et al., eds., American Society for Microbiology, Title page, publication page, table of contents, and pp. 537–555 (1989).

Morral et al., "Administration of helper–dependent adenoviral vectors and sequential delivery of different vector serotype for long–term liver–directed gene transfer in baboons," *Proc. Nat'l. Acad. Sci. USA*, 96(22):12816–12821 (Oct. 26, 1999).

Parks et al., "A helper–dependent adenovirus vector system: Removal of helper virus by Cre–mediated excision of the viral packaging signal," *Proc. Nat'l. Acad. Sci. USA*, 93:13565–13570 (1996).

Tatusova et al., "Blast 2 Sequences, a new tool for comparing protein and nucleotide sequences," *FEMS Microbiol. Lett.*, 174(2):247–250 (May 15, 1999).

"Tet Expression Systems & Cells Lines, Mammalian cell cultures systems for tightly regulated, high–level gene expression," http://www.clontech.com/archive/JUL96UPD/Tet.html, 6 pages (Available on or before May 3, 2000).

"Tet System Vectors & Primers, Complete your Tet Systems tool kit with individual regulator and selection plasmids," http://www.clontech.com/archive/OCT96UPD/TetVectors.html, 3 pages (Available on or before Apr. 23, 2000).

Warren et al., "Physiological genomics': Mutant screens in zebrafish," *Am J Physiol.* 275(1 Pt 2):H1–7 (1998).

Webster et al., "One–Step, Two–Step Regulation of Therapeutic Genes," *The Scientist*, available on line at http://www.the–scientist.com/yr1999/apr/opin_990426.html (Apr. 26, 1999).

Ye et al., "Regulated Delivery of Therapeutic Proteins After in Vivo Somatic Cell Gene Transfer," *Science*, 283:88–91 (Jan. 1, 1999).

Zhang et al., "The Himar1 mariner transposase cloned in a recombinant adenovirus vector is functional in mammalian cells," *Nuc. Acids. Res.*, 26(16):3687–3693 (Aug. 15, 1998).

Adey et al., "Molecular resurrection of an extinct ancestral promoter for mouse L1," *Proc. Natl. Acad. Sci. USA*, 91, 1569–1573 (1994).

Allende et al., "Insertional mutagenesis in zebrafish identifies two novel genes, pescadillo and dead eye, essential for embryonic development," *Genes Dev.*, 10, 3141–3155 (1996).

Anderson et al., "Gene expression in rainbow trout (*Oncorhynchus mykiss*) following intramuscular injection of DNA," *Mol. Mar. Biol. Biotech.*, 5, 105–113 (1996).

*Antibodies: A Laboratory Manual*, Harlow and Lane, eds., Cold Spring Harbor Laboratory Press: Cold Spring Harbor, New York, Copyright page and Table of Contents (1988).

Ausubel, *Current Protocols in Molecular Biology*, Contents: vol. 1,2, and 3, Table of Contents (1994).

Ballinger et al., "Targeted gene mutations in Drosophila," *Proc. Natl. Acad. Sci. USA*, 86, 9402–9406 (1989).

Bellen et al., "P–element–mediated enhancer detection: a versatile method to study development in Drosophila," *Gens Dev.*,3, 1288–1300 (1989).

Bingham et al., "Cloning of DNA Sequences from the white Locus of *D. melanogaster* by a Novel and General Method," *Cell*, 25, 693–704 (1981).

Bradley et al., "Formation of germ–line chimaeras from embryo–derived teratocarcinoma cell lines," *Nature*, 309, 255–256 (1984).

Caldovic et al., "Development of position–independent expression vectors and their transfer into transgenic fish," *Molecular Marine Biology and Biotechnology*, 4, 51–61 (1995).

Collas et al., "The nuclear localization sequence of the SV40 Tantigen promotes transgene uptake and expression in zebrafish embryo nuclei," *Transgenic Res.*, 5, 451–458 (1996).

Colloms et al., "DNA binding activities of the Caenorhabditis elegans Tc3 transposase," *Nucl. Acids Res.*, 22, 5548–5554 (1994).

Cooley et al., "Insertional Mutagenesis of the Drosophila Genome with Single P Elements," *Science*, 239, 1121–1128 (1988).

Dalton et al., "Separation of Recombinant Human Protein C from Transgenic Animal Milk Using Immobilized Metal Affinity Chromatography," *Adv. Exp. Med. Biol.*, 411, 419–428 (1997).

Dawson et al., "Sleeping beauty awakes," *Nature Biotechnology*, 16, 20–21 (1998).

Devon et al., "Splinkerettes—improved vectorettes for greater efficiency in PCR walking," *Nucl. Acids. Res.*, 23, 1644–1645 (1995).

Doak et al., "A proposed superfamily of transposase genes: Transposon–like elements in ciliated proozoa and a common 'D35E' motif," *Proc. Natl. Acad. Sci. USA*, 91, 942–946 (1994).

Evans et al., "Gene trapping and functional genomics," *TIG*, 13, 370–374 (1997).

Gibbs et al., "Inheritance of P element and reporter gene sequences in zebrafish," *Mol. Mar. Biol. Biotech.*, 3, 317–326 (1994).

Gierl et al., "TnpA product encoded by the transposable element En–1 of *Zea mays* is a DNA binding protein," *EMBO J.*, 7, 4045–4053 (1988).

Gonzales et al., "Transposon mutagenesis of Haemophilus paragallinarum with Tn916," *Vet. Microbiol.*, 48, 283–291 (1996).

Goodier et al., "Tc1 Transposon–like Sequences are Widely Distributed in Salmonids," *J. Mol. Biol.*, 241, 26–34 (1994).

Hackett et al., "The molecular biology of transgenic fish," *Biochemistry and Molecular Biology of Fishes*, 2, Hochachka and Mommsen, eds., 207–240 (1993).

Hackett et al., "Development of Genetic Tools for Transgenic Fish," Abstract, Seminars in Singapore, Jul. 29–30, 1997 & UC Davis Biotechnology Program, Granlibakken Conference Center, Aug. 24–27, 1997.

Handler et al., "A Functional Analysis of the P–element Gene–Transfer Vector in Insects," *Arch. Insect Biochem. Physiol.*, 22, 373–384 (1993).

Hartl et al., "What restricts the activity of mariner–like transposable elements," *Trends Genet.*, 13, 197–201 (1997).

Ivics et al., "Repeated Sequence Elements in Zebrafish and Their Use in Molecular Genetic Studies," *The Zebrafish Science Monitor*, 3, 1–4 (1995).

Ivics et al., "Molecular Reconstruction of Sleeping Beauty, a Tc1–like Transposon from Fish, and Its Transposition in Human Cells," *Cell*, 91, 501–510 (1997).

Ivics et al., "Identification of functional domains and evolution of Tc1–like transposable elements," *Proc. Natl. Acad. Sci. USA*, 93, 5008–5013 (1996).

Izsvak et al., Characterization of a Tc1–like transposable element in zebrafish (*Danio rerio*), *Mol. Gen. Genet.*, 247, 312–322 (1995).

Izsvak et al., "Repetitive elements and their genetic applications in zebrafish," *Biochem. Cell Biol.*, 75, 507–523 (1997).

Jermann et al., "Reconstructing the evolutionary history of the artiodactyl ribonuclease superfamily," *Nature*, 374, 57–59 (1995).

Kidwell, "Horizontal transfer," *Curr. Opin. Genet. Dev.*, 2, 868–873 (1992).

Koga et al., "Transposable element in fish," *Nature*, 383, 30 (1996).

Korswagen et al., "Transposon Tc1–derived, sequence–tagged sites in *Caenorhabditis elegans* as markers for gene mapping," *Proc. Natl. Acad. Sci. USA*, 93, 14680–14685 (1996).

Lam et al., "Discovery of Amphibian Tc1–like Transposon Families," *J. Mol. Biol.*, 257, 359–366 (1996).

Lam et al., "Active transposition in zebrafish," *Proc. Natl. Acad. Sci. USA*, 93, 10870–10875 (1996).

Lampe et al., "A purified mariner transposase in sufficient to mediate transposition in vitro," *EMBO J.*, 15, 5470–5479 (1996).

Lee et al., "Tn 10 insertional mutagenesis in *Pasteurella multocida*," *Vet. Microbiol.*, 50, 143–148 (1996).

Lohe et al., "Horizontal Transmission, Vertical Inactivation, and Stochastic Loss of Mariner–like Transposable Elements," *Mol. Biol. Evol.*, 12, 62–72 (1995).

Lohe et al., "Mutations in the mariner transposase: The D, D(35)E consensus sequence is nonfunctional," *Proc. Natl. Acad. Sci. USA*, 94, 1293–1297 (1997).

Loukeris et al., "Gene Transfer into the Medfly, *Ceratitis capitata*, with a *Drosophila hydei* Transposable Element," *Science*, 270, 2002–2005 (1995).

Lubon et al., "Blood Proteins from Transgenic Animal Bioreactors," *Transfusion Med. Rev.*, 10, 131–143 (1996).

Luo et al., "Chromosomal transposition of a Tc1/marinerlike element in mouse embryonic stem cells," *Proc. Natl. Acad. Sci. USA*, 95, 10769–10773 (1998).

Markkula et al., "Transgenic animals and gonadotrophins," *Rev. Reprod.*, 1, 97–106 (1996).

Michael, "Mutagenesis by Incorporation of a Phosphorylated Oligo During PCR Amplification," *BioTechniques*, 16, 410–412 (1994).

Morgan et al., "Transposon tools fro recombinant DNA manipulation: Characterization of transcriptional regulators from yeast, Xenopus, and mouse," *Proc. Natl. Acad. Sci. USA*, 93, 2801–2806 (1996).

Oosumi et al., "Mariner transposons in humans," *Nature*, 378, 873 (1995).

Osborne et al., "Movers and shakers: maize transposons as tools for analyzing other plant genomes," *Curr. Opin. Cell Biol.*, 7, 406–413 (1995).

Perucho et al., "Genetic and Physical Linkage of Exogenous Sequences in Transformed Cells," *Cell*, 22, 309–317 (1980).

Plasterk, "The Tc1/mariner Transposon Family," *Curr. Top. Microbiol. Immunol.*, 204, 125–143 (1996).

Plasterk, "Reverse Genetics: From Gene Sequence to Mutant Worm," *Meth. Cell. Biol.*, 8, Academic Press, Inc., Chapter 3, 59–80 (1995).

Plasterk, "Molecular Mechanisms of Transposition and Its Control," *Cell*, 74, 781–786 (1993).

Radice et al., "Widespread occurrence of the Tc1 transposon family: Tc1–like transposons from teleost fish," *Mol. Gen. Genet.*, 244, 606–612 (1994).

Rio et al., "Evidence from Drosophila P Element Transposase Activity in Mammalian Cells and Yeast," *J. Mol. Biol.*, 200, 411–415 (1988).

Sambrook et al., *Molecular Cloning: A Laboratory Manual*, Cold Spring Harbor Laboratory Press, table of contents and title page (1989).

Sarkar et al., "The 'Megaprimer' Method of Site–Directed Mutagenesis," *BioTechniques*, 8, 404–407 (1990).

Sherratt, *Mobile Genetic Elements*, IRL Press, Oxford (1995).

Smit et al., "Tiggers and other DNA transposon fossils in the human genome," *Proc. Natl. Acad. Sci. USA*, 93, 1443–1448 (1996).

Spradling et al., "Gene disruptions using P transposable elements: An integral component of the Drosophila genome project," *Proc. Natl. Acad. Sci. USA*, 92, 10824–10830 (1995).

Stewart, "Active ancestral molecules," *Nature*, 374, 12–13 (1995).

van Luenen et al., "The Mechanism of Transposition of Tc3 in *C. elegans*," *Cell*, 79, 293–301 (1994).

van Luenen et al., "Target site choice of the related transposable elements Tc1 and Tc3 of *Caenorhabditis elegans*," *Nucleic Acids Research*, 22, 262–269 (1994).

van Luenen et al., "Mobilization of quiet, endogenous Tc3 transposons of *Caenorhabditis elegans* by forced expression of Tc3 transposase," *EMBO J.*, 12, 2513–2520 (1993).

Vos et al., "Tc1 transposase of *Caenorhabditis elegans* is an endonuclease with a bipartite DNA binding domain," *EMBO J.*, 13, 6125–6132 (1994).

Vos et al., "Transposase in the only nematode protein required for in vitro transposition of Tc1," *Genes. Dev.*, 10, 755–761 (1996).

Vos et al., "Characterization of the *Caenorhabditis elegans* Tc1 transposase in vivo and in vitro," *Genes. Dev.*, 7, 1244–1253 (1993).

Wall et al., "Transgenic Dairy Cattle: Genetic Engineering on a Large Scale," *J. Dairy Sci.*, 80, 2213–2224 (1997).

Young et al., "Production of Biopharmaceutical Proteins in the Milk of Transgenic Dairy Animals," *Bio Pharm*, 10, 34–38 (1997).

Ivics et al. Identification of Functional Domains and Evolution of Tc1–Like Transposable Elements. PNAS, vol. 93, pp. 5008–5013, May 1996.*

Eck et al. Gene–Based Therapy. Goodman & Gilman's The Pharmacological Basis of Therapeutics, Chapter 5, 1996.*

Verma et al. Gene Therapy–Promises, Problems, and Prospects. Nature, vol. 389, pp. 239–242, Sep. 1997.*

* cited by examiner

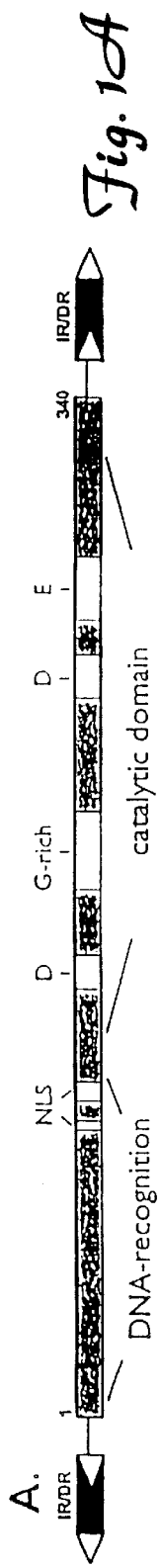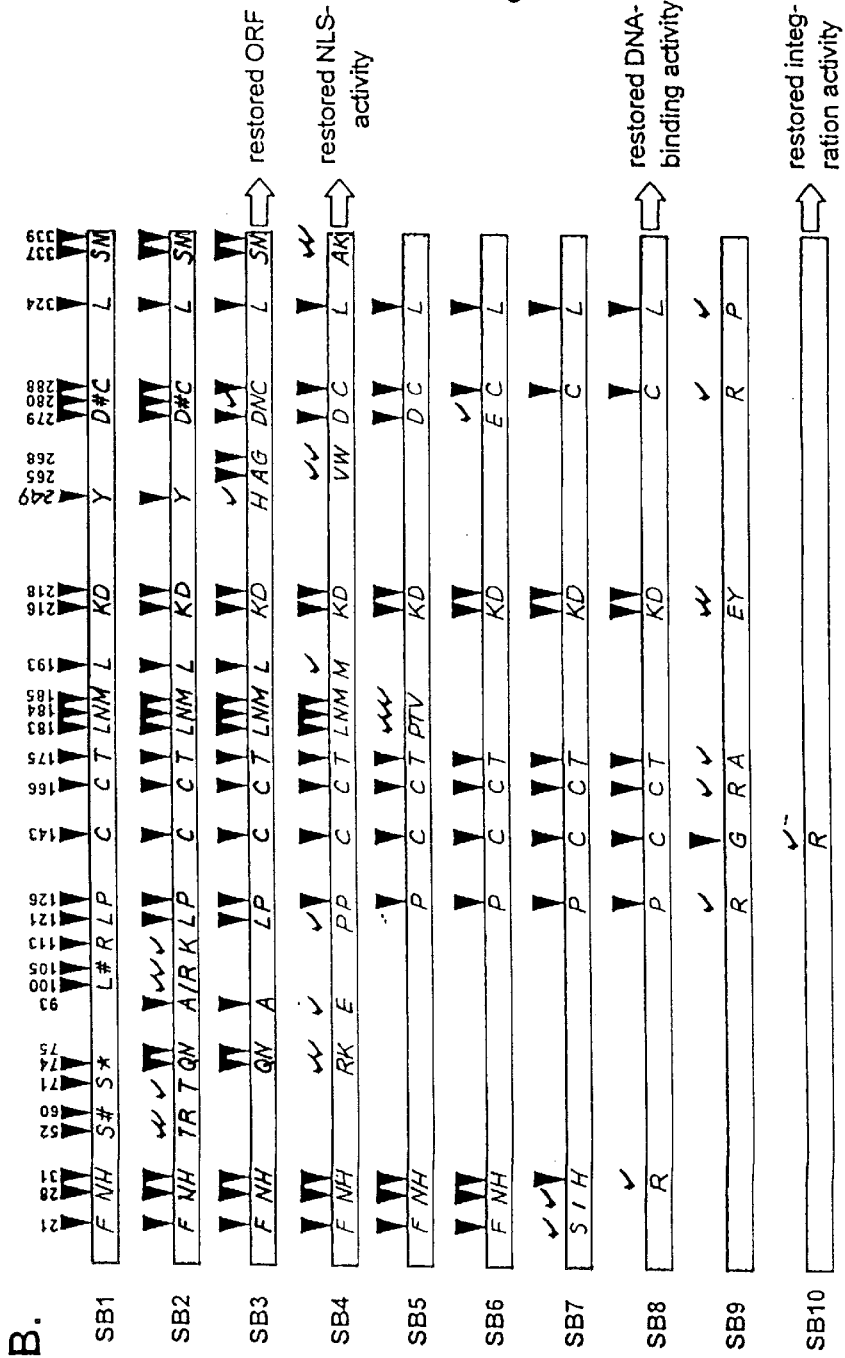
Fig. 1A
Fig. 1B (SEQ ID NO:3)

```
   1   ATGGGAAAA TCAAAAGAAA TCAGCCAAGA CCTCAGAAAA
       TACCCTTTT AGTTTTCTTT AGTCGGTTCT GGAGTCTTTT

51   AAAATTGTAG ACCTCCACAA GTCTGGTTCA TCCTTGGGAG CAATTTCCAA
       TTTTAACATC TGGAGGTGTT CAGACCAAGT AGGAACCCTC GTTAAAGGTT

101   ACGCCTGAAA GTACCACGTT CATCTGTACA AACAATAGTA CGCAAGTATA
       TGCGGACTTT CATGGTGCAA GTAGACATGT TTGTTATCAT GCGTTCATAT

151   AACACCATGG GACCACGCAG CCGTCATACC GCTCAGGAAG GAGACGCGTT
       TTGTGGTACC CTGGTGCGTC GGCAGTATGG CGAGTCCTTC CTCTGCGCAA

201   CTGTCTCCTA GAGATGAACG TACTTTGGTG CGAAAAGTGC AAATCAATCC
       GACAGAGGAT CTCTACTTGC ATGAAACCAC GCTTTTCACG TTTAGTTAGG

251   CAGAACAACA GCAAAGGACC TTGTGAAGAT GCTGGAGGAA ACAGGTACAA
       GTCTTGTTGT CGTTTCCTGG AACACTTCTA CGACCTCCTT TGTCCATGTT

301   AAGTATCTAT ATCCACAGTA AAACGAGTCC TATATCGACA TAACCTGAAA
       TTCATAGATA TAGGTGTCAT TTTGCTCAGG ATATAGCTGT ATTGGACTTT

351   GGCCGCTCAG CAAGGAAGAA GCCACTGCTC CAAAACCGAC ATAAGAAAGC
       CCGGCGAGTC GTTCCTTCTT CGGTGACGAG GTTTTGGCTG TATTCTTTCG

401   CAGACTACGG TTTGCAACTG CACATGGGGA CAAAGATCGT ACTTTTTGGA
       GTCTGATGCC AAACGTTGAC GTGTACCCCT GTTTCTAGCA TGAAAAACCT

451   GAAATGTCCT CTGGTCTGAT GAAACAAAAA TAGAACTGTT TGGCCATAAT
       CTTTACAGGA GACCAGACTA CTTTGTTTTT ATCTTGACAA ACCGGTATTA

501   GACCATCGTT ATGTTTGGAG GAAGAAGGGG GAGGCTTGCA AGCCGAAGAA
       CTGGTAGCAA TACAAACCTC CTTCTTCCCC CTCCGAACGT TCGGCTTCTT

551   CACCATCCCA ACCGTGAAGC ACGGGGGTGG CAGCATCATG TTGTGGGGGT
       GTGGTAGGGT TGGCACTTCG TGCCCCCACC GTCGTAGTAC AACACCCCCA

601   GCTTTGCTGC AGGAGGGACT GGTGCACTTC ACAAAATAGA TGGCATCATG
       CGAAACGACG TCCTCCCTGA CCACGTGAAG TGTTTTATCT ACCGTAGTAC

651   AGGAAGGAAA ATTATGTGGA TATATTGAAG CAACATCTCA AGACATCAGT
       TCCTTCCTTT TAATACACCT ATATAACTTC GTTGTAGAGT TCTGTAGTCA

701   CAGGAAGTTA AAGCTTGGTC GCAAATGGGT CTTCCAAATG GACAATGACC
       GTCCTTCAAT TTCGAACCAG CGTTTACCCA GAAGGTTTAC CTGTTACTGG

751   CCAAGCATAC TTCCAAAGTT GTGGCAAAAT GGCTTAAGGA CAACAAAGTC
       GGTTCGTATG AAGGTTTCAA CACCGTTTTA CCGAATTCCT GTTGTTTCAG

801   AAGGTATTGG AGTGGCCATC ACAAAGCCCT GACCTCAATC CTATAGAAAA
       TTCCATAACC TCACCGGTAG TGTTTCGGGA CTGGAGTTAG GATATCTTTT

851   TTTGTGGGCA GAACTGAAAA AGCGTGTGCG AGCAAGGAGG CCTACAAACC
       AAACACCCGT CTTGACTTTT TCGCACACGC TCGTTCCTCC GGATGTTTGG

901   TGACTCAGTT ACACCAGCTC TGTCAGGAGG AATGGGCCAA AATTCACCCA
       ACTGAGTCAA TGTGGTCGAG ACAGTCCTCC TTACCCGGTT TTAAGTGGGT

951   ACTTATTGTG GGAAGCTTGT GGAAGGCTAC CCGAAACGTT TGACCCAAGT
       TGAATAACAC CCTTCGAACA CCTTCCGATG GGCTTTGCAA ACTGGGTTCA

1001   TAAACAATTT AAAGGCAATG CTACCAAATA CTAG.
       ATTTGTTAAA TTTCCGTTAC GATGGTTTAT GATC
```

Fig. 2A

Paired-like domain with Leucine-zipper

```
  1  MGKSKEISQD LRKKIVDLHK SGSSLGAISK RLKVPRSSVQ TIVPKYKHHG

51  TTQPSYRSGR RVLSPRDER  TLVRKVQINP RTTAKDLVKM LEETGTKVSI
              NLS
101  STVKRVLYRH NLKGRSARKK PLLQNRHKKA RLRFATAHGD KDRTFWRNVL

151  WSDETKIELF GHNDHRYVWR KKGEACKPKN TIPTVKHGGG SIMLWGCFAA
                                        Glycine-rich box
201  GGTGALHKID GIMRKENYVD ILKQHLKTSV RKLKLGRKWV FQMDNDPKHT

251  SKVVAKWLKD NKVKVLEWPS QSPDLNPIEN LWAELKKRVR ARRPTNLTQL

301  HQLCQEEWAK IHPTYCGKLV EGYPKRLTQV KQFKGNATKY * (SEQ ID NO:1)
                                        DD(34)E box
```

Fig. 2B

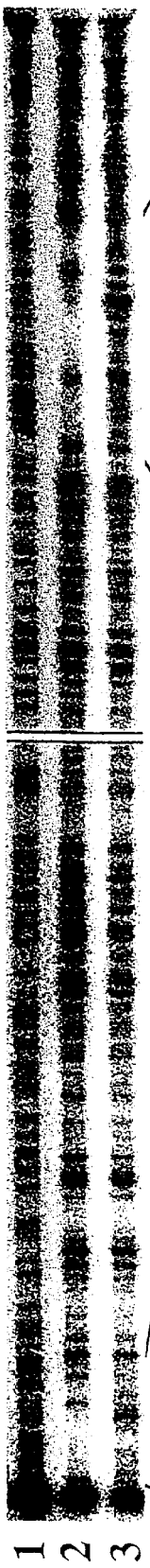
Fig. 4A
Fig. 4B
gttgaagtcggaagtttacatacacttagg (SEQ ID NO:37) - salmonid
||| || ||||||||||||||||||| ||||
gtttaaaccagaagtttacatacacactgtat (SEQ ID NO:38) - zebrafish
ccagtgggtcagaagtttacatacactaag (SEQ ID NO:39)
||| ||||| |||||||||||||| ||||
cttgaaagtc..aagtttacatacaataag (SEQ ID NO:40)
Fig. 4C
C.
External tacagttgaagtcggaagtttacatacacttagg (SEQ ID NO:41)
         ||||  ||| |||||||||||||||||||||
Internal tccagtgg..gtcagaagtttacatacacactaagt (SEQ ID NO:42)

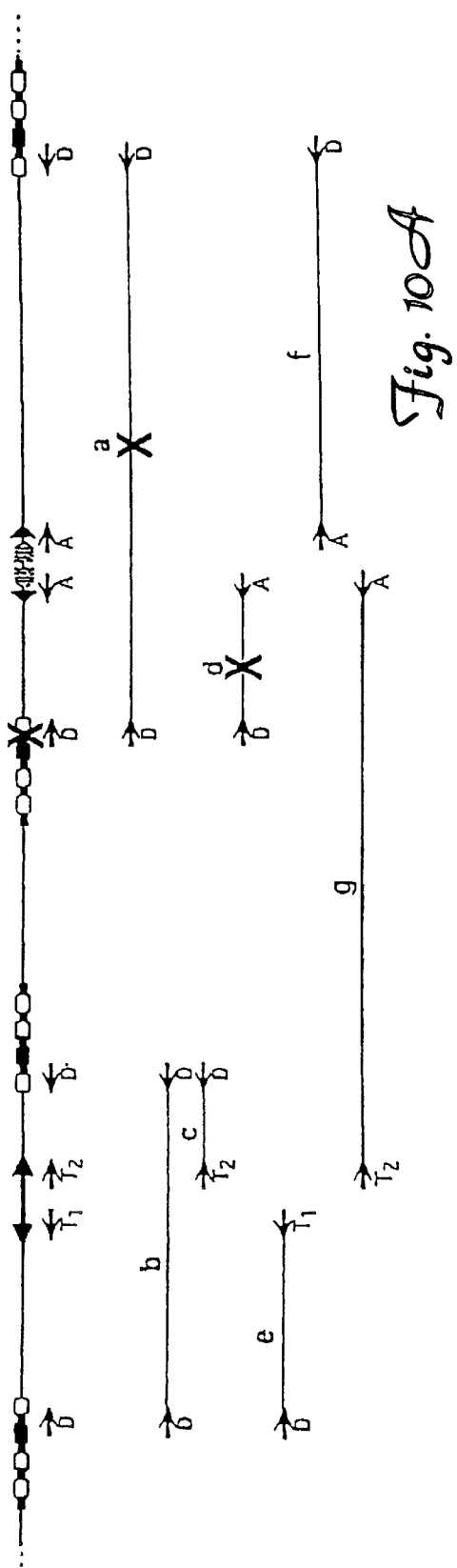
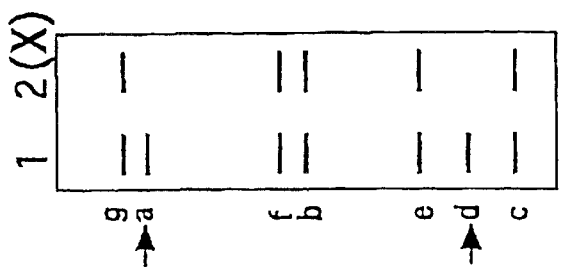
Fig. 10A
Fig. 10B
Generate sequence-tagged sites (STS) by isolation of fragments a and d and place them on a genetic map.

DNA-BASED TRANSPOSON SYSTEM FOR THE INTRODUCTION OF NUCLEIC ACID INTO DNA OF A CELL

This application claims benefit of Provisional Applications Nos. 60/040,664 filed Mar. 11, 1997, 60/053,868 filed Jul. 28, 1997 and 60/065,303 filed Nov. 13, 1997.

STATEMENT REGARDING GOVERNMENT RIGHTS

This invention was made with government support from the United States Department of Agriculture, USDA Grant No. 92-37205-7842; National Institutes of Health, NIH Grant No. R01-RR0625; and SeaGrant No. USDOC/NA46RG o101-04. The government may have certain rights in this invention.

FIELD OF THE INVENTION

This invention relates to methods for gene expression, mapping genes, mutagenesis, methods for introducing DNA into a host chromosome and to transposons and transposases.

Transposons or transposable elements include a short piece of nucleic acid bounded by repeat sequences. Active transposons encode enzymes that facilitate the insertion of the nucleic acid into DNA sequences.

In vertebrates, the discovery of DNA-transposons, mobile elements that move via a DNA intermediate, is relatively recent (Radice, A. D., et al., 1994. *Mol. Gen. Genet.* 244, 606–612). Since then, inactive, highly mutated members of the Tc1/mariner as well as the hAT (hobo/Ac/Tam) superfamilies of eukaryotic transposons have been isolated from different fish species, Xenopus and human genomes (Oosumi et al., 1995. *Nature* 378, 873; Ivics et al. 1995. *Mol. Gen. Genet.* 247, 312–322; Koga et al., 1996. *Nature* 383, 30; Lam et al., 1996. *J. Mol. Biol.* 257, 359–366 and Lam, W. L., et al. *Proc. Natl. Acad Sci. USA* 93, 10870–10875).

These transposable elements transpose through a cut-and-paste mechanism; the element-encoded transposase catalyzes the excision of the transposon from its original location and promotes its reintegration elsewhere in the genome (Plasterk, 1996 *Curr. Top. Microbiol. Immunol.* 204, 125–143). Autonomous members of a transposon family can express an active transposase, the trans-acting factor for transposition, and thus are capable of transposing on their own. Nonautonomous elements have mutated transposase genes but may retain cis-acting DNA sequences. These cis-acting DNA sequences are also referred to as inverted terminal repeats. Some inverted repeat sequences include one or more direct repeat sequences. These sequences usually are embedded in the terminal inverted repeats (IRs) of the elements, which are required for mobilization in the presence of a complementary transposase from another element.

Not a single autonomous element has been isolated from vertebrates; all transposon-like sequences are defective, apparently as a result of a process called "vertical inactivation" (Lohe et al., 1995 *Mol. Biol. Evol.* 12, 62–72). According to one phylogenetic model (Hartl et al., 1997 *Trends Genet.* 13, 197–201), the ratio of nonautonomous to autonomous elements in eukaryotic genomes increases as a result of the trans-complementary nature of transposition. This process leads to a state where the ultimate disappearance of active, transposase-producing copies in a genome is inevitable. Consequently, DNA-transposons can be viewed as transitory components of genomes which, in order to avoid extinction, must find ways to establish themselves in a new host. Indeed, horizontal gene transmission between species is thought to be one of the important processes in the evolution of transposons (Lohe et al., 1995 supra and Kidwell, 1992. *Curr. Opin. Genet Dev.* 2, 868–873).

The natural process of horizontal gene transfer can be mimicked under laboratory conditions. In plants, transposable elements of the Ac/Ds and Spm families have been routinely introduced into heterologous species (Osborne and Baker, 1995 *Curr. Opin. Cell Biol.* 7, 406–413). In animals, however, a major obstacle to the transfer of an active transposon system from one species to another has been that of species-specificity of transposition due to the requirement for factors produced by the natural host. For this reason, attempts have been unsuccessful to use the P element transposon of *Drosophila melanogaster* for genetic transformation of non-drosophilid insects, zebrafish and mammalian cells (Gibbs et al., 1994 *Mol. Mar. Biol. Biotech.* 3, 317–326; Handler et al., 1993. *Arch. Insect Biochem. Physiol.* 22, 373–384; and Rio et al., 1988 *J. Mol. Biol.* 200, 411–415). In contrast to P elements, members of the Tc1/mariner superfamily of transposable elements may not be as demanding for species-specific factors for their transposition. These elements are widespread in nature, ranging from single-cellular organisms to humans (Plasterk, 1996, supra). In addition, recombinant Tc1 and mariner transposases expressed in *E. coli* are sufficient to catalyze transposition in vitro (Vos et al, 1996 *Genes. Dev.* 10, 755–761 and Lampe et al., 1996. *EMBO J.* 15, 5470–5479 and PCT International Publication No. WO 97/29202 to Plasterk et al.). Furthermore, gene vectors based on Minos, a Tc1-like element (TcE) endogenous to *Drosophila hydei*, were successfully used for germline transformation of the fly *Ceratitis capitata* (Loukeris et al., 1995 *Science* 270, 2002–2005).

Molecular phylogenetic analyses have shown that the majority of the fish TcEs can be classified into three major types: zebrafish-, salmonid- and Xenopus TXr-type elements, of which the salmonid subfamily is probably the youngest and thus most recently active (Ivics et al., 1996, *Proc. Natl. Acad. Sci. USA* 93, 5008–5013). In addition, examination of the phylogeny of salmonid TcEs and that of their host species provides important clues about the ability of this particular subfamily of elements to invade and establish permanent residences in naive genomes through horizontal transfer, even over relatively large evolutionary distances.

TcEs from teleost fish (Goodier and Davidson, 1994 *J. Mol. Biol.* 241, 26–34 and Izsvak et al., 1995. *Mol. Gen. Genet.* 247, 312–322), including Tdr1 in zebrafish (Izsvak et al., 1995, supra) and other closely related TcEs from nine additional fish species (Ivics et al., 1996. *Proc. Natl. Acad. Sci. USA* 93, 5008–5013) are by far the best characterized of all the DNA-transposons known in vertebrates. Fish elements, and other TcEs in general, are typified by a single gene encoding a transposase enzyme flanked by inverted repeat sequences. Unfortunately, all the fish elements isolated so far are inactive due to one or more mutations in the transposase genes.

Methods for introducing DNA into a cell are known. These include, but are not limited to, DNA condensing reagents such as calcium phosphate, polyethylene glycol, and the like), lipid-containing reagents, such as liposomes, multi-lamellar vesicles, and the like, and virus-mediated strategies. These methods all have their limitations. For example, there are size constraints associated with DNA condensing reagents and virus-mediated strategies. Further, the amount of nucleic acid that can be introduced into a cell is limited in virus strategies. Not all methods facilitate integration of the delivered nucleic acid into cellular nucleic acid and while DNA condensing methods and lipid-containing reagents are relatively easy to prepare, the incorporation of nucleic acid into viral vectors can be labor intensive. Moreover, virus-mediated strategies can be cell-type or tissue-type specific and the use of virus-mediated strategies can create immunologic problems when used in vivo.

There remains a need for new methods for introducing DNA into a cell, particularly methods that promote the efficient integration of nucleic acid fragments of varying sizes into the nucleic acid of a cell, particularly the integration of DNA into the genome of a cell.

SUMMARY OF THE INVENTION

We have developed a DNA-based transposon system for genome manipulation in vertebrates. Members of the Tc1/mariner superfamily of transposons are prevalent components of the genomes of teleost fish as well as a variety of other vertebrates. However, all the elements isolated from nature appear to be transpositionally inactive. Molecular phylogenetic data were used to identify a family of synthetic, salmonid-type Tc1-like transposases (SB) with their recognition sites that facilitate transposition. A consensus sequence of a putative transposase gene was first derived from inactive elements of the salmonid subfamily of elements from eight species of fish and then engineered by eliminating the mutations that rendered these elements inactive. A transposase was created in which functional domains were identified and tested for biochemical functions individually as well as in the context of a full-length transposase. The transposase binds to two binding-sites within the inverted repeats of salmonid elements, and appears to be substrate-specific, which could prevent cross-mobilization between closely related subfamilies of fish elements. SB transposases significantly enhance chromosomal integration of engineered transposons not only in fish, but also in mouse and in human cells. The requirements for specific motifs in the transposase plus specific sequences in the target transposon, along with activity in fish and mammalian cells alike, establishes SB transposase as the first active DNA-transposon system for germline transformation and insertional mutagenesis in vertebrates. In one aspect of this invention, the invention relates to a nucleic acid fragment comprising: a nucleic acid sequence positioned between at least two inverted repeats wherein the inverted repeats can bind to a SB protein and wherein the nucleic acid fragment is capable of integrating into DNA in a cell. In one embodiment nucleic acid fragment is part of a plasmid and preferably the nucleic acid sequence comprises at least a portion of an open reading frame and also preferably at least one expression control region of a gene. In one embodiment, the expression control region is selected from the group consisting of a promoter, an enhancer or a silencer. Preferably the nucleic acid sequence comprises a promoter operably linked to at least a portion of an open reading frame.

In one embodiment the cell is obtained from an animal such as an invertebrate or a vertebrate. Preferred invertebrates include crustacean or a mollusk including, but not limited to a shrimp, a scallop, a lobster, a clam or an oyster. Preferred vertebrate embodiments include fish, birds, and mammal such as those selected from the group consisting of mice, ungulates, sheep, swine, and humans. The DNA of the cell can be the cell genome or extrachromosomal DNA, including an episome or a plasmid.

In one embodiment of this aspect of the invention, at least one of the inverted repeats comprises SEQ ID NO:4 or SEQ ID NO: 5 and preferably the amino acid sequence of the SB protein has at least an 80% amino acid identity to SEQ ID NO: 1. Also preferably, at least one of the inverted repeats comprises at least one direct repeat, wherein the at least one direct repeat sequence comprises SEQ ID NO: 6, SEQ ID NO: 7, SEQ ID NO: 8 or SEQ ID NO:9. A preferred direct repeat is SEQ ID NO:10. Also preferably the nucleic acid fragment includes a direct repeat that has at least an 80% nucleic acid sequence identity to SEQ ID NO: 10.

In another aspect of this invention, the invention relates to a gene transfer system to introduce DNA into the DNA of a cell comprising: a nucleic acid fragment comprising a nucleic acid sequence positioned between at least two inverted repeats wherein the inverted repeats can bind to an SB protein and wherein the nucleic acid fragment is capable of integrating into DNA of a cell; and a transposase or nucleic acid encoding a transposase, wherein the transposase is an SB protein with an amino acid sequence sharing at least an 80% identity to SEQ ID NO:1. In one embodiment, the SB protein comprises SEQ ID NO:1. Alternatively, the SB protein is encoded by DNA that can hybridize to SEQ ID NO:3 under stringent hybridization conditions. In one embodiment, the transposase is provided to the cell as a protein and in another the transposase is provided to the cell as nucleic acid. In one embodiment the nucleic acid is RNA and in another the nucleic acid is DNA. In yet another embodiment, the nucleic acid encoding the transposase is integrated into the genome of the cell. The nucleic acid fragment can be part of a plasmid or a recombinant viral vector. Preferably, the nucleic acid sequence comprises at least a portion of an open reading frame and also preferably, the nucleic acid sequence comprises at least a regulatory region of a gene. In one embodiment the regulatory region is a transcriptional regulatory region and the regulatory region is selected from the group consisting of a promoter, an enhancer, a silencer, a locus-control region, and a border element. In another embodiment, the nucleic acid sequence comprises a promoter operably linked to at least a portion of an open reading frame.

The cells used in this aspect of the invention can be obtained from a variety of sources including bacteria, fungi, plants and animals. In one embodiment, the cells are obtained from an animal; either a vertebrate or an invertebrate. Preferred invertebrate cells include crustaceans or a mollusks. Preferred vertebrates include fish, birds, and mammal such as rodents, ungulates, sheep, swine and humans.

The DNA of the cell receiving the nucleic acid fragment can be a part of the cell genome or extrachromosomal DNA. Preferably, the inverted repeats of the gene transfer system comprise SEQ ID NO:4 or SEQ ID NO:5. Also preferably the amino acid sequence of the SB protein has at least a 80% identity to SEQ ID NO:1 and preferably at least one of the inverted repeats comprises at least one direct repeat and wherein the at least one direct repeat sequence comprises SEQ ID NO:6, SEQ ID NO: 7, SEQ ID NO:8 or SEQ ID NO:9. In one embodiment, the direct repeat has a consensus sequence of SEQ ID NO:10. In a particularly preferred embodiment, the nucleic acid sequence is part of a library of recombinant sequences and the nucleic acid sequence is introduced into the cell using a method selected from the group consisting of: particle bombardment, electroporation, microinjection, combining the nucleic acid fragment with lipid-containing vesicles or DNA condensing reagents, and incorporating the nucleic acid fragment into a viral vector and contacting the viral vector with the cell.

In another aspect of this invention, the invention relates to nucleic acid encoding an SB protein, wherein the nucleic acid encodes a protein comprising SEQ ID NO:1 or a protein comprising an amino acid sequence with at least 80% identity to SEQ ID NO:1. The nucleic acid encoding the SB protein can be incorporated into a nucleic acid vector, such as a gene expression vector either as a viral vector or as a plasmid. The nucleic acid can be circular or linear. This invention also relates to cells expressing the SB protein.

In one embodiment the cells containing the SB protein cell are obtained from an animal, either a vertebrate or an invertebrate. Preferred vertebrates include fish, birds and mammals. The cells can be obtained from a variety of tissues including pluripotent and totipotent cells such as an oocyte, one or more cells of an embryo, or an egg. In one embodiment, the cell is part of a tissue or organ. In one embodiment, the nucleic acid encoding the SB protein is integrated in the genome of a cell.

The invention also relates to SB protein comprising the amino acid sequence of SEQ ID NO:1.

In addition, the invention relates to a method for producing a transgenic animal comprising the steps of: introducing a nucleic acid fragment and a transposase into a pluripotent or totipotent cell wherein the nucleic acid fragment comprises a nucleic acid sequence positioned between at least two inverted repeats, wherein the inverted repeats can bind to a SB protein and wherein the nucleic acid fragment is capable of integrating into DNA in a cell and wherein the transposase is an SB protein having an amino acid sequence identity of least 80% to SEQ ID NO:1; and growing the cell into an animal. Preferred pluripotent or totipotent cells include an oocyte, a cell of an embryo, an egg and a stem cell. In one embodiment, the introducing step comprises a method selected from the group consisting of: microinjection; combining the nucleic acid fragment with cationic lipid vesicles or DNA condensing reagents; and incorporating the nucleic acid fragment into a viral vector and contacting the viral vector with the cell as well as particle bombardment and electroporation. In another preferred embodiment the viral vector is selected from the group consisting of a retroviral vector, an adenovirus vector, a herpesvirus or an adeno-associated viral vector. Preferred animals used in this method include a mouse, a fish, an ungulate, a bird, or a sheep.

In yet another aspect of this invention, the invention relates to a method for introducing nucleic acid into DNA in a cell comprising the step of: introducing a nucleic acid fragment comprising a nucleic acid sequence positioned between at least two inverted repeats into a cell wherein the inverted repeats can bind to an SB protein and wherein the nucleic acid fragment is capable of integrating into DNA in a cell in the presence of an SB protein. In a preferred embodiment, the method further comprises introducing an SB protein into the cell. In one embodiment, the SB protein has an amino acid sequence comprising at least a 80% identity to SEQ ID NO:1. The SB protein can be introduced into the cell as protein or as nucleic acid, including RNA or DNA. The cell receiving the nucleic acid fragment can already include nucleic acid encoding an SB protein and already express the protein. In a one embodiment, the SB protein is integrated into the cell genome. The SB protein can be stably expressed in the cell or transiently expressed and nucleic acid encoding the SB protein can be under the control of an inducible promoter or under the control of a constitutive promoter. In one aspect of this method, the introducing step comprises a method for introducing nucleic acid into a cell selected from the group consisting of: microinjection; combining the nucleic acid fragment with cationic lipid vesicles or DNA condensing reagents; and incorporating the nucleic acid fragment into a viral vector and contacting the viral vector with the cell. Preferred viral vectors are selected from the group consisting of a retroviral vector, an adenovirus vector or an adeno-associated viral vector. In another aspect of this method, the method includes the step of introducing an SB protein or RNA encoding an SB protein into the cell. The cells used for this method can be pluripotent or a totipotent cell and this invention also relates to transgenic animals produced by this method. Where transgenic animals are produced, the nucleic acid sequence preferably encodes a protein and preferably a protein to be collected from the transgenic animal or a marker protein. The invention also relates to those cells of the transgenic animal expressing the protein encoded by the nucleic acid sequence.

The invention also relates to a SB protein. In one embodiment the protein has the following characteristics: an ability to catalyze the integration of nucleic acid into DNA of a cell; capable of binding to the inverted repeat sequence of SEQ ID NOS 4 or 5; and 80% amino acid sequence identity to SEQ ID NO:1. In another embodiment, the protein has the following characteristics: transposase activity; a molecular weight range of about 35 kD to about 40 kD on about a 10% SDS-polyacrylamide gel; and an NLS sequence, a DNA binding domain and a catalytic domain and wherein the protein has at least about five-fold improvement in the rate for introducing a nucleic acid fragment into the nucleic acid of a cell as compared to the level obtained by non-homologous recombination. Preferred methods for testing the rate of nucleic acid fragment incorporation is provided in the examples.

In yet another aspect, the invention relates to a method for mobilizing a nucleic acid sequence in a cell comprising the steps of: introducing the protein of this invention into a cell housing DNA containing the nucleic acid fragment of this invention, wherein the protein mobilizes the nucleic acid fragment from a first position within the DNA of a cell to a second position within the DNA of the cell. In one embodiment, the DNA of a cell is genomic DNA. In another, the first position within the DNA of a cell is extrachromosomal DNA and in yet another, the second position within the DNA of a cell is extrachromosomal DNA. In a preferred embodiment, the protein is introduced into the cell as RNA.

The invention also relates to a method for identifying a gene in a genome of a cell comprising the steps of: introducing a nucleic acid fragment and an SB protein into a cell, wherein the nucleic acid fragment comprises a nucleic acid sequence positioned between at least two inverted repeats into a cell wherein the inverted repeats can bind to the SB protein and wherein the nucleic acid fragment is capable of integrating into DNA in a cell in the presence of the SB protein; digesting the DNA of the cell with a restriction endonuclease capable of cleaving the nucleic acid sequence; identifying the inverted repeat sequences; sequencing the nucleic acid close to the inverted repeat sequences to obtain DNA sequence from an open reading frame; and comparing the DNA sequence with sequence information in a computer database. In one embodiment, the restriction endonuclease recognizes a 6-base recognition sequence. In another embodiment, the digesting step further comprises cloning the digested fragments or PCR amplifying the digested fragments.

The invention also relates to a stable transgenic vertebrate line comprising a gene operably linked to a promoter, wherein the gene and promoter are flanked by inverted repeats, wherein the inverted repeats can bind to an SB protein. In one embodiment, the SB protein comprises SEQ ID NO:1 or an amino acid sequence with at least 80% homology to SEQ ID NO:1. In one embodiment, the vertebrate is a fish, including a zebrafish and in another the vertebrate is a mouse.

In addition, the invention also relates to a protein with transposase activity that can bind to one or more of the following sequences: SEQ ID NO: 4, SEQ ID NO:5, SEQ ID NO:6, SEQ ID NO:7, SEQ ID NO:8, SEQ ID NO:9, and SEQ ID NO:10.

BRIEF DESCRIPTION OF THE FIGURES

FIGS. 1A+B illustrates the molecular reconstruction of a salmonid Tc1-like transposase gene. FIG. 1(A) is a schematic map of a salmonid TcE with the conserved domains in the transposase and IR/DR (inverted repeat/direct repeat) flanking sequences. FIG. 1(B) provides an exemplary strategy for constructing an open reading frame for a salmonid transposase (SB1–SB3) and then systematically introducing amino acid replacements into this gene (SB4–SB10). Amino acid residues are shown using single letter code at positions within the transposase polypeptide that were modified by site-specific mutagenesis, which are indicated with arrows. Translational termination codons appear as asterisks, frameshift mutations are shown as #. Residues changed to the consensus are check-marked and typed in italics. In the right margin, the various functional tests that were done at various stages of the reconstruction are indicated.

FIG. 2(A) is a nucleic acid sequence (SEQ ID NO:3) encoding the SB protein. FIG. 2(B) is the amino acid sequence (SEQ ID NO:1) of an SB transposase. The major functional domains are highlighted.

FIG. 3(A) provides the SDS-PAGE analysis illustrating the steps in the expression and purification of N123. Lanes: 1) extract of cells containing expression vector pET21a; 2) extract of cells containing expression vector pET21a/N123 before induction with IPTG; 3) extract of cells containing expression vector pET21a/ N123 after 2.5 h of induction with IPTG; 4) partially purified N123 using $Ni^{2+}$-NTA resin. Molecular weights in kDa are indicated on the right.

FIGS. 4A–C provides the DNase I footprinting of deoxyribonucleoprotein complexes formed by N123. FIG. 4(A) is a photograph of a DNase I footprinting gel containing a 500-fold dilution of the N123 preparation shown in lane 4 of FIG. 3A using the same transposon inverted repeat DNA probe as in FIG. 3B. Reactions were run in the absence (bottom lane) or presence (middle lane) of N123. Maxam-Gilbert sequencing of purine bases in the same DNA was used as a marker (lane 1). Reactions were run in the presence (lane 2) or absence (lane 3) of N123. FIG. 4(B) provides a sequence comparison (SEQ ID NOS:37–40) of the salmonid transposase-binding sites illustrated in Panel A with the corresponding sequences in the zebrafish Tdr1 elements. FIG. 4(C) is a sequence comparison (SEQ ID NOS:41–42) between the outer and internal transposase-binding sites in the SB transposons.

FIG. 5(A) is a schematic illustrating the genetic assay strategy for SB-mediated transgene integration in cultured cells.

FIG. 7(A) illustrates the results of a southern hybridization of HeLa cell genomic DNA with neomycin-specific radiolabeled probe from 8 individual HeLa cell clones that had been cotransfected with pT/neo and pSB10 and survived G-418 selection. Genomic DNA was digested with the restriction enzymes NheI, YhoI, BgII, SpeI and XbaI, enzymes that do not cut within the neo-marked transposon, prior to agarose gel electrophoresis and blotting.

FIGS. 10A+B illustrates a preferred screening strategy using IRS-PCR (interspersed repetitive sequence polymerase chain reaction). FIG. 10A illustrates a chromosomal region in the zebrafish genome containing the retroposon DANA (D) 5'-GGCGACRCAGTGGCGCAGTRGG (SEQ ID NO:13) and 5'-GAAYRTGCAAACTCCACACAGA (SEQ ID NO:14); Tdr1 transposons (T) 5'-TCCATCAGACCACAGGACAT (SEQ ID NO:15) and 5'-TGTCAGGAGGAATGGGCCAAAATTC (SEQ ID NO:16); and Angel (A) (a highly reiterated miniature inverted-repeat transposable element) 5'-TTTCAGTTTTGGGTGAACTATCC (SEQ ID NO:12) sequences. The arrows above the elements represent specific PCR primers.

The X superimposed on the central DANA element is meant to represent a missing element or a mutated primer binding site in the genome of another zebrafish strain. The various amplified sequence tagged sites (STSs) are identified by lowercase letter, beginning with the longest detectable PCR product. The products marked with an X are not produced in the PCR reaction if genomes with defective "X-DNA" are amplified. Elements separated by more than 3000 base pairs (bp) and elements having the wrong orientation relative to each other are not amplified efficiently. FIG. 10B is a schematic of the two sets of DNA amplification products from both genomes with (lane 1) and without (lane 2) the X'ed DANA element. Note that bands "a" and "d" are missing when the marked DANA sequence is not present.

DETAILED DESCRIPTION OF THE PREFERRED EMBODIMENTS

Figure 3A:
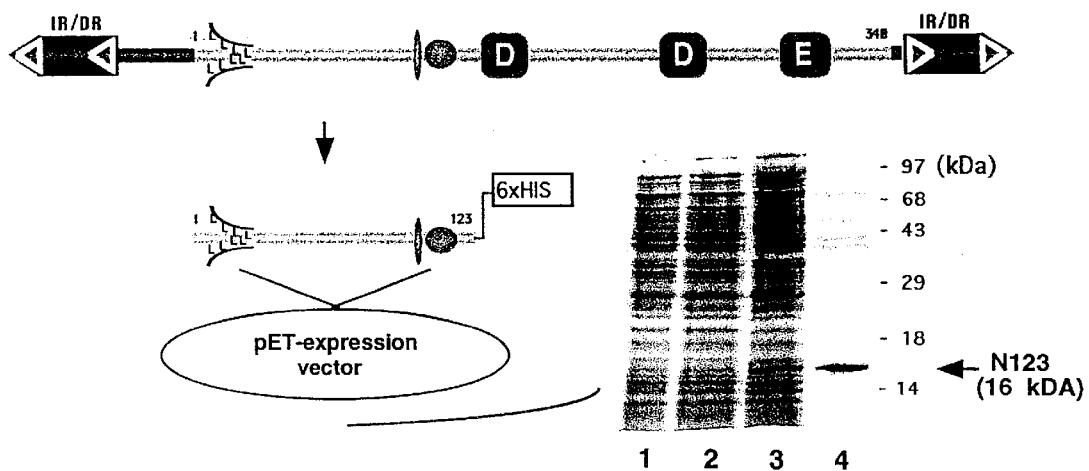
FIGS. 3A+B illustrates the DNA-binding activities of an N-terminal derivative of the SB transposase.

The present invention relates to novel tranposases and the transposon that are used to introduce nucleic acid sequences into the DNA of a cell. A transposase is an enzyme that is capable of binding to DNA at regions of DNA termed inverted repeats. Transposons typically contain at least one, and preferably two, inverted repeats that flank an intervening nucleic acid sequence. The transposase binds to recognition sites in the inverted repeats and catalyzes the incorporation of the transposon into DNA. Inverted repeats of an SB transposon can include two direct repeats and include at least one direct repeat.

Transposons are mobile, in that they can move from one position on DNA to a second position on DNA in the presence of a transposase. There are two fundamental components of any mobile cut-and-paste type transposon system, a source of an active transposase and the DNA sequences that are recognized and mobilized by the transposase. Mobilization of the DNA sequences permits the intervening nucleic acid between the recognized DNA sequences to also be mobilized.

DNA-transposons, including members of the Tc1/mariner superfamily, are ancient residents of vertebrate genomes (Radice et al., 1994; Smit and Riggs, 1996 Proc. Natl. Acad. Sci. USA 93, 1443–1448). However, neither autonomous copies of this class of transposon nor a single case of a spontaneous mutation caused by a TcE insertion have been proven in vertebrate animals. This is in contrast to retroposons whose phylogenetic histories of mutating genes in vertebrates is documented (Izsvak et al., 1997). Failure to isolate active DNA-transposons from vertebrates has greatly hindered ambitions to develop these elements as vectors for germline transformation and insertional mutagenesis. However, the apparent capability of salmonid TcEs for horizontal transmission between two teleost orders (Ivics et al., 1996) suggested that this particular subfamily of fish transposons might be transferred through even larger evolutionary distances.

Reconstructions of ancestral archetypal genes using parsimony analysis have been reported (Jermann et al., 1995. Nature 374, 57–59; Unnikrishnan et al., 1996, Stewart, 1995 Nature 374, 12–13). However, such a strategy requires vertical transmission of a gene through evolution for phylogenetically backtracking to the root sequence. Because parsimony analysis could not resolve the phylogenetic relationships between salmonid TcEs, we took the approach of reconstructing a consensus sequence from inactive elements belonging to the same subfamily of transposons. The resurrection of a functional promoter of the L1 retrotransposon in mouse (Adey et al., 1994 Proc. Natl. Acad. Sci. USA 91, 1569–1573) has previously been reported.

A strategy for obtaining an active gene is not without risks. The consensus sequence of transposase pseudogenes from a single organism may simply reflect the mutations that had occurred during vertical inactivation that have subsequently been fixed in the genome as a result of amplification of the mutated element. For instance, most Tdr1 elements isolated from zebrafish contain a conserved, 350-bp deletion in the transposase gene (Izsvak et al., 1995). Therefore, their consensus is expected to encode an inactive element. In contrast, because independent fixation of the same mutation in different species is unlikely, we derived a consensus from inactive elements of the same subfamily of transposons from several organisms to provide a sequence for an active transposon.

Both the transposase coding regions and the inverted repeats (IRs) of salmonid-type TcEs accumulated several mutations, including point mutations, deletions and insertions, and show about 5% average pairwise divergence (Ivics et al., 1996, supra). Example 1 describes the methods that were used to reconstruct a transposase gene of the salmonid subfamily of fish elements using the accumulated phylogenetic data. This analysis is provided in the EMBL database as DS30090 from FTP.EBI.AC.AK in directory/pub/databases/embl/align and the product of this analysis was a consensus sequence for an inactive SB protein. All the elements that were examined were inactive due to deletions and other mutations. A salmonid transposase gene of the SB transposase family was created using PCR-mutagenesis through the creation of 10 constructs as provided in FIG. 1 and described in Example 1.

This sequence can then be modified further, as described here, to produce active members of the SB protein family.

The SB protein recognizes inverted repeats on a nucleic acid fragment and each inverted repeat includes at least one direct repeat. The gene transfer system of this invention, therefore, comprises two components: a transposase and a cloned, nonautono mous (i.e., non-self inserting) salmonid-type element or transposon (referred to herein as a nucleic acid fragment having at least two inverted repeats) that carries the inverted repeats of the transposon substrate DNA. When put together these two components provide active transposon activity. In use, the transposase binds to the direct repeats in the inverted repeats and promotes integration of the intervening nucleic acid sequence into DNA of a cell a including chromosomes and extra chromosomal DNA of fish as well as mammalian cells. This transposon system does not appear to exist in nature.

The transposase that was reconstructed using the methods of Example 1 represents one member of a family of proteins that can bind to the inverted repeat region of a transposon to effect integration of the intervening nucleic acid sequence into DNA, preferably DNA in a cell. One example of the family of proteins of this invention is provided as SEQ ID NO:1 (see FIG. 2). This family of proteins is referred to herein as SB proteins. The proteins of this invention are provided as a schematic in FIG. 1. The proteins include, from the amino-terminus moving to the carboxy-terminus, a paired-like domain with leucine zipper, one or more nuclear localizing domains (NLS) domains and a catalytic domain including a DD(34)E box and a glycine-rich box as detailed in one example in FIG. 2. The SB family of proteins includes the protein having the amino acid sequence of SEQ ID NO: 1 and also includes proteins with an amino acid sequence that shares at least an 80% amino acid identity to SEQ ID NO:1. That is, when the proteins of the SB family are aligned, at least 80% of the amino acid sequence is identical. Proteins of the SB family are transposases, that is, they are able to catalyze the integration of nucleic acid into DNA of a cell. In addition, the proteins of this invention are able to bind to the inverted repeat sequences of SEQ ID NOS:4–5 and direct repeat sequences (SEQ ID NOS:6–9) from a transposon as well as a consensus direct repeat sequence (SEQ ID NO:10). The SB proteins preferably have a molecular weight range of about 35 kD to about 40 kD on about a 10% SDS-polyacrylamide gel.

To create an active SB protein, suitable for further modification, a number of chromosomal fragments were sequenced and identified by their homology to the zebrafish transposon-like sequence Tdr1, from eleven species of fish (Ivics et al., 1996). Next these and other homologous sequences were compiled and aligned. The sequences were identified in either GenBank or the EMBL database. Others have suggested using parsimony analysis to arrive at a consensus sequence but in this case parsimony analysis could not resolve the phylogenetic relationships among the salmonid-type TcEs that had been compiled. A consensus transposon was then engineered by changing selected nucleotides in codons to restore the amino acids that were likely to be in that position. This strategy assumes that the most common amino acid in a given position is probably the original (active) amino acid for that locus. The consensus sequence was examined for sites at which it appeared that C->T mutations had been fixed where deamination of $^{5m}C$ residues may have occurred (which leads to C being converted to T which in turn can lead to the "repair" of the mismatched G residue to an A). In these instances, the "majority-rule" consensus sequence was not always used. Next various expected activities of the resurrected transposase were tested to ensure the accuracy of the engineering.

The amino acid residues described herein employ either the single letter amino acid designator or the three-letter abbreviation. Abbreviations used herein are in keeping with the standard polypeptide nomenclature, *J. Biol. Chem.*, (1969), 243, 3552–3559. All amino acid residue sequences are represented herein by formulae with left and right orientation in the conventional direction of amino-terminus to carboxy-terminus.

Although particular amino acid sequences encoding the transposases of this invention have been described, there are a variety of conservative changes that can be made to the amino acid sequence of the SB protein without altering SB activity. These changes are termed conservative mutations, that is, an amino acid belonging to a grouping of amino acids having a particular size or characteristic can be substituted for another amino acid, particularly in regions of the protein that are not associated with catalytic activity or DNA binding activity, for example. Other amino acid sequences of the SB protein include amino acid sequences containing conservative changes that do not significantly alter the activity or binding characteristics of the resulting protein. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Particularly preferred conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free NH2.

The SB protein has catalytic activity in a cell but the protein can be introduced into a cell as protein or as nucleic acid. The SB protein can be introduced into the cell as ribonucleic acid, including mRNA; as DNA present in the cell as extrachromosomal DNA including, but not limited to, episomal DNA, as plasmid DNA, or as viral nucleic acid. Further, DNA encoding the SB protein can be stably integrated into the genome of the cell for constitutive or inducible expression. Where the SB protein is introduced into the cell as nucleic acid, the SB encoding sequence is preferably operably linked to a promoter. There are a variety of promoters that could be used including, but not limited to, constitutive promoters, tissue-specific promoters, inducible promoters, and the like. Promoters are regulatory signals that bind RNA polymerase in a cell to initiate transcription of a downstream (3' direction) coding sequence. A DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed and maintaining the correct reading frame to permit expression of the DNA sequence under the control of the expression control sequence to yield production of the desired protein product. One nucleic acid sequence encoding the SB protein is provided as SEQ ID NO:3. In addition to the conservative changes discussed above that would necessarily alter the SB-encoding nucleic acid sequence, there are other DNA or RNA sequences encoding SB protein that have the same amino acid sequence as an SB protein, but which take advantage of the degeneracy of the three letter codons used to specify a particular amino acid. For example, it is well known in the art that the following RNA codons (and therefore, the corresponding DNA codons, with a T substituted for a U) can be used interchangeably to code for each specific amino acid:

Phenylalanine (Phe or F)  UUU or UUC
Leucine (Leu or L)        UUA, UUG, CUU, CUC, CUA or CUG

| | -continued |
|---|---|
| Isoleucine (Ile or I) | AUU, AUC or AUA |
| Methionine (Met or M) | AUG |
| Valine (Val or V) | GUU, GUC, GUA, GUG |
| Serine (Ser or S) | UCU, UCC, UCA, UCG, AGU, AGC |
| Proline (Pro or P) | CCU, CCC, CCA, CCG |
| Threonine (Thr or T) | ACU, ACC, ACA, ACG |
| Alanine (Ala or A) | GCU, GCG, GCA, GCC |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU, CGC, CGA, CGG, AGA, AGC |
| Glycine (Gly or C) | GGU or GGC or GGA or GGG |
| Termination codon | UAA, UAG or UGA |

Further, a particular DNA sequence can be modified to employ the codons preferred for a particular cell type. For example, the preferred codon usage for *E. coli* is known, as are preferred codon usages for animals and humans. These changes are known to those of ordinary skill in the art and are therefore considered part of this invention.

Also contemplated in this invention are antibodies directed to an SB protein of this invention. An "antibody" for purposes of this invention is any immunoglobulin, including antibodies and fragments thereof that specifically binds to an SB protein. The antibodies can be polyclonal, monoclonal and chimeric antibodies. Various methods are known in the art that can be used for the production of polyclonal or monoclonal antibodies to SB protein. See, for example, *Antibodies: A Laboratory Manual*, Harlow and Lane, eds., Cold Spring Harbor Laboratory Press: Cold Spring Harbor, N.Y., 1988).

The nucleic acid encoding the SB protein can be introduced into a cell as a nucleic acid vector such as a plasmid, or as a gene expression vector, including a viral vector. The nucleic acid can be circular or linear. Methods for manipulating DNA and protein are known in the art and are explained in detail in the literature such as Sambrook et al, (1989) *Molecular Cloning: A Laboratory Manual.*, Cold Spring Harbor Laboratory Press or Ausubel, R. M., ed. (1994). *Current Protocols in Molecular Biology*. A vector, as used herein, refers to a plasmid, a viral vector or a cosmid that can incorporate nucleic acid encoding the SB protein or the nucleic acid fragment of this invention. The term "coding sequence" or "open reading frame" refers to a region of nucleic acid that can be transcribed and/or translated into a polypeptide in vivo when placed under the control of the appropriate regulatory sequences.

Another aspect of this invention relates to a nucleic acid fragment, sometimes referred to as a transposon or transposon element that includes a nucleic acid sequence positioned between at least two inverted repeats. Each inverted repeat preferably includes at least one direct repeat (hence, the name IR/DR). The transposon element is a linear nucleic acid fragment (extending from the 5' end to the 3' end, by convention) that can be used as a linear fragment or circularized, for example in a plasmid. In a preferred embodiment there are two direct repeats in each inverted repeat sequence. Preferred direct repeat sequences that bind to SB include:
The 5' outer repeat: (SEQ ID NO:6)
5'-GTTGAAGTCGGAAGTTTACATACACTTAAG-3'
The 5' inner repeat: (SEQ ID NO:7)
5'-CAGTGGGTCAGAAGTTTACATACACTAAGG-3'
The 3' inner repeat (SEQ ID NO:8)
5'-CAGTGGGTCAGAAGTTAACATACACTCAATT-3'
The 3' outer repeat (SEQ ID NO:9)
5'-AGTTGAAGTCGGAAGTTTACATACACCTTAG-3'.
A preferred consensus direct repeat is (SEQ ID NO:10)
5'-CA(GT)TG(AG)GTC(AG) GAAGTTTACATACACTTAAG-3'
In one embodiment the direct repeat sequence includes at least the following sequence:
ACATACAC (SEQ ID NO:11)
A preferred inverted repeat sequence of this invention is SEQ ID NO:4
and a second inverted repeat sequence of this invention is SEQ ID NO:5
Preferably the direct repeats are the portion of the inverted repeat that bind to the SB protein to permit insertion and integration of the nucleic acid fragment into the cell. The site of DNA integration for the SB proteins occurs at TA base pairs (see FIG. 7B).

The inverted repeats flank a nucleic acid sequence which is inserted into the DNA in a cell. The nucleic acid sequence can include all or part of an open reading from of a gene (i.e., that part of a gene encoding protein), one or more expression control sequences (i.e., regulatory regions in nucleic acid) alone or together with all or part of an open reading frame. Preferred expression control sequences include, but are not limited to promoters, enhancers, border control elements, locus-control regions or silencers. In a preferred embodiment, the nucleic acid sequence comprises a promoter operably linked to at least a portion of an open reading frame.

As illustrated in the examples, the combination of the nucleic acid fragment of this invention comprising a nucleic acid sequence positioned between at least two inverted repeats wherein the inverted repeats can bind to an SB protein and wherein the nucleic acid fragment is capable of integrating into DNA in a cell, in combination with an SB protein (or nucleic acid encoding the SB protein to deliver SB protein to a cell) results in the integration of the nucleic acid sequence into the cell. Alternatively, it is possible for the nucleic acid fragment of this invention to be incorporated into DNA in a cell through non-homologous recombination through a variety of as yet undefined, but reproducible mechanisms. In either event the nucleic acid fragment can be used for gene transfer.

As described in the examples, the SB family of proteins, mediates integration in a variety of cell types and a variety of species. The SB protein facilitates integration of the nucleic acid fragment of this invention with inverted repeats into both pluripotent (i.e., a cell whose descendants can differentiate into several restricted cell types, such as hematopoietic stem cells or other stem cells) and totipotent cells (i.e., a cell whose descendants can become any cell type in an organism, e.g., embryonic stem cells). It is likely that the gene transfer system of this invention can be used in a variety of cells including animal cells, bacteria, fungi (e.g., yeast) or plants. Animal cells can be vertebrate or invertebrate. Cells such as oocytes, eggs, and one or more cells of an embryo are also considered in this invention. Mature cells from a variety of organs or tissues can receive the nucleic acid fragment of this invention separately, alone, or together with the SB protein or nucleic acid encoding the SB protein. Cells receiving the nucleic acid fragment or the SB protein and capable of receiving the nucleic acid fragment into the DNA of that cell include, but are not limited to, lymphocytes, hepatocytes, neural cells, muscle cells, a variety of blood cells, and a variety of cells of an organism. Example 4 provides methods for determining whether a particular cell is amenable to gene transfer using this invention. The cells can be obtained from vertebrates or invertebrates. Preferred invertebrates include crustaceans or mollusks including, but not limited to shrimp, scallops, lobster, claims, or oysters.

Vertebrate cells also incorporate the nucleic acid fragment of this invention in the presence of the SB protein. Cells from fish, birds and other animals can be used, as can cells from mammals including, but not limited to, rodents, such as rats or mice, ungulates, such as cows or goats, sheep, swine or cells from a human.

The DNA of a cell that acts as a recipient of the nucleic acid fragment of this invention includes any DNA in contact with the nucleic acid fragment of this invention in the presence of an SB protein. For example, the DNA can be part of the cell genome or it can be extrachromosomal, such as an episome, a plasmid, a circular or linear DNA fragment. Targets for integration are double-stranded DNA.

The combination of the nucleic acid fragment of this invention including a nucleic acid sequence positioned between at least two inverted repeats wherein the inverted repeats can bind to an SB protein and wherein the nucleic acid fragment is capable of integrating into DNA of a cell in combination with a transposase or nucleic acid encoding a transposase, wherein the transposase is an SB protein, including SB proteins that include an amino acid sequence that is 80% identical to SEQ ID NO:1 is useful as a gene transfer system to introduce DNA into the DNA of a cell. In a preferred embodiment, the SB protein comprises the amino acid sequence of SEQ ID NO:1 and in another preferred embodiment the DNA encoding the transposase can hybridize to the DNA of SEQ ID NO:3 under the following hybridization conditions: in 30% (v/v) formamide in 0.5×SSC, 0.1% (w/v) SDS at 42° C. for 7 hours.

Gene transfer vectors for gene therapy can be broadly classified as viral vectors or non-viral vectors. The use of the nucleic acid fragment of this invention as a transposon in combination with an SB protein is a refinement of non-viral DNA-mediated gene transfer. Up to the present time, viral vectors have been found to be more efficient at introducing and expressing genes in cells. There are several reasons why non-viral gene transfer is superior to virus-mediated gene transfer for the development of new gene therapies. For example, adapting viruses as agents for gene therapy restricts genetic design to the constraints of that virus genome in terms of size, structure and regulation of expression. Non-viral vectors are generated largely from synthetic starting materials and are therefore more easily manufactured than viral vectors. Non-viral reagents are less likely to be immunogenic than viral agents making repeat administration possible. Non-viral vectors are more stable than viral vectors and therefore better suited for pharmaceutical formulation and application than are viral vectors.

Current non-viral gene transfer systems are not equipped to promote integration of nucleic acid into the DNA of a cell, including host chromosomes. As a result, stable gene transfer frequencies using non-viral systems have been very low; 0.1% at best in tissue culture cells and much less in primary cells and tissues. The present system is a non-viral gene transfer system that facilitates integration and markedly improves the frequency of stable gene transfer.

In the gene transfer system of this invention the SB protein can be introduced into the cell as a protein or as nucleic acid encoding the protein. In one embodiment the nucleic acid encoding the protein is RNA and in another, the nucleic acid is DNA. Further, nucleic acid encoding the SB protein can be incorporated into a cell through a viral vector, cationic lipid, or other standard transfection mechanisms including electroporation or particle bombardment used for eukaryotic cells. Following introduction of nucleic acid encoding SB, the nucleic acid fragment of this invention can be introduced into the same cell.

Similarly, the nucleic acid fragment can be introduced into the cell as a linear fragment or as a circularized fragment, preferably as a plasmid or as recombinant viral DNA. Preferably the nucleic acid sequence comprises at least a portion of an open reading frame to produce an amino-acid containing product. In a preferred embodiment the nucleic acid sequence encodes at least one protein and includes at least one promoter selected to direct expression of the open reading frame or coding region of the nucleic acid sequence. The protein encoded by the nucleic acid sequence can be any of a variety of recombinant proteins new or known in the art. In one embodiment the protein encoded by the nucleic acid sequence is a marker protein such as green fluorescent protein (GFP), chloramphenicol acetyltransferase (CAT), growth hormones, for example to promote growth in a transgenic animal, β-galactosidase (lacZ), luciferase (LUC), and insulin-like growth factors (IGFs).

In one embodiment of a transgenic animal, the protein is a product for isolation from a cell. Transgenic animals as bioreactors are known. Protein can be produced in quantity in milk, urine, blood or eggs. Promoters are known that promote expression in milk, urine, blood or eggs and these include, but are not limited to, casein promoter, the mouse urinary protein promoter, β-globin promoter and the ovalbumin promoter respectively. Recombinant growth hormone, recombinant insulin, and a variety of other recombinant proteins have been produced using other methods for producing protein in a cell. Nucleic acid encoding these or other proteins can be incorporated into the nucleic acid fragment of this invention and introduced into a cell. Efficient incorporation of the nucleic acid fragment into the DNA of a cell occurs when an SB protein is present. Where the cell is part of a tissue or part of a transgenic animal, large amounts of recombinant protein can be obtained. There are a variety of methods for producing transgenic animals for research or for protein production including, but not limited to (Hackett et al. (1993). The molecular biology of transgenic fish. In *Biochemistry and Molecular Biology of Fishes* (Hochachka & Mommsen, eds) Vol.2, pp. 207–240. Other methods for producing transgenic animals include the teachings of M. Markkula et al., *Rev. Reprod.*, 1, 97–106 (1996); R. T. Wall et al., *J. Dairy Sci.*, 80, 2213–2224 (1997); J. C. Dalton, et al., *Adv. Exp. Med. Biol.*, 411, 419–428 (1997); and H. Lubon et al., *Transfus. Med Rev.*, 10, 131–143 (1996). Transgenic zebrafish were made, as described in Example 6. The system has also been tested through the introduction of the nucleic acid with a marker protein into mouse embryonic stem cells (ES) and it is known that these cells can be used to produce transgenic mice (A. Bradley et al., *Nature,* 309, 255–256 (1984).

In general, there are two methods to achieve improved stocks of commercially important animals. The first is classical breeding, which has worked well for land animals, but it takes decades to make major changes. A review by Hackett et al. (1997) points out that by controlled breeding, growth rates in coho salmon (*Oncorhynchus kisutch*) increased 60% over four generations and body weights of two strains of channel catfish (*Ictalurus punctatus*) were increased 21 to 29% over three generations. The second method is genetic engineering, a selective process by which genes are introduced into the chromosomes of animals or plants to give these organisms a new trait or characteristic, like improved growth or greater resistance to disease. The results of genetic engineering have exceeded those of breeding in some cases. In a single generation, increases in body weight of 58% in common carp (*Cyprinus carpio*) with extra rainbow trout growth hormone I genes, more than 1000% in salmon with extra salmon growth hormone genes, and less in trout were obtained. The advantage of genetic engineering in fish, for example, is that an organism can be altered directly in a very short periods of time if the appropriate gene has been identified (see Hackett, 1997). The disadvantage of genetic engineering in fish is that few of the many genes that are involved in growth and development have been identified and the interactions of their protein products is poorly understood. Procedures for genetic manipulation are lacking many economically important animals. The present invention provides an efficient system for performing insertional mutagenesis (gene tagging) and efficient procedures for producing transgenic animals. Prior to this invention, transgenic DNA is not efficiently incorporated into chromosomes. Only about one in a million of the foreign DNA molecules integrates into the cellular genome, generally several cleavage cycles into development. Consequently, most transgenic animals are mosaic (Hackett, 1993). As a result, animals raised from embryos into which transgenic DNA has been delivered must be cultured until gametes can be assayed for the presence of integrated foreign DNA. Many transgenic animals fail to express the transgene due to position effects. A simple, reliable procedure that directs early integration of exogenous DNA into the chromosomes of animals at the one-cell stage is needed. The present system helps to fill this need.

The transposon system of this invention has applications to many areas of biotechnology. Development of transposable elements for vectors in animals permits the following: 1) efficient insertion of genetic material into animal chromosomes using the methods given in this application. 2) identification, isolation, and characterization of genes involved with growth and development through the use of transposons as insertional mutagens (e.g., see Kaiser et al., 1995, "Eukaryotic transposable elements as tools to study gene structure and function." In *Mobile Genetic Elements,* IRL Press, pp. 69–100). 3) identification, isolation and characterization of transcriptional regulatory sequences controlling growth and development. 4) use of marker constructs for quantitative trait loci (QTL) analysis. 5) identification of genetic loci of economically important traits, besides those for growth and development, i.e., disease resistance (e.g., Anderson et al., 1996, *Mol. Mar. Biol. Biotech.,* 5, 105–113). In one example, the system of this invention can be used to produce sterile transgenic fish. Broodstock with inactivated genes could be mated to produce sterile offspring for either biological ontainment or for maximizing growth rates in aquacultured fish.

In yet another use of the gene transfer system of this invention, the nucleic acid fragment is modified to incorporate a gene to provide a gene therapy to a cell. The gene is placed under the control of a tissue specific promoter or of a ubiquitous promoter or one or more other expression control regions for the expression of a gene in a cell in need of that gene. A variety of genes are being tested for a variety of gene therapies including, but not limited to, the CFTR gene for cystic fibrosis, adenosine deaminase (ADA) for immune system disorders, factor IX and interleukin-2 (IL-2) for blood cell diseases, alpha-1-antitrypsin for lung disease, and tumor necrosis factors (INFs) and multiple drug resistance (MDR) proteins for cancer therapies.

These and a variety of human or animal specific gene sequences including gene sequences to encode marker proteins and a variety of recombinant proteins are available in the known gene databases such as GenBank, and the like.

Further, the gene transfer system of this invention can be used as part of a process for working with or for screening a library of recombinant sequences, for example, to assess the function of the sequences or to screen for protein expression, or to assess the effect of a particular protein or a particular expression control region on a particular cell type. In this example, a library of recombinant sequences, such as the product of a combinatorial library or the product of gene shuffling, both techniques now known in the art and not the focus of this invention, can be incorporated into the nucleic acid fragment of this invention to produce a library of nucleic acid fragments with varying nucleic acid sequences positioned between constant inverted repeat sequences. The library is then introduced into cells together with the SB protein as discussed above.

An advantage of this system is that it is not limited to a great extent by the size of the intervening nucleic acid sequence positioned between the inverted repeats. The SB protein has been used to incorporate transposons ranging from 1.3 kilobases (kb) to about 5.0 kb and the mariner transposase has mobilized transposons up to about 13 kb. There is no known limit on the size of the nucleic acid sequence that can be incorporated into DNA of a cell using the SB protein.

Rather, what is limiting can be the method by which the gene transfer system of this invention is introduced into cells. For example, where microinjection is used, there is very little restraint on the size of the intervening sequence of the nucleic acid fragment of this invention. Similarly, lipid-mediated strategies do not have substantial size limitations. However, other strategies for introducing the gene transfer system into a cell, such as viral-mediated strategies could limit the length of the nucleic acid sequence positioned between the inverted repeats, according to this invention.

The two part SB transposon system can be delivered to cells via viruses, including retroviruses (including lentiviruses), adenoviruses, adeno-associated viruses, herpesviruses, and others. There are several potential combinations of delivery mechanisms for the transposon portion containing the transgene of interest flanked by the inverted terminal repeats (IRs) and the gene encoding the transposase. For example, both the transposon and the transposase gene can be contained together on the same recombinant viral genome; a single infection delivers both parts of the SB system such that expression of the transposase then directs cleavage of the transposon from the recombinant viral genome for subsequent integration into a cellular chromosome. In another example, the transposase and the transposon can be delivered separately by a combination of viruses and/or non-viral systems such as lipid-containing reagents. In these cases either the transposon and/or the transposase gene can be delivered by a recombinant virus. In every case, the expressed transposase gene directs liberation of the transposon from its carrier DNA (viral genome) for integration into chromosomal DNA.

This invention also relates to methods for using the gene transfer system of this invention. In one method, the invention relates to the introduction of a nucleic acid fragment comprising a nucleic acid sequence positioned between at least two inverted repeats into a cell. In a preferred embodiment, efficient incorporation of the nucleic acid fragment into the DNA of a cell occurs when the cell also contains an SB protein. As discussed above, the SB protein can be provided to the cell as SB protein or as nucleic acid encoding the SB protein. Nucleic acid encoding the SB protein can take the form of RNA or DNA. The protein can be introduced into the cell alone or in a vector, such as a plasmid or a viral vector. Further, the nucleic acid encoding the SB protein can be stably or transiently incorporated into the genome of the cell to facilitate temporary or prolonged expression of the SB protein in the cell. Further, promoters or other expression control regions can be operably linked with the nucleic acid encoding the SB protein to regulate expression of the protein in a quantitative or in a tissue-specific manner. As discussed above, the SB protein is a member of a family of SB proteins preferably having at least an 80% amino acid sequence identity to SEQ ID NO:1 and more preferably at least a 90% amino acid sequence identity to SEQ ID NO:1. Further, the SB protein contains a DNA-binding domain, a catalytic domain (having transposase activity) and an NLS signal.

The nucleic acid fragment of this invention is introduced into one or more cells using any of a variety of techniques known in the art such as, but not limited to, microinjection, combining the nucleic acid fragment with lipid vesicles, such as cationic lipid vesicles, particle bombardment, electroporation, DNA condensing reagents (e.g., calcium phosphate, polylysine or polyethyleneimine) or incorporating the nucleic acid fragment into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

The gene transfer system of this invention can readily be used to produce transgenic animals that carry a particular marker or express a particular protein in one or more cells of the animal. Methods for producing transgenic animals are known in the art and the incorporation of the gene transfer system of this invention into these techniques does not require undue experimentation. The examples provided below teach methods for creating transgenic fish by microinjecting the gene transfer system into a cell of an embryo of the fish. Further, the examples also describe a method for introducing the gene transfer system into mouse embryonic stem cells. Methods for producing transgenic mice from embryonic stem cells are well known in the art. Further a review of the production of biopharmaceutical proteins in the milk of transgenic dairy animals (see Young et al., BIO PHARM(1997), 10, 34–38) and the references provided therein detail methods and strategies for producing recombinant proteins in milk. The methods and the gene transfer system of this invention can be readily incorporated into these transgenic techniques without undue experimentation in view of what is known in the art and particularly in view of this disclosure.

The nucleic acid fragments of this invention in combination with the SB protein or nucleic acid encoding the SB protein is a powerful tool for germline transformation, for the production of transgenic animals, as methods for introducing nucleic acid into DNA in a cell, for insertional mutagenesis, and for gene tagging in a variety of species. Two strategies are diagramed in FIG. 9.

Due to their inherent ability to move from one chromosomal location to another within and between genomes, transposable elements have been exploited as genetic vectors for genetic manipulations in several organisms. Transposon tagging is a technique in which transposons are mobilized to "hop" into genes, thereby inactivating them by insertional mutagenesis. These methods are discussed by Evans et al., TIG 1997 13,370–374. In the process, the inactivated genes are "tagged" by the transposable element which then can be used to recover the mutated allele. The ability of the human and other genome projects to acquire gene sequence data has outpaced the ability of scientists to ascribe biological function to the new genes. Therefore, the present invention provides an efficient method for introducing a tag into the genome of a cell. Where the tag is inserted into a location in the cell that disrupts expression of a protein that is associated with a particular phenotype, expression of an altered phenotype in a cell containing the nucleic acid of this invention permits the association of a particular phenotype with a particular gene that has been disrupted by the nucleic acid fragment of this invention. Here the nucleic acid fragment functions as a tag. Primers designed to sequence the genomic DNA flanking the nucleic acid fragment of this invention can be used to obtain sequence information about the disrupted gene.

The nucleic acid fragment can also be used for gene discovery. In one example, the nucleic acid fragment in combination with the SB protein or nucleic acid encoding the SB protein is introduced into a cell. The nucleic acid fragment preferably comprises a nucleic acid sequence positioned between at least two inverted repeats, wherein the inverted repeats bind to the SB protein and wherein the nucleic acid fragment integrates into the DNA of the cell in the presence of the SB protein. In a preferred embodiment, the nucleic acid sequence includes a marker protein, such as GFP and a restriction endonuclease recognition site, preferably a 6-base recognition sequence. Following integration, the cell DNA is isolated and digested with the restriction endonuclease. Where a restriction endonuclease is used that employs a 6-base recognition sequence, the cell DNA is cut into about 4000-bp fragments on average. These fragments can be either cloned or linkers can be added to the ends of the digested fragments to provide complementary sequence for PCR primers. Where linkers are added, PCR reactions are used to amplify fragments using primers from the linkers and primers binding to the direct repeats of the inverted repeats in the nucleic acid fragment. The amplified fragments are then sequenced and the DNA flanking the direct repeats is used to search computer databases such as GenBank.

In another application of this invention, the invention provides a method for mobilizing a nucleic acid sequence in a cell. In this method the nucleic acid fragment of this invention is incorporated into DNA in a cell, as provided in the discussion above. Additional SB protein or nucleic acid encoding the SB protein is introduced into the cell and the protein is able to mobilize (i.e. move) the nucleic acid fragment from a first position within the DNA of the cell to a second position within the DNA of the cell. The DNA of the cell can be genomic DNA or extrachromosomal DNA. The method permits the movement of the nucleic acid fragment from one location in the genome to another location in the genome, or for example, from a plasmid in a cell to the genome of that cell.

All references, patents and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully practice the intended invention.

EXAMPLE 1

Reconstruction of an SB transposase

Recombinant DNA

Gene Reconstruction-Phase 1: Reconstruction of a Transposase Open Reading Frame

The Tss1.1 element from Atlantic salmon (GenBank accession number L12206) was PCR-amplified using a primer pair flanking the defective transposase gene, FTC-Start and FTC-Stop to yield product SB1. Next, a segment of the defective transposase gene of the Tss1.2 element (L12207) was PCR-amplified using PCQ primers FTC-3 and FTC-4, then further amplified with FTC-3 and FTC-5. The PCR product was digested with restriction enzymes NcoI and BlpI, underlined in the primer sequences, and cloned to replace the corresponding fragment in SB1 to yield SB2. Then, an approximately 250 bp HindIII fragment of the defective transposase gene of the Tsg1 element from rainbow trout (L12209) was isolated and cloned into the respective sites in SB2 to result in SB3. The Tss1 and Tsg1 elements were described in (Radice et al., 1994) and were kind gifts from S. W. Emmnons.

FTC-Start: 5'-CCTCTA<u>GGATCC</u>GACATCATG (SEQ ID NO:17)

FTC-Stop: 5'-TCTA<u>GAATTC</u>TAGTATTTGGTAGCATTG (SEQ ID NO:18)

FTC-3:5'-AACA<u>CCATGG</u>GACCACGCAGCCGTCA (SEQ ID NO:19)

FTC-4:5'-CAGGTTATGTCGATATAGGACTCGTTTTAC (SEQ ID NO:20)

FTC-5:5'-CCTT<u>GCTGAGC</u>GGCCTTTCAGGTTATGTCG (SEQ ID NO:21)

Gene Reconstruction-Phase 2: Site-specific PCR Mutagenesis of the SB3 Open Reading Frame to Introduce Consensus Amino Acid For PCR mutagenesis, two methods have been used: megaprimer PCR (Sarkar and Sommer, 1990 *BioTechniques* 8, 404–407) from SB4 through SB6, and Ligase Chain Reaction (Michael, 1994 *BioTechniques* 16, 410–412) for steps SB7 to SB10.

Oligonucleotide primers for product SB4 were the following:

FTC-7: 5'-TTGCACTTTTCGCACCAA for Gln->Arg(74) and Asn->Lys(75) (SEQ ID NO:22);

FTC-13: 5'-GTACCTGTTTCCTCCAGCATC for Ala->Glu (93) (SEQ ID NO:23);

FTC-8: 5'-GAGCAGTGGCTTCTTCCT for Leu->Pro(121) (SEQ ID NO:24);

FTC-9: 5'-CCACAACATGATGCTGCC for Leu->Met(193) (SEQ ID NO:25);

FTC-10: 5'-TGGCCACTCCAATACCTTGAC for Ala->Val (265) and Cys->Trp(268) (SEQ ID NO:26);

FTC-11: 5'-ACACTCTAGACTAGTATTTGGTAGCATTGCC for Ser->Ala(337) and Asn->Lys(339) (SEQ ID NO:27).

Oligonucleotide primers for product SB5:

B5-PTV: 5'-GTGCTTCACGGTTGGGATGGTG for Leu->Pro(183), Asn->Thr(184) and Met->Val(185) (SEQ ID NO:28).

Oligonucleotide primers for product SB6:

FTC-DDE: 5'-ATTTTCTATAGGATTGAGGTCAGGGC for Asp->Glu(279) (SEQ ID NO:29).

Oligonucleotide primers for products SB7 and SB8, in two steps:

PR-GAIS: 5'-GTCTGGTTCATCCTTGGGAGCAATTTCCAAAC GCC for Asn->Ile(28), His->Arg(31) and Phe->Ser(21) (SEQ ID NO:30).

Oligonucleotide primers for product SB9:

KARL: 5'-CAAAACCGACATAAGAAAGCCAGACTACGG for Pro->Arg(126) (SEQ ID NO:31);

RA: 5'-ACCATCGTTATGTTTGGAGGAAGAAGGGGGA GGCTTGCAAGCCG for Cys->Arg(166) and Thr->Ala (175) (SEQ ID NO:32);

EY: 5'-GGCATCATGAGGAAGGAAAATTATGTGGATAT ATTG for Lys->Glu(216) and Asp->Tyr(218) (SEQ ID NO:33);

KRV: 5'-CTGAAAAAGCGTGTGCGAGCAAGGAGGCC for Cys->Arg(288) (SEQ ID NO:34);

VEGYP: 5'-GTGGAAGGCTACCCGAAACGTTTGACC for Leu->Pro(324) (SEQ ID NO:35).

Oligonucleotide primers for product SB10.

FATAH: 5'-GACAAAGATCGTACTTTTTGGAGAAATGTC for Cys->Arg(143) (SEQ ID NO:36).

Plasmids. For pSB10, the SB10 transposase gene was cut with EcoRI and BamHI, whose recognition sequences are incorporated and underlined above in the primers FTC-Start and FTC-Stop, filled in with Klenow and cloned into the Klenow-filled NotI sites of CMV-βgal (Clonetech), replacing the LacZ gene originally present in this plasmid. Because of the blunt-end cloning, both orientations of the gene insert were possible to obtain and the antisense direction was used as a control for transposase. For pSB10-ΔDDE, plasmid pSB10 was cut with MscI, which removes 322 bp of the transposase coding region, and recircularized. Removal of the MscI fragment from the transposase gene deleted much of the catalytic DDE domain and disrupted the reading frame by introducing a premature translational termination codon.

Sequence alignment of 12 partial salmonid-type TcE sequences found in 8 fish species (available under DS30090 from FTP.EBI.AC.AK in directory/pub/databases/embl/ align from the EMBL database) allowed us to derive a majority-rule, salmonid-type consensus sequence, and identify conserved protein and DNA sequence motifs that likely have functional importance (FIG. 1A).

Conceptual translation of the mutated transposase open reading frames and comparison with functional motifs in other proteins allowed us to identify five regions that are highly conserved in the SB transposase family (FIG. 1A): I) a paired box/leucine zipper motif at the N-terminus; ii) a DNA-binding domain; iii) a bipartite nuclear localization signal (NLS); iv) a glycine-rich motif close to the center of the transposase without any known function at present; and v) a catalytic domain consisting of three segments in the C-terminal half comprising the DDE domain that catalyzes the transposition. DDE domains were identified by Doak et al. in Tc1 mariner sequences (Doak et al., 1994 *Proc. Natl. Acad. Sci. USA* 91, 942–946). Multiple sequence alignment also revealed a fairly random distribution of mutations in transposase coding sequences; 72% had occurred at non-synonymous positions in codons. The highest mutation frequencies were observed at CpG dinucleotide sites which are highly mutable (Adey et al., 1994, supra). Although amino acid substitutions were distributed throughout the transposases, fewer mutations were detected at the conserved motifs (0.07 non-synonymous mutations per codon), as compared to protein regions between the conserved domains (0.1 non-synonymous mutations per codon). This observation indicated to us that some selection mechanism had maintained the functional domains before inactivation of transposons took place in host genomes. The identification of these putative functional domains was of key importance during the reactivation procedure.

The first step of reactivating the transposase gene, was to restore an open reading frame (SB1 through SB3 in FIG. 1B) from bits and pieces of two inactive TcEs from Atlantic salmon (Salmo salar) and a single element from rainbow trout (Oncorhynchus mykiss) (Radice et al., 1994, supra). SB3, which has a complete open reading frame after removal of stop codons and frameshifts, was tested in an excision assay similar to that described by Handler et al. (1993) but no detectable activity was observed. Due to non-synonymous nucleotide substitutions, the SB3 polypeptide differs from the consensus transposase sequence in 24 positions (FIG. 1B) which can be sorted into two groups; nine residues that are probably essential for transposase activity because they are in the presumed functional domains and/or conserved in the entire Tc1 family, and another fifteen residues whose relative importance could not be predicted. Consequently, we undertook a dual gene reconstruction strategy. First, the putative functional protein domains of the transposase were systematically rebuilt one at a time by correcting the former group of mutations. Each domain for a biochemical activity was tested independently when possible. Second, in parallel with the first approach, a full-length, putative transposase gene was synthesized by extending the reconstruction procedure to all of the 24 mutant amino acids in the putative transposase.

Accordingly, a series of constructs was made to bring the coding sequence closer, step-by-step, to the consensus using PCR mutagenesis (SB4 through SB10 in FIG. 1B). As a general approach the sequence information predicted by the majority-rule consensus was followed. However, at some codons deamination of $^{5m}C$ residues of CpG sites occurred, and C->T mutations had been fixed in many elements. At R(288), where TpG's and CpG's were represented in equal numbers in the alignment, the CpG sequence was chosen because the CpG->TpG transition is more common in vertebrates than the TpG->CpG. The result of this extensive genetic engineering is a synthetic transposase gene encoding 340 amino acids (SB10 in FIGS. 1B and 2).

The reconstituted functional transposase domains were tested for activity. First, a short segment of the SB4 transposase gene (FIG. 1B) encoding an NLS-like protein motif was fused to the lacZ gene. The transposase NLS was able to mediate the transfer of the cytoplasmic marker-protein, β-galactosidase, into the nuclei of cultured mouse cells (Ivics et al., 1996, supra), supporting our predictions that a bipartite NLS was a functional motif in SB and that our approach to resurrect a full-length, multifunctional enzyme was viable.

EXAMPLE 2

Preparation of a Nucleic Acid Fragment with Inverted Repeat Sequences

In contrast to the prototypic Tc1 transposon from Caenorhabditis elegans which has short, 54-bp indirect repeat sequences (IRs) flanking its transposase gene, most TcEs in fish belong to the IR/DR subgroup of TcEs (Ivics et al., 1996; Izsvak et al., 1995, both supra) which have long, 210–250 bp IRs at their termini and directly repeated DNA sequence motifs (DRs) at the ends of each IR (FIG. 1A). However, the consensus IR sequences are not perfect repeats (i.e., similar, but not identical) indicating that, in contrast to most TcEs, these fish elements naturally possess imperfect inverted repeats. The match is less than 80% at the center of the IRs, but is perfect at the DRs, suggesting that this nonrandom distribution of dissimilarity could be the result of positive selection that has maintained functionally important sequence motifs in the IRs (FIG. 3). Therefore, we suspected that DNA sequences at and around the DRs might carry cis-acting information for transposition and mutations within the IRs, but outside the DRs, would probably not impair the ability of the element to transpose. As a model substrate, we chose a single salmonid-type TcE substrate sequence from Tanichthys albonubes (hereafter referred to as T) which has intact DR motifs whose sequences are only 3.8% divergent from the salmonid consensus. The variation in the DNase-protected regions of the four DR sequences varied from about 83% to about 95%, see SEQ ID NOS:6–9.

A TcE from Tanichthys albonubes (L48685) was cloned into the SmaI site of pUC 19 to result in pT. The donor construct for the integration assays, pT/neo, was made by cloning, after Klenow fill-in, an EcoRI/BamHI fragment of the plasmid pRc-CMV (Invitrogen, San Diego, Calif.) containing the SV40 promoter/enhancer, the neomycin resistance gene and an SV40 poly(A) signal into the StuI/MscI sites of pT. The StuI/MscI double digest of T leaves 352 bp on the left side and 372 bp on the right side of the transposon and thus contains the terminal inverted repeats. An EcoRI digest of pT/neo removed a 350 bp fragment including the left inverted repeat of the transposon, and this plasmid, designated pT/neo-ΔIR, was used as a control for the substrate-dependence of transposase-mediated transgene integration (see Example 4)

EXAMPLE 3

DNA Specificity of an SB Transposase

There are at least two distinct subfamilies of TcEs in the genomes of Atlantic salmon and zebrafish, Tss1/Tdr1 and Tss2/Tdr2, respectively. Elements from the same subfamily are more alike, having about 70% nucleic acid identity, even when they are from two different species (e.g., Tss1 and Tdr1) than members of two different subfamilies in the same species. For example, Tdr1 and Tdr2 are characteristically different in their encoded transposases and their inverted repeat sequences, and share only about 30% nucleic acid identity. It may be that certain subfamilies of transposons must be significantly different from each other in order to avoid cross-mobilization. A major question is whether substrate recognition of transposases is sufficiently specific to prevent activation of transposons of closely related subfamilies.

We have shown that the 12-bp DRs of salmonid-type elements, identical to the DRs of zebrafish-type TcEs, are part of the binding sites for SB. However, these binding-sites are 30 bp long. Thus, specific DNA-binding also involves DNA sequences around the DRs that are variable between TcE subfamilies in fish. Such a difference in the sequences of transposase binding sites might explain the inability of N123 to bind efficiently to zebrafish Tdr1 IRs, and may enable the transposase to distinguish even between closely related TcE subfamilies. Indeed, mutations of four base pairs in the 20-bp Tc1 binding site can abolish binding of transposase (Vos and Plasterk, 1994 EMBO J. 13, 6125–6132).

The DR core motifs are likely involved primarily in transposase-binding while sequences around the DR motifs likely provide the specificity for this binding.

SB has four binding-sites in its transposon substrate DNA that are located at the ends of the IRs. These sites share about a 83% to about a 95% identity (by comparison of SEQ ID NOS:6–9). However, a zebrafish Tdr1 element lacking an internal transposase-binding site was apparently able to transpose. This observation agrees with the finding that removal of internal transposase-binding sites from engineered Tc3 elements did not lessen their ability to transpose (Colloms et al., 1994 *Nucl. Acids Res.* 22, 5548–5554), suggesting that the presence of internal transposase-binding sites is not essential for transposition. Multiple binding-sites for proteins, including transposases, are frequently associated with regulatory functions (Gierl et al., 1988 *EMBO J.* 7, 4045–4053). Consequently, the internal binding-sites for transposases in the IR/DR group of TcEs serve one or more regulatory purposes affecting transposition and/or gene expression.

Once in the nucleus, a transposase must bind specifically to its recognition sequences in the transposon. The specific DNA-binding domains of both the Tc1 and Tc3 transposases have been mapped to their N-terminal regions (Colloms et al., 1994, supra; Vos and Plasterk, 1994, supra). However, there is very little sequence conservation between the N-terminal regions of TcE transposases, suggesting that these sequences are likely to encode specific DNA-binding functions in these proteins. On the other hand, the N-terminal region of SB has significant structural and sequence similarities to the paired DNA-binding domain, found in the Pax family of transcription factors, in a novel combination with a leucine zipper-like motif (Ivics et al., 1996, supra). A gene segment encoding the first 123 amino acids of SB (N123), which presumably contains all the necessary information for specific DNA-binding and includes the NLS, was reconstructed (SB8 in FIG. 1B), and expressed in *E coli*. N123 was purified via a C-terminal histidine tag as a 16 KDa polypeptide (FIG. 3A).

Induction of N123 was in *E. coli* strain BL21 (DE3) (Novagen) by the addition of 0.4 mM IPTG at 0.5 O.D. at 600 mn and continued for 2.5 h at 30° C. Cells were sonicated in 25 mM HEPES, pH 7.5, 1 M NaCl, 15% glycerol, 0.25% Tween 20,2 mM β-mercaptoethanol, 1 mM PMSF) and 10 mM imidazole (pH 8.0) was added to the soluble fraction before it was mixed with $Ni^{2+}$-NTA resin (Qiagen) according to the recommendations of the manufacturer. The resin was washed with 25 mM HEPES (pH 7.5), 1 M NaCl, 30% glycerol, 0.25% Tween 20, 2 mM β-mercaptoethanol, 1 mM PMSF and 50 mM imidazole (pH 8.0) and bound proteins were eluted with sonication buffer containing 300 mM imidazole, and dialyzed overnight at 4° C. against sonication buffer without imidazole.

Figure 3B:
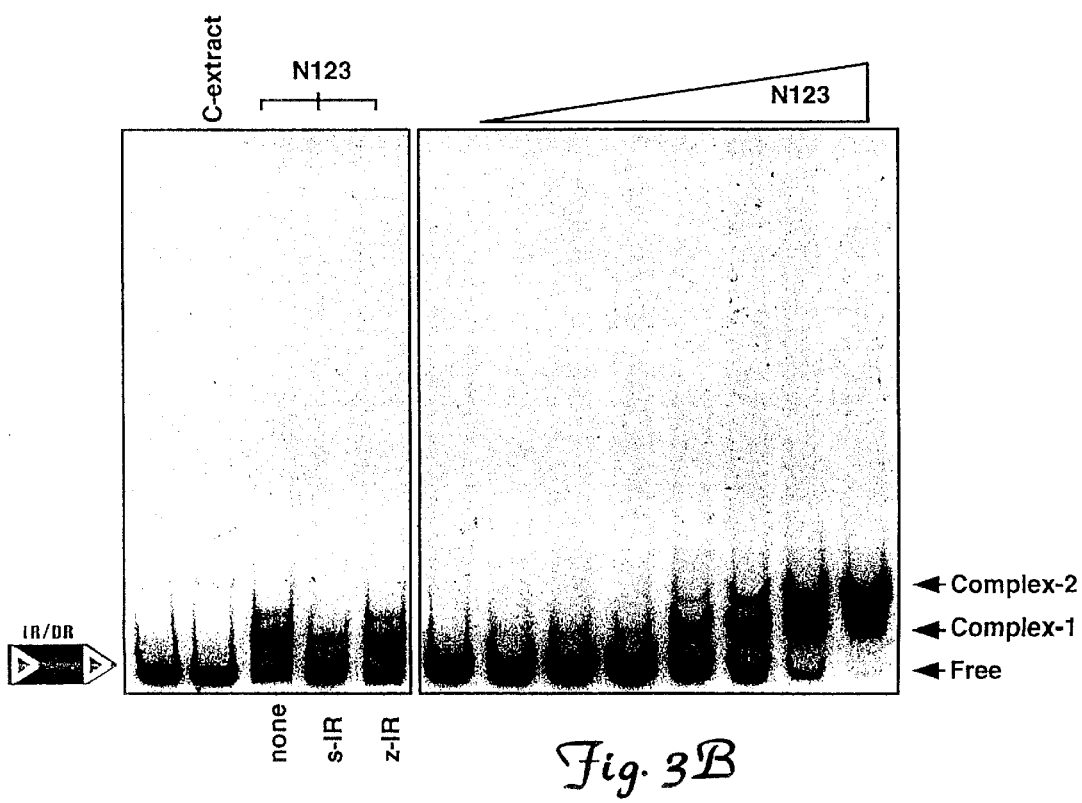
FIG. 3(B) illustrates the results of mobility-shift analysis studies to determine whether N123 bound to the inverted repeats of fish transposons. Lanes: 1) probe only; 2) extract of cells containing expression vector pET21a; 3) 10,000-fold dilution of the N123 preparation shown in lane 4 of Panel A; 4) same as lane 3 plus a 1000-fold molar excess of unlabelled probe as competitor DNA; 5) same as lane 3 plus a 1000-fold molar excess of an inverted repeat fragment of a zebrafish Tdr1 element as competitor DNA; 6–13) 200,000-, 100,000-, 50,000-, 20,000-, 10,000-, 5,000-, 2,500-, and 1,000-fold dilutions of the N123 preparation shown in lane 4 of Panel A.

In addition to the NLS function, N123 also contains the specific DNA-binding domain of SB, as tested in a mobility-shift assay (FIG. 3B). A 300 bp EcoRI/HindIII fragment of pT comprising the left inverted repeat of the element was end-labeled using [$\alpha^{32}$P]dCTP and Klenow. Nucleoprotein complexes were formed in 20 mM HEPES (pH 7.5), 0.1 mM EDTA, 0.1 mg/ml BSA, 150 mM NaCl, 1 mM DTT in a total volume of 10 μl. Reactions contained 100 pg labeled probe, 2 μg poly[dI][dC] and 1.5 μl N123. After 15 min incubation on ice, 5 μl of loading dye containing 50% glycerol and bromophenol blue was added and the samples loaded onto a 5% polyacrylamide gel (Ausubel). DNaseI footprinting was done using a kit from BRL according to the recommendations of the manufacturer. Upon incubation of a radiolabeled 300-bp DNA fragment comprising the left IR of T, deoxyribonucleoprotein complexes were observed (FIG. 3B, left panel-lane 3), as compared to samples containing extracts of bacteria transformed with the expression vector only (lane 2) or probe without any protein (lane 1). Unlabelled IR sequences of T, added in excess to the reaction as competitor DNA, inhibited binding of the probe (lane 4), whereas the analogous region of a cloned Tdr1 element from zebrafish did not appreciably compete with binding (lane 5). Thus, N123 is able to distinguish between salmonid-type and zebrafish-type TcE substrates.

The number of the deoxyribonucleoprotein complexes detected by the mobility-shift assay at increasingly higher N123 concentrations indicated two protein molecules bound per IR (FIG. 3B, right panel), consistent with either two binding sites for transposase within the IR or a transposase dimer bound to a single site. Transposase-binding sites were further analyzed and mapped in a DNaseI footprinting experiment. Using the same fragment of T as above, two protected regions close to the ends of the IR probe were observed (FIG. 4). The two 30-bp footprints cover the subterminal DR motifs within the IRs. Thus, the DRs are the core sequences for DNA-binding by N123. The DR motifs are almost identical between salmonid- and zebrafish-type TcEs (Ivics et al., 1997). However, the 30-bp transposase binding-sites are longer than the DR motifs and contain 8 base pairs and 7 base pairs in the outer and internal binding sites, respectively, that are different between the zebrafish- and the salmonid-type IRs (FIG. 4B).

Although there are two binding-sites for transposase near the ends of each IR, apparently only the outer sites are utilized for DNA cleavage and thus excision of the transposon. Sequence comparison shows that there is a 3-bp difference in composition and a 2-bp difference in length between the outer and internal transposase-binding sites (FIG. 4C). In summary, our synthetic transposase protein has DNA-binding activity and this binding appears to be specific for salmonid-type IR/DR sequences.

For the expression of an N-terminal derivative of SB transposase, a gene segment of SB8 was PCR-amplified using primers FTC-Start and FTC-8, 5'-phosphorylated with T4 polynucleotide kinase, digested with BamHI, filled in with Klenow, and cloned into the NdeI/EcoRI digested expression vector pET21a (Novagen) after Klenow fill-in. This plasmid, pET21a/N123 expresses the first 123 amino acids of the transposase (N123) with a C-terminal histidine tag.

EXAMPLE 4

Transposition of DNA by an SB Transposase

The following experiments demonstrate that the synthetic, salmonid-type SB transposase performed all of the complex steps of transposition, i.e., recognized a DNA molecule, excised the substrate DNA and inserted it into the DNA of a cell, such as a cell chromosome. This is in contrast to control samples that did not include the SB transposase and therefore measured integration through non-homologous recombination.

Figure 7A:
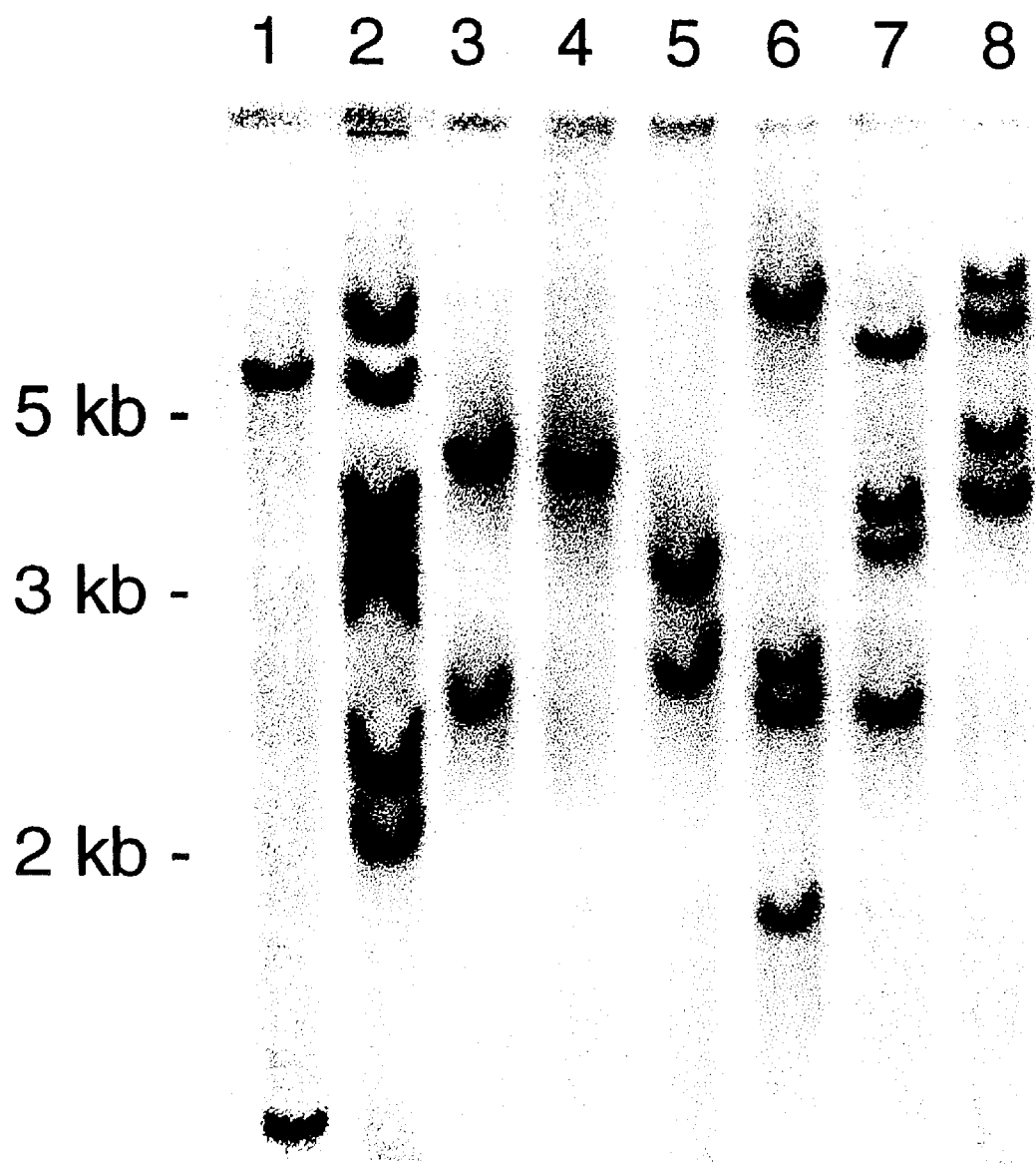
FIGS. 7A+B illustrates the integration of neomycin resistance-marked transposons into the chromosomes of HeLa cells.

Upon cotransfection of the two-component SB transposon system into cultured vertebrate cells, transposase activity manifested as enhanced integration of the transgene serving as the DNA substrate for transposase. The binding of transposase to a donor construct and subsequent active transport of these nucleoprotein complexes into the nuclei of transfected cells could have resulted in elevated integration rates, as observed for transgenic zebrafish embryos using an SV40 NLS peptide (Collas et al., 1996 *Transgenic Res.* 5, 451–458). However, DNA-binding and nuclear targeting activities alone did not increase transformation frequency, which occurred only in the presence of full-length transposase. Although not sufficient, these functions are probably necessary for transposase activity. Indeed, a single amino acid replacement in the NLS of mariner is detrimental to overall transposase function (Lohe et al., 1997 *Proc. Natl. Acad. Sci. USA* 94, 1293–1297). The inability of SB6, a mutated version of the transposase gene, to catalyze transposition demonstrates the importance of the sequences of the conserved motifs. Notably, three of the 11 amino acid substitutions that SB6 contains, F(21), N(28) and H(31) are within the specific DNA-binding domain (FIGS. 1 and 2). Sequence analysis of the paired-like DNA-binding domain of fish TcE transposases indicates that an isoleucine at position 28 is conserved between the transposases and the corresponding positions in the Pax proteins (Ivics et al., 1996, supra). Thus, we predict that this motif is crucial for DNA-binding activity. SB exhibits substrate-dependence for specific recognition and integration; only those engineered transposons that have both of the terminal inverted repeats can be transposed by SB. Similarly, in P element transformation in Drosophila, the transposase-producing helper construct is often a "wings-clipped" transposase gene which lacks one of the inverted repeats of P which prevents the element from jumping (Cooley et al., 1988 *Science* 239, 1121–1128). In our transient assay, transposition can only occur if both components of the SB system are present in the same cell. Once that happens, multiple integrations can take place as demonstrated by our finding of up to 11 integrated transgenes in neomycin-resistant cell clones (FIG. 7A). In contrast to spontaneous integration of plasmid DNA in cultured mammalian cells that often occurs in the form of concatemeric multimers into a single genomic site (Perucho et al., 1980 *Cell* 22, 309–317), these multiple insertions appear to have occurred in distinct chromosomal locations.

Integration of our synthetic, salmonid transposons was observed in fish as well as in mouse and human cells. In addition, recombination of genetic markers in a plasmid-to-plasmid transposition assay (Lampe et al., 1996, supra) was significantly enhanced in microinjected zebrafish embryos in the presence of transposase. Consequently, SB apparently does not need any obvious, species-specific factor that would restrict its activity to its original host. Importantly, the most significant enhancement, about 20-fold, of transgene integration was observed in human cells as well as fish embryonic cells.

Integration Activity of SB

In addition to the abilities to enter nuclei and specifically bind to its sites of action within the inverted repeats, a fully active transposase is expected to excise and integrate transposons. In the C-terminal half of the SB transposase, three protein motifs make up the DD(34)E catalytic domain; the two invariable aspartic acid residues, D(153) and D(244), and a glutamic acid residue, E(279), the latter two being separated by 34 amino acids (FIG. 2). An intact DD(34)E box is essential for catalytic functions of Tc1 and Tc3 transposases (van Luenen et al., 1994 *Cell* 79, 293–301; Vos and Plasterk, 1994, supra).

Figure 5A:
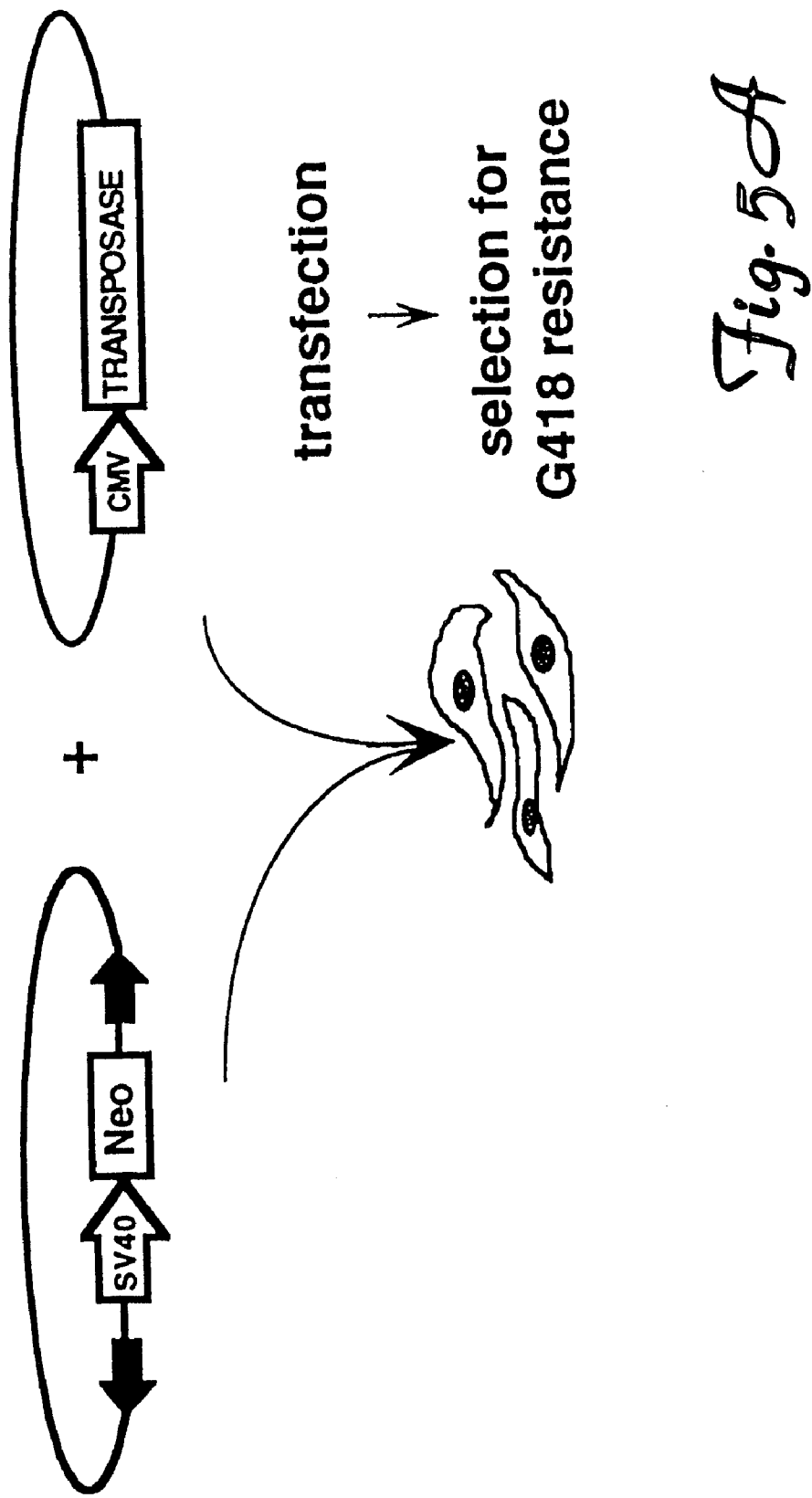
FIGS. 5A+B illustrates the integration activity of SB in human HeLa cells.
Figure 5B:
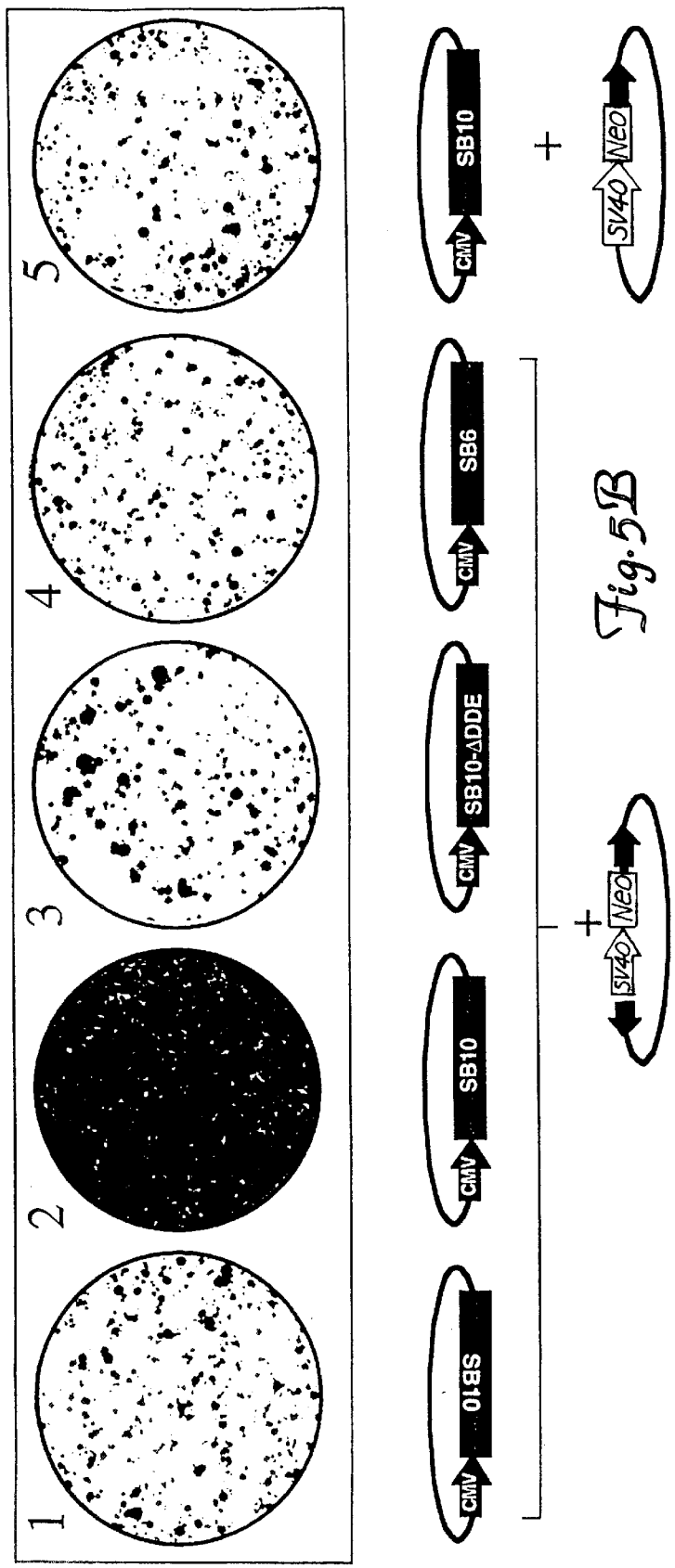
FIG. 5(B) demonstrates HeLa cell integration using Petri dishes of HeLa cells with stained colonies of G-418-resistant HeLa cells that were transfected with different combinations of donor and helper plasmids. Plate: 1) pT/neo plus pSB10-AS; 2) pT/neo plus pSB10; 3) pT/neo plus pSB 10-ΔDDE; 4) pT/neo plus pSB6; 5) pT/neo-ΔIR plus pSB10.
Figure 6:
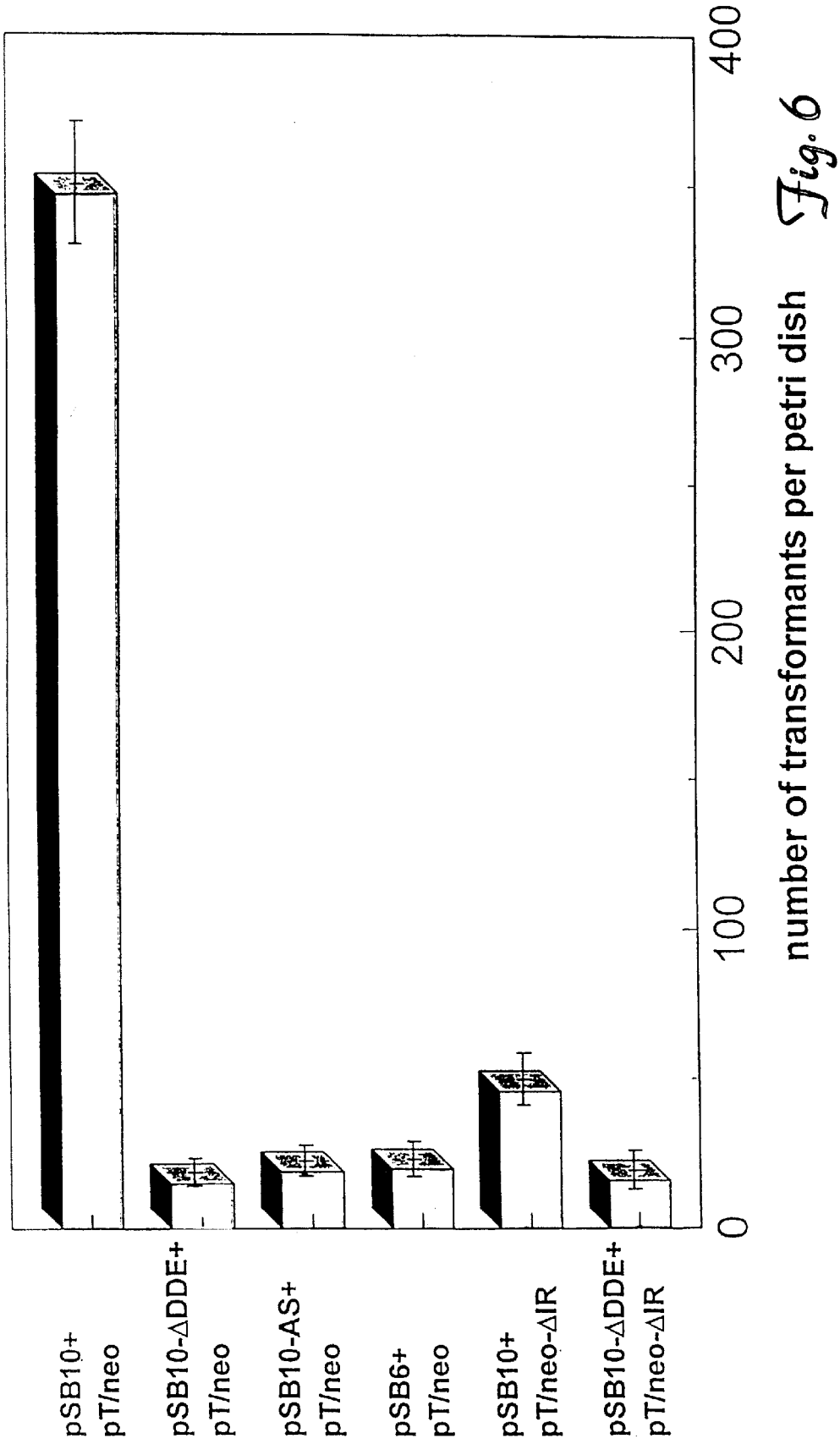
FIG. 6 summarizes the results of transgene integration in human HeLa cells. Integration was dependent on the presence of an active SB transposase and a transgene flanked by transposon inverted repeats. Different combinations of the indicated donor and helper plasmids were cotransfected into cultured HeLa cells and one tenth of the cells, as compared to the experiments shown in FIG. 5, were plated under selection to count transformants. The efficiency of transgene integration was scored as the number of transformants surviving antibiotic selection. Numbers of transformants at right represent the numbers of G418-resistant cell colonies per dish. Each number represents the average obtained from three transfection experiments.

Two different integration assays were used. A first assay was designed to detect chromosomal integration events into the chromosomes of cultured cells. The assay is based on trans-complementation of two nonautonomous transposable elements, one containing a selectable marker gene (donor) and another that expresses the transposase (helper) (FIG. 5A). The donor, pT/neo, is an engineered, T-based element which contains an SV40 promoter-driven neo gene flanked by the terminal IRs of the transposon containing binding sites for the transposase. The helper construct expresses the full-length SB10 transposase gene driven by a human cytomegalovirus (CMV) enhancer/promoter. In the assay, the donor plasmid is cotransfected with the helper or control constructs into cultured vertebrate cells, and the number of cell clones that are resistant to the neomycin analog drug G-418 due to chromosomal integration and expression of the neo transgene serves as an indicator of the efficiency of gene transfer. If SB is not strictly host-specific, transposition should also occur in phylogenetically distant vertebrate species. Using the assay system shown in FIG. 5A, enhanced levels of transgene integration were observed in the presence of the helper plasmid; more than 5-fold in mouse LMTK cells and more than 20-fold in human HeLa cells (FIGS. 5B and 6). Consequently, SB appears to be able to increase the efficiency of transgene integration, and this activity is not restricted to fish cells.

To analyze the requirements for enhanced transgene integration, further experiments were conducted. FIG. 5B shows five plates of transfected HeLa cells that were placed under G-418 selection, and were stained with methylene blue two weeks post-transfection. The staining patterns clearly demonstrate a significant increase in integration of neo-marked transposons into the chromosomes of HeLa cells when the SB transposase-expressing helper construct was cotransfected (plate 2), as compared to a control cotransfection of the donor plasmid plus the SB transposase gene cloned in an antisense orientation (pSB10-AS; plate 1). This result indicates that the production of transposase protein was essential for enhanced chromosomal integration of the transgene and demonstrates that the transposase is precise even in human cells.

Figure 8:
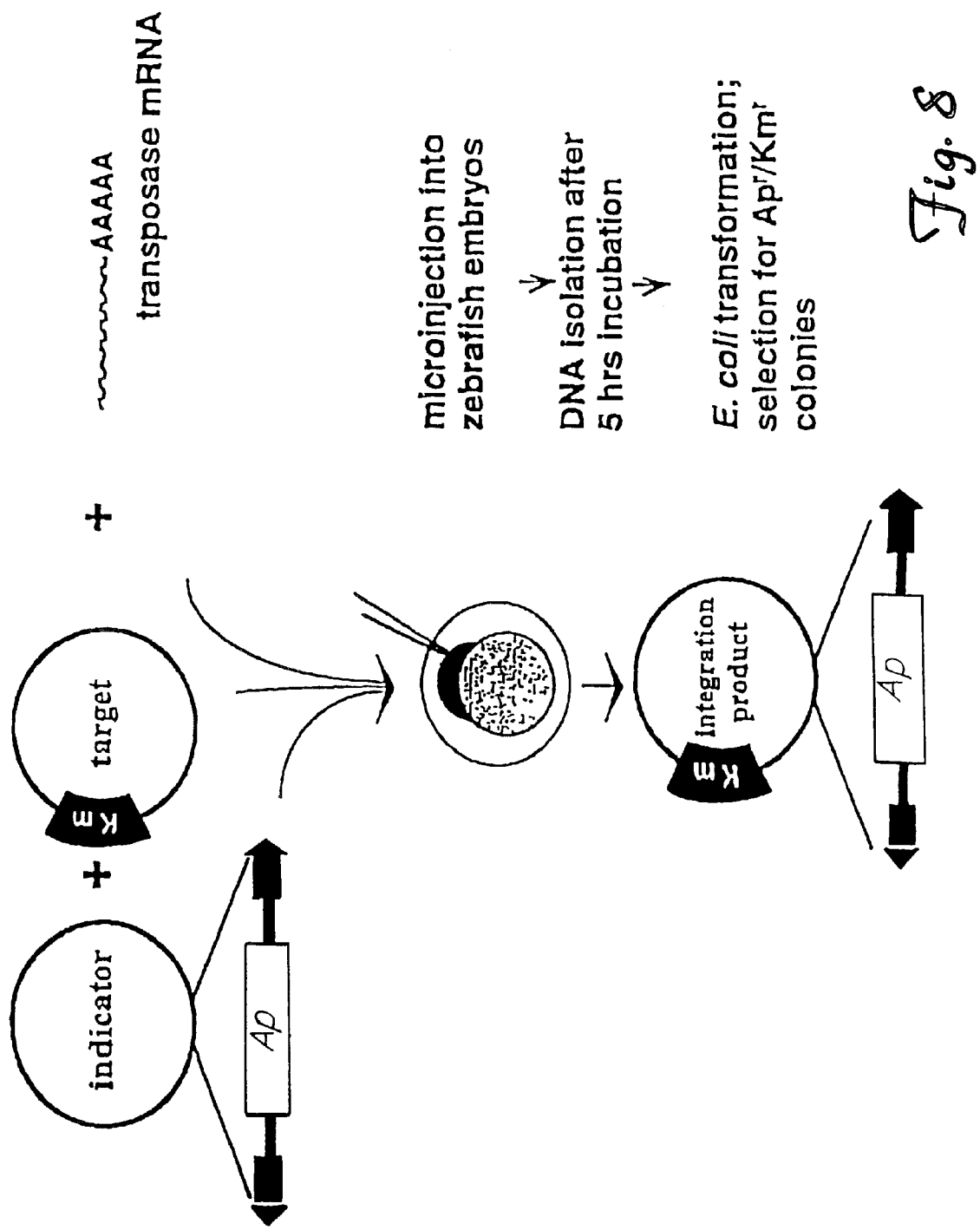
FIG. 8 is a schematic demonstrating an interplasmid assay for excision and integration of a transposon. The assay was used to evaluate transposase activity in zebrafish embryos. Two plasmids plus an RNA encoding an SB transposase protein were coinjected into the one-cell zebrafish embryo. One of the plasmids had an ampicillin resistance gene (Ap) flanked by IR/DR sequences recognizable by the SB transposase. Five hours after fertilization and injection, low molecular weight DNA was isolated from the embryos and used to transform *E. coli*. The bacteria were grown on media containing ampicillin and kanamycin (Km) to select for bacteria harboring single plasmids containing both the Km and Ap antibiotic-resistance markers. The plasmids from doubly resistant cells were examined to confirm that the Ap-transposon was excised and reintegrated into the Km target plasmid. Ap-transposons that moved into either another indicator Ap-plasmid or into the zebrafish genome were not scored. Because the amount of DNA in injected plasmid was almost equal to that of the genome, the number of integrations of Ap-transposons into target plasmids approximated the number of integrations into the genome.

In a second assay, an indicator plasmid containing the transposase recognition sequence and a marker gene (Ampicillin resistance) was co-injected with a target plasmid containing a kanamycin gene and SB transposase. Resulting plasmids were isolated and used to transform *E. coli*. Colonies were selected for ampicillin and kanamycin resistance (see FIG. 8). While SB transposase was co-microinjected in these assays, mRNA encoding the SB transposase could also be co-microinjected in place of or in addition to, the SB transposase protein.

Cell Transfections

Cells were cultured in DMEM supplemented with 10% fetal bovine serum, seeded onto 6 cm plates one day prior to transfection and transfected with 5 $\mu$g Elutip (Schleicher and Schuell)-purified plasmid DNA using Lipofectin from BRL. After 5 hrs of incubation with the DNA-lipid complexes, the cells were "glycerol-shocked" for 30 sec with 15% glycerol in phosphate buffered saline (PBS), washed once with PBS and then refed with serum-containing medium. Two days post-transfection, the transfected cells were trypsinized, resuspended in 2 ml of serum-containing DMEM and either 1 ml or 0.1 ml aliquots of this cell suspension were seeded onto several 10 cm plates in medium containing 600 $\mu$g/ml G-418 (BRL). After two weeks of selection, cell clones were either picked and expanded into individual cultures or fixed with 10% formaldehyde in PBS for 15 min, stained with methylene blue in PBS for 30 min, washed extensively with deionized water, air dried and photographed.

These assays can also be used to map transposase domains necessary for chromosomal integration. For this assay, a frameshift mutation was introduced into the SB transposase gene which put a translational stop codon behind G(161). This construct, pSB10-ΔDDE, expresses a truncated transposase polypeptide that contains specific DNA-binding and NLS domains, but lacks the catalytic domain. The transformation rates obtained using this construct (plate 3 in FIG. 5B) were similar to those obtained with the antisense control (FIG. 6). This result suggests that the presence of a full-length transposase protein is necessary and that DNA-binding and nuclear transport activities themselves are not sufficient for the observed enhancement of transgene integration.

As a further control of transposase requirement, the integration activity of an earlier version of the SB transposase gene was tested, SB6 which differs from SB10 at 11 residues, FIG. 1B), using the same assay. The number of transformants observed using SB6 (plate 4 in FIG. 5B) was about the same as with the antisense control experiment (FIG. 6), indicating that the amino acid replacements that we introduced into the transposase gene were critical for transposase function. In summary, the three controls shown in plates 1, 3, and 4 of FIG. 5B establish the trans-requirements of enhanced, SB-mediated transgene integration.

True transposition requires a transposon with intact IR sequences. One of the IRs of the neo-marked transposon substrate was removed, and the performance of this construct, pT/neo-ΔIR, was tested for integration. The transformation rates observed with this plasmid (plate 5 in FIG. 5B) were more than 7-fold lower than those with the full-length donor (FIG. 6). These results indicated that both of the IRs flanking the transposon are required for efficient transposition and thereby establish some of the cis-requirements of the two-component SB transposon system.

To examine the structures of integrated transgenes, eleven colonies of cells growing under G-418 selection from an experiment similar to that shown in plate 2 in FIG. 5B were picked and their DNAs analyzed using Southern hybridization. Genomic DNA samples of the cell clones were digested with a combination of five restriction enzymes that do not cut within the 2233 bp T/neo marker transposon, and hybridized with a neo-specific probe (FIG. 7). The hybridization patterns indicated that all of the analyzed clones contained integrated transgenes in the range of 1 (lane 4) to 11 (lane 2) copies per transformant. Moreover, many of the multiple insertions appear to have occurred in different locations in the human genome.

Figure 7B:
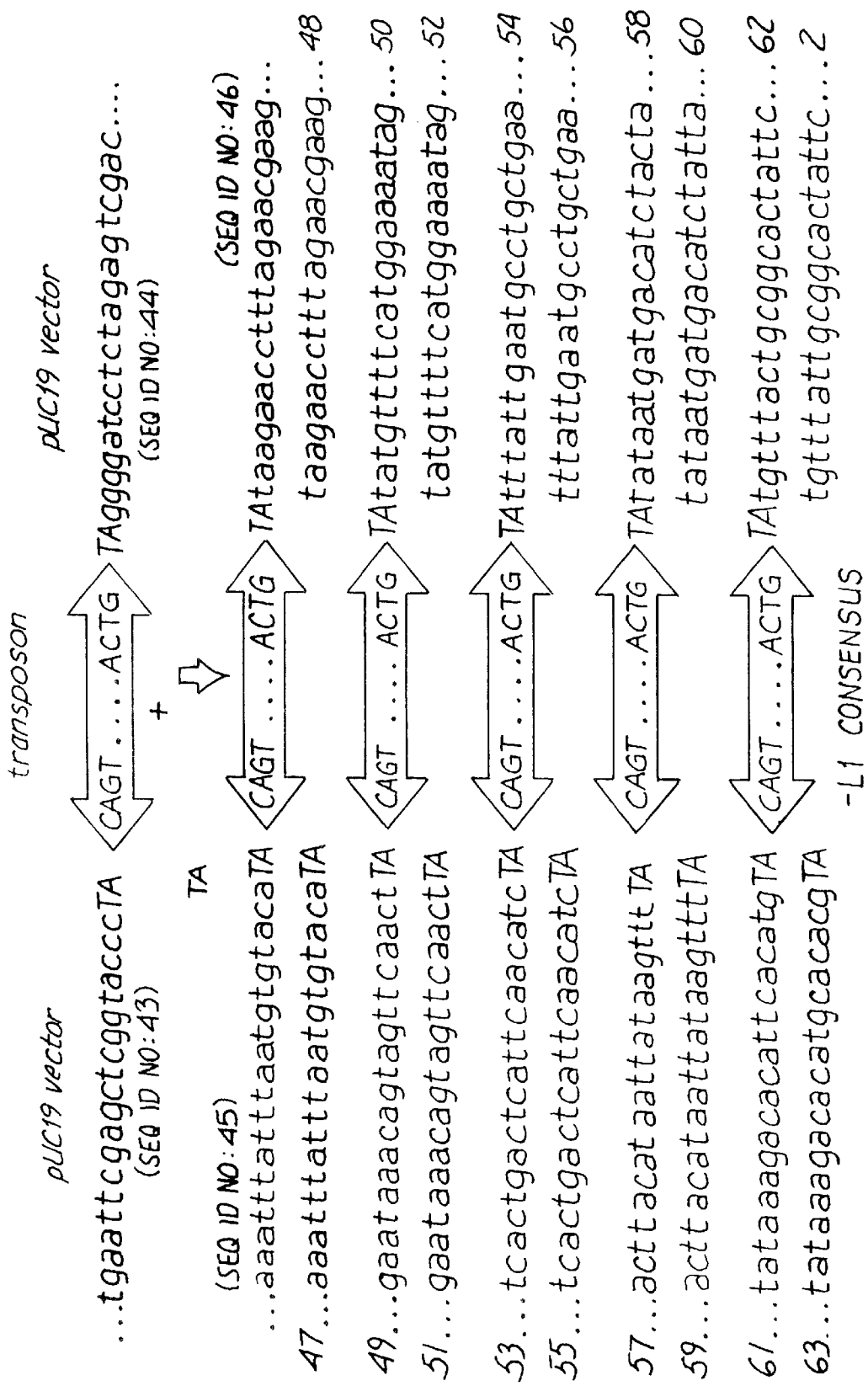
FIG. 7(B) is a diagram of the junction sequences (SEQ ID NOS:43–63 and SEQ ID NO:2) of T/neo transposons integrated into human genomic DNA. The donor site is illustrated on top with plasmid vector sequences that originally flanked the transposon in pT/neo (arrows). IR sequences are boxed in the arrows.

The presence of duplicated TA sequences flanking an integrated transposon is a hallmark of TcE transposition. To reveal such sequences, junction fragments of integrated transposons and human genomic DNA were isolated using a ligation-mediated PCR assay (Devon et al., *Nucl. Acids. Res.*, 23, 1644–1645 (1995)). We have cloned and sequenced junction fragments of five integrated transposons, all of them showing the predicted sequences of the IRs which continue with TA dinucleotides and sequences that are different in all of the junctions and different from the plasmid vector sequences originally flanking the transposon in pT/neo (FIG. 7B). The same results were obtained from nine additional junctions containing either the left or the right IR of the transposon (data not shown). These results indicated that the marker transposons had been precisely excised from the donor plasmids and subsequently spliced into various locations in human chromosomes. Next, the junction sequences were compared to the corresponding "empty" chromosomal regions cloned from wild-type HeLa DNA. As shown in FIG. 7B, all of these insertions had occurred into TA target sites, which were subsequently duplicated to result in TA's flanking the integrated transposons. These data demonstrate that SB uses the same, cut-and-paste-type mechanism of transposition as other members of the Tc1/mariner superfamily and that fidelity of the reaction is maintained in heterologous cells. These data also suggest that the frequency of SB-mediated transposition is at least 15-fold higher than random recombination. Since none of the sequenced recombination events were mediated by SB-transposase, the real rate of transposition over random recombination could be many fold higher. If the integration is the result of random integration that was not mediated by the SB protein, the ends of the inserted neo construct would not correspond to the ends of the plasmids; there would have been either missing IR sequences and/or additional plasmid sequences that flank the transposon. Moreover, there would not have been duplicated TA basepairs at the sites of integration.

Taken together, the dependence of excision and integration, from extrachromosomal plasmids to the chromosomes of vertebrate cells, of a complete transposon with inverted repeats at both ends by a full-length transposase enzyme demonstrates that the gene transfer system is fully functional.

EXAMPLE 5

Transposition of DNA in Cells From Different Species

Host-requirements of transposase activity were assessed using three different vertebrate cells, LMTK from mouse and HeLa from human and embryonic cells from the zebrafish.

An assay was designed to demonstrate that the transposase worked in a functioning set of cells (i.e., embryonic cells that were differentiating and growing in a natural environment). The assay involved inter-plasmid transfer where the transposon in one plasmid is removed and inserted into a target plasmid and the transposase construct was injected into 1-cell stage zebra fish embryos. In these experiments the Indicator (donor) plasmids for monitoring transposon excision and/or integration included: 1) a marker gene that when recovered in *E. coli* or in fish cells, could be screened by virtue of either the loss or the gain of a function, and 2) transposase-recognition sequences in the IRs flanking the marker gene. The total size of the marked transposons was kept to about 1.6 kb, the natural size of the TcEs found in teleost genomes. However, the rate of gene transfer using transposons of about 5 kb is not significantly different from that for the 1.6 kb transposon, suggesting that transposition can occur with large transposons. The transposition activity of Ts1 transposase was evaluated by co-microinjecting 200 ng/μl of Ts1 mRNA, made in vitro by T7 RNA polymerase from a Bluescript expression vector, plus about 250 ng/μl each of target and donor plasmids into 1-cell stage zebrafish embryos. Low molecular weight DNA was prepared from the embryos at about 5 hrs post-injection, transformed into *E. coli* cells, and colonies selected by replica plating on agar containing 50 μg/ml kanamycin and/or ampicillin. In these studies there was a transposition frequency into the target plasmid was about 0.041% in experimental cells as compared to 0.002% in control cells. This level did not include transpositions that occurred in the zebrafish genome. In these experiments we found that about 40% to 50% of the embryos did not survive beyond 4 days. Insertional mutagenesis studies in the mouse have suggested that the rate of recessive lethality is about 0.05 (i.e., an average of about 20 insertions will be lethal). Assuming that this rate is applicable to zebrafish, the approximate level of mortality suggests that with the microinjection conditions used in these experiments, about 20 insertions per genome, the mortality can be accounted for.

EXAMPLE 6

Stable Gene Expression From SB Transposons

A transposon system will be functional for gene transfer, for such purposes as gene therapy and gene delivery to animal chromosomes for bioreactor systems, only if the delivered genes are reliably expressed. To determine the fidelity of gene expression following Sleeping Beauty transposase-mediated delivery, we co-microinjected a transposon containing the Green Fluorescent Protein (GFP) gene under the direction of an SV40 promoter plus in vitro-synthesized mRNA encoding Sleeping Beauty transposase into 1-cell zebrafish embryos. 34 of the injected embryos, that showed some expression of GFP during embryogenesis, were allowed to grow to maturity and were mated with wild-type zebrafish. From these matings we found that 4 of the 34 fish could transfer a GFP gene to their progeny (Table 1). The expression of GFP in the offspring of these four F0 fish, identified as A, B, C, and D, was evaluated and the fish were grown up. From the original four founders, the rate of transmission of the GFP gene ranged from about 2% to 12% (Table 1), with an average of about 7%. The expression of GFP in these fish was nearly the same in all individuals in the same tissue types, suggesting that expression of the GFP gene could be revived following transmission through eggs and sperm. These data suggest that the germ-lines were mosaic for expressing GFP genes and that the expression of the genes was stable. The F1 offspring of Fish D were mated with each other. In this case we would expect about 75% transmission and we found that indeed 69/90 (77%) F2 fish expressed the GFP protein at comparable levels in the same tissues; further testimony of the ability of the SB transposon system to deliver genes that can be reliably expressed through at least two generations of animal.

TABLE 1

Stability of gene expression in zebrafish following injection of a SB transposon containing the GFP gene.

| Transgenic | Expression of GFP | | |
|---|---|---|---|
| Line | F0 | F1 | F2 |
| 34 founders | 34 (of which 4 progeny, A–D, passed on the transgene) | | |
| A | | 25/200 (12%) | |
| B | | 76/863 (9%) | |
| C | | 12/701 (2%) | |
| D | | 86/946 (10%) | 69/90 (77%) |

The numbers in the columns for fish A–D show the numbers of GFP expressing fish followed by the total number of offspring examined. The percentages of GFP-expressing offspring are given in parentheses.

EXAMPLE 7

SB Transposons for Insertional Mutagenesis and Gene Discovery

Due to their inherent ability to move from one chromosomal location to another within and between genomes, transposable elements have revolutionized genetic manipulation of certain organisms including bacteria (Gonzales et al., 1996 *Vet. Microbiol.* 48, 283–291; Lee and Henk, 1996. *Vet. Microbiol.* 50, 143–148), Drosophila (Ballinger and Benzer, 1989 *Proc. Natl. Acad. Sci. USA* 86, 9402–9406; Bellen et al., 1989 *Genes Dev.* 3, 1288–1300; Spradling et al., 1995 *Proc. Natl. Acad. Sci. USA* 92, 10824–10830), *C. elegans* (Plasterk, 1995. *Meth. Cell. Biol.*, Academic Press, Inc. pp. 59–80) and a variety of plant species (Osborne and Baker, *Curr. Opin. Cell Biol*, 7, 406–413 (1995)). Transposons have been harnessed as useful vectors for transposon-tagging, enhancer trapping and transgenesis. However, the majority, if not all, animals of economic importance lack such a tool. For its simplicity and apparent ability to function in diverse organisms, SB should prove useful as an efficient vector for species in which DNA transposon technology is currently not available.

Figure 9:
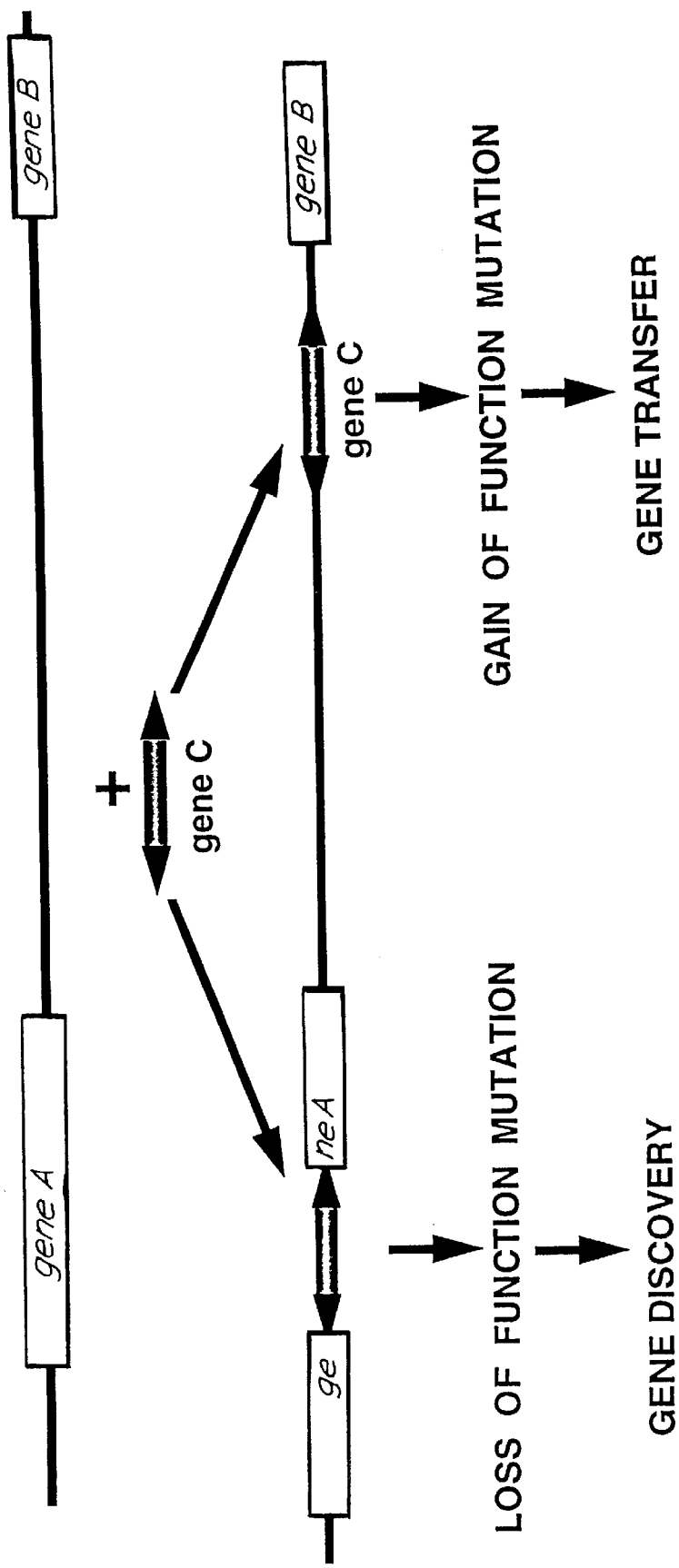
FIG. 9 illustrates two preferred methods for using the gene transfer system of this invention. Depending on the integration site of the nucleic acid fragment of this invention the effect can be either a loss-of-function or a gain-of-function mutation. Both types of activity can be exploited, for example, for gene discovery and/or functional genomics.

An SB-type transposable element can integrate into either of two types of chromatin, functional DNA sequences where it may have a deleterious effect due to insertional mutagenesis or non-functional chromatin where it may not have much of a consequence (FIG. 9). This power of "transposon tagging" has been exploited in simpler model systems for nearly two decades (Bingham et al., *Cell*, 25, 693–704 (1981); Bellen et al., 1989, supra). Transposon tagging is an old technique in which transgenic DNA is delivered to cells so that it will integrate into genes, thereby inactivating them by insertional mutagenesis. In the process, the inactivated genes are tagged by the transposable element which then can be used to recover the mutated allele. Insertion of a transposable element may disrupt the function of a gene which can lead to a characteristic phenotype. As illustrated in FIG. 10, because insertion is approximately random, the same procedures that generate insertional, loss-of-function mutants can often be used to deliver genes that will confer new phenotypes to cells. Gain-of-function mutants can be used to understand the roles that gene products play in growth and development as well as the importance of their regulation.

There are several ways of isolating the tagged gene. In all cases genomic DNA is isolated from cells from one or more tissues of the mutated animal by conventional techniques (which vary for different tissues and animals). The DNA is cleaved by a restriction endonuclease that may or may not cut in the transposon tag (more often than not it does cleave at a known site). The resulting fragments can then either be directly cloned into plasmids or phage vectors for identification using probes to the transposon DNA (see Kim et al., 1995 for references in *Mobile Genetic Elements*, IRL Press, D. L. Sheratt eds.). Alternatively, the DNA can be PCR amplified in any of many ways; we have used the LM-PCR procedure of Izsvak and Ivics (1993, supra) and a modification by Devon et al. (1995, supra) and identified by its hybridization to the transposon probe. An alternative method is inverse-PCR (e.g., Allende et al., *Genes Dev.*, 10, 3141–3155 (1996)). Regardless of method for cloning, the identified clone is then sequenced. The sequences that flank the transposon (or other inserted DNA) can be identified by their non-identity to the insertional element. The sequences can be combined and then used to search the nucleic acid databases for either homology with other previously characterized gene(s), or partial homology to a gene or sequence motif that encodes some function. In some cases the gene has no homology to any known protein. It becomes a new sequence to which others will be compared. The encoded protein will be the center of further investigation of its role in causing the phenotype that induced its recovery.

EXAMPLE 8

SB Transposons as Markers for Gene Mapping

Repetitive elements for mapping transgenes and other genetic loci have also been identified. DANA is a retroposon with an unusual substructure of distinct cassettes that appears to have been assembled by insertions of short sequences into a progenitor SINE element. DANA has been amplified in the Danio lineage to about $4\times10^5$ copies/genome. Angel elements, which are nearly as abundant as DANA, are inverted-repeat sequences that are found in the vicinity of fish genes. Both DANA and Angel elements appear to be randomly distributed in the genome, and segregate in a Medelian fashion. PCR amplifications using primers specific to DANA and Angel elements can be used as genetic markers for screening polymorphisms between fish stocks and localization of transgenic sequences. Interspersed repetitive sequence-PCR (IRS-PCR) can be used to detect polymorphic DNA. IRS-PCR amplifies genomic DNA flanked by repetitive elements, using repeat-specific primers to produce polymorphic fragments that are inherited in a Medelian fashion (FIG. 10A). Polymorphic DNA fragments can be generated by DANA or Angel specific primers in IRS-PCR and the number of detectable polymorphic bands can be significantly increased by the combination of various primers to repetitive sequences in the zebrafish genome, including SB-like transposons.

Polymorphic fragments can be recovered from gels and cloned to provide sequence tagged sites (STSs) for mapping mutations. FIG. 10B illustrates the general principles and constraints for using IRS-PCR to generate STSs. We estimate that about 0.1% of the zebrafish genome can be directly analyzed by IRS-PCR using only 4 primers. The four conserved (C1–4) regions of DANA seem to have different degrees of conservation and representation in the zebrafish genome and this is taken into account when designing PCR primers.

The same method has a potential application in fingerprinting fish stocks and other animal populations. The method can facilitate obtaining subclones of large DNAs cloned in yeast, bacterial and bacteriophage P1-derived artificial chromosomes (YACs, BACs and PACs respectively) and can be used for the detection of integrated transgenic sequences.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A nucleic acid fragment comprising:
   a nucleic acid sequence positioned between at least two inverted repeats that can bind to an SB protein, the inverted repeats comprising at least one direct repeat comprising a nucleic acid sequence selected from the group consisting of SEQ ID NO:6, SEQ ID NO:7, SEQ ID NO.8, SEQ ID NO:9, and SEQ ID NO:10;
   wherein the SB protein comprises an amino acid sequence having at least 80% identity to SEQ ID NO:1, binds to the inverted repeat sequence of at least one of SEQ ID NO:4 and SEQ ID NO:5, and catalyzes the integration of the nucleic acid fragment into DNA in an isolated or cultured vertebrate cell.

2. The fragment of claim 1 wherein the nucleic acid fragment is part of a plasmid.

3. The fragment of claim 1 wherein the nucleic acid sequence comprises at least a portion of an open reading frame.

4. The fragment of claim 1 wherein the nucleic acid sequence comprises at least one expression control region.

5. The fragment of claim 4 wherein the expression control region is selected from the group consisting of a promoter, an enhancer or a silencer.

6. The fragment of claim 1 wherein the nucleic acid sequence comprises a promoter operably linked to at least a portion of an open reading frame.

7. The fragment of claim 1 wherein the vertebrate cell is fish cell.

8. The fragment of claim 1 wherein the vertebrate cell is a mammalian cell.

9. The fragment of claim 8 wherein the vertebrate cell is a mouse cell or a human cell.

10. The fragment of claim 1 wherein the DNA into which the fragment is capable of integrating is the cell genome or extrachromosomal DNA.

11. The fragment of claim 10 wherein the extrachromosomal DNA is selected from the group consisting of an episome and a plasmid.

12. The nucleic acid fragment of claim 1 wherein at least one of the inverted repeats comprises SEQ ID NO:4 or SEQ ID NO:5.

13. The nucleic acid fragment of claim 1 wherein the inverted repeats can bind to an SB protein comprising the amino acid sequence of SEQ ID NO:1.

14. A gene transfer system to introduce DNA into the DNA of an isolated or cultured vertebrate cell comprising:
 a transposase or a nucleic acid encoding a transposase, wherein the transposase is an SB protein; and
 a nucleic acid fragment comprising a nucleic acid sequence positioned between at least two inverted repeats that can bind to the SB protein, the inverted repeats comprising at least one direct repeat comprising a nucleic acid sequence selected from the group consisting of SEQ ID NO:6, SEQ ID NO:7, SEQ ID NO. 8, SEQ ID NO:9, and SEQ ID NO:10;
 wherein the SB protein comprises amino acid sequence having at least 80% identity to SEQ ID NO:1, binds to the inverted repeat sequence of at least one of SEQ ID NO:4 and SEQ ID NO:5, and catalyzes the integration of the nucleic acid fragment into DNA in the vertebrate cell.

15. The gene transfer system of claim 14 wherein the SB protein comprises SEQ ID NO:1.

16. The gene transfer system of claim 14 wherein the transposase is provided to the cell as a protein.

17. The gene transfer system of claim 14 wherein the transposase is provided to the cell as nucleic acid encoding a transposase.

18. The gene transfer system of claim 17 wherein the nucleic acid encoding a transposase is RNA.

19. The gene transfer system of claim 14 wherein the nucleic acid encoding the transposase is integrated into the genome of the cell.

20. The gene transfer system of claim 14 wherein the nucleic acid fragment is part of a plasmid or a recombinant viral vector.

21. The gene transfer system of claim 14 wherein the nucleic acid sequence comprises at least a portion of an open reading frame.

22. The gene transfer system of claim 14 wherein the nucleic acid sequence comprises at least a regulatory region of a gene.

23. The gene transfer system of claim 22 wherein the regulatory region is a transcriptional regulatory region.

24. The gene transfer system of claim 22 wherein the regulatory region is selected from the group consisting of a promoter, an enhancer, a silencer, a locus-control region, and a border element.

25. The gene transfer system of claim 14 wherein the nucleic acid sequence comprises a promoter operably linked to at least a portion of an open reading frame.

26. The gene transfer system of claim 14 wherein the vertebrate cell is a fish cell.

27. The gene transfer system of claim 14 wherein the vertebrate cell is a mammalian cell.

28. The gene transfer system of claim 27 wherein the mammalian cell is a mouse cell or a human cell.

29. The gene transfer system of claim 14 wherein the DNA of a cell is the cell genome or extrachromosomal DNA.

30. The gene transfer system of claim 29 wherein the extrachromosomal DNA is selected from the group consisting of an episome and a plasmid.

31. The gene transfer system of claim 14 wherein at least one of the inverted repeats comprises SEQ ID NO:4 or SEQ ID NO:5.

32. The gene transfer system of claim 14 wherein the nucleic acid sequence is obtained from a library of recombinant sequences.

33. The gene transfer system of claim 14 wherein the nucleic acid sequence is introduced into the cell using a method selected from the group consisting of:
 particle bombardment;
 electroporation;
 microinjection;
 combining the nucleic acid fragment with lipid-containing vesicles or DNA condensing reagents; and
 incorporating the nucleic acid fragment into a viral vector and contacting the viral vector with the cell.

34. A nucleic acid encoding an SB protein, wherein the SB protein comprises an amino acid sequence having at least 80% identity to SEQ ID NO:1, binds to the inverted repeat sequence of at least one of SEQ ID NO:4 and SEQ ID NO:5, and catalyzes the integration of nucleic acid into DNA in an isolated or cultured vertebrate cell.

35. A nucleic acid vector comprising the nucleic acid of claim 34.

36. The nucleic acid vector of claim 35 which is a gene expression vector.

37. The nucleic acid vector of claim 36 which is a plasmid.

38. The nucleic acid of claim 34 wherein the nucleic acid is a linear nucleic acid fragment.

39. An isolated or cultured vertebrate cell comprising the nucleic acid of claim 34.

40. The isolated or cultured vertebrate cell of claim 39 which is a fish cell.

41. The isolated or cultured vertebrate cell of claim 39 which is a mammalian cell.

42. An isolated or cultured vertebrate cell comprising the nucleic acid of claim 34, wherein the nucleic acid is integrated into the genome of the cell.

43. An SB protein comprising the amino acid sequence of SEQ ID NO:1.

44. A method for introducing nucleic acid into DNA in an isolated or cultured vertebrate cell comprising the step of:
 introducing into the cell a nucleic acid fragment comprising a nucleic acid sequence positioned between at least two inverted repeats that can bind to an SB protein, the inverted repeats comprising at least one direct repeat comprising a nucleic acid sequence selected from the group consisting of SEQ ID NO:6, SEQ ID NO:7, SEQ ID NO. 8, SEQ ID NO:9, and SEQ ID NO:10; wherein the SB protein comprises an amino acid sequence having at least 80% identity to SEQ ID NO:1, binds to the inverted repeat sequence of at least one of SEQ ID NO:4 and SEQ ID NO:5, and catalyzes the integration of the nucleic acid fragment into DNA in the cell.

45. The method of claim 44 further comprising introducing the SB protein into the cell.

46. The method of claim 45 wherein the SB protein is introduced to the cell as RNA.

47. The method of claim 44 wherein the cell comprises nucleic acid encoding the SB protein.

48. The method of claim 47 wherein the nucleic acid encoding the SB protein is integrated into the cell genome.

49. The method of claim 47 wherein the SB protein is stably expressed in the cell.

50. The method of claim 47 wherein the SB protein is under the control of an inducible promoter.

51. The method of claim 44 wherein introducing the nucleic acid fragment into the cell comprises using a method selected from the group consisting of:
   microinjection;
   electroporation;
   combining the nucleic acid fragment with cationic lipid vesicles or DNA condensing reagents; and
   incorporating the nucleic acid fragment into a viral vector and contacting the viral vector with the cell.

52. The method of claim 51 wherein the viral vector is selected from the group consisting of a retroviral vector, an adenovirus vector or an adeno-associated viral vector.

53. The method of claim 44 further comprising introducing a DNA or an RNA encoding the SB protein into the cell.

54. The method of claim 44 wherein the nucleic acid sequence encodes a protein.

55. An isolated or cultured vertebrate cell producing the protein of claim 54.

56. The method of claim 44 wherein the protein is a marker protein.

57. The method of claim 44 wherein the inverted repeats can bind to an SB protein comprising the amino acid sequence of SEQ ID NO:1.

58. A protein comprising an amino acid sequence having at least 80% identity to SEQ ID NO:1, wherein the protein binds to the inverted repeat sequence of at least one of SEQ ID NO:4 and SEQ ID NO:5 and catalyzes the integration of nucleic acid into DNA of a vertebrate cell.

59. A protein with transposase activity and comprising an amino acid sequence having at least 80% identity to SEQ ID NO:1, wherein the protein binds to at least one nucleic acid sequence selected from the group consisting of SEQ ID NO:4, SEQ ID NO:5, SEQ ID NO:6, SEQ ID NO:7, SEQ ID NO:8, SEQ ID NO:9 and SEQ ID NO:10.

60. A nucleic acid encoding an SB protein comprising the amino acid sequence of SEQ ID NO:1.

61. The nucleic acid of claim 60 selected from the group consisting of RNA and DNA.

62. A composition comprising a vertebrate cell comprising a nucleic acid encoding an SB protein, wherein the SB protein comprises an amino acid sequence having at least 80% identity to SEQ ID NO:1, binds to the inverted repeat sequence of at least one of SEQ ID NO:4 and SEQ ID NO:5, and catalyzes the integration of nucleic acid into DNA in the vertebrate cell.

63. The composition of claim 62 wherein the nucleic acid is integrated into the genome of the vertebrate cell.

64. A composition comprising a vertebrate cell comprising an SB protein comprising an amino acid sequence having at least 80% identity to SEQ ID NO:1, wherein the SB protein binds to the inverted repeat sequence of at least one of SEQ ID NO:4 and SEQ ID NO:5 and catalyzes the integration of nucleic acid into DNA in the vertebrate cell.

* * * * *

UNITED STATES PATENT AND TRADEMARK OFFICE
CERTIFICATE OF CORRECTION

PATENT NO. : 6,489,458 B2
DATED : December 3, 2002
INVENTOR(S) : Hackett et al.

It is certified that error appears in the above-identified patent and that said Letters Patent is hereby corrected as shown below:

Title page,
Item [56], References Cited, U.S. PATENT DOCUMENTS, insert
-- 5,928,888   7/1999  Whitney --;
FOREIGN PATENT DOCUMENTS, insert -- WO  WO 98/40510  9/1998 --;
OTHER PUBLICATIONS, before "*cited by examiner ", insert
-- Bonaldo et al., "Efficient Gene Trap Screening for Novel Developmental Genes Using IRESβgeo Vector and *in Vitro* Preselection," *Experimental Cell Research*, 244:125-136 (1998).
Ebert et al., "A Moloney MLV-Rat Somatotropin Fusion Gene Produces Biologically Active Somatrotropin in a Transgenic Pig," *Mol. Endo.*, 2(3);277-283 (1988).
Hammer et al., "Genetic Engineering of Mammalian Embryos," *J. Anim. Sci.*, 63:269-278 (1986).
Koster et al., "Comparison of Monocistronic and Bicistronic Constructs for Neutrophin Transgene and Reporter Gene Expression in Fish Cells," *Mol. Mar. Biol. Biotech.*, 5(1):1-8 (1996).
Mullins et al., "Perspectives Series: Molecular Medicine in Genetically Engineered Animals -- Transgenesis in the Rat and Larger Mammals," *J. Clin. Invest.*, 97(7):1557-1560 (1996). --.

Column 1,
Line 15, delete "R01-RR0625" and replace with -- R01-RR06625 --.
Line 16, delete "o101-04" and replace with -- 0101-04 --.

Column 12,
Line 50, before "One", insert an indentation to denote a new paragraph.

Column 37,
At the sequence for SEQ ID NO:6, delete "GTTCAAGTCG GAAGTTTACA TACACTTAG" and replace with
-- 5'-GTTGAAGTCGGAAGTTTACATACACTTAAG-3' --.

Column 39,
At the sequence for SEQ ID NO:9, delete "AGTTGAATCG GAAGTTTACA TACACCTTAG", and replace with
-- 5'-AGTTGAAGTCGGAAGTTTACATACACCTTAG-3' --.

UNITED STATES PATENT AND TRADEMARK OFFICE
CERTIFICATE OF CORRECTION

PATENT NO. : 6,489,458 B2
DATED : December 3, 2002
INVENTOR(S) : Hackett et al.

It is certified that error appears in the above-identified patent and that said Letters Patent is hereby corrected as shown below:

<u>Column 61</u>,
Line 10, after "cell is", insert -- a --.

Signed and Sealed this

Ninth Day of March, 2004

JON W. DUDAS
*Acting Director of the United States Patent and Trademark Office*

SEQUENCE LISTING (1) GENERAL INFORMATION:

(iii) NUMBER OF SEQUENCES: 63

(2) INFORMATION FOR SEQ ID NO:1:

(i) SEQUENCE CHARACTERISTICS:
      (A) LENGTH: 340 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met Gly Lys Ser Lys Glu Ile Ser Gln Asp Leu Arg Lys Lys Ile Val
1               5                   10                  15

Asp Leu His Lys Ser Gly Ser Ser Leu Gly Ala Ile Ser Lys Arg Leu
                20                  25                  30

Lys Val Pro Arg Ser Ser Val Gln Thr Ile Val Arg Lys Tyr Lys His
                35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
                100                 105                 110

Lys Gly Arg Ser Ala Arg Lys Lys Pro Leu Leu Gln Asn Arg His Lys
            115                 120                 125

Lys Ala Arg Leu Arg Phe Ala Thr Ala His Gly Asp Lys Asp Arg Thr
        130                 135                 140

Phe Trp Arg Asn Val Leu Trp Ser Asp Glu Thr Lys Ile Glu Leu Phe
```

```
145                 150                 155                 160
Gly His Asn Asp His Arg Tyr Val Trp Arg Lys Lys Gly Glu Ala Cys
                165                 170                 175
Lys Pro Lys Asn Thr Ile Pro Thr Val Lys His Gly Gly Ser Ile
            180                 185                 190
Met Leu Trp Gly Cys Phe Ala Ala Gly Gly Thr Gly Ala Leu His Lys
            195                 200                 205
Ile Asp Gly Ile Met Arg Lys Glu Asn Tyr Val Asp Ile Leu Lys Gln
    210                 215                 220
His Leu Lys Thr Ser Val Arg Lys Leu Lys Leu Gly Arg Lys Trp Val
225                 230                 235                 240
Phe Gln Met Asp Asn Asp Pro Lys His Thr Ser Lys Val Val Ala Lys
                245                 250                 255
Trp Leu Lys Asp Asn Lys Val Lys Val Leu Glu Trp Pro Ser Gln Ser
            260                 265                 270
Pro Asp Leu Asn Pro Ile Glu Asn Leu Trp Ala Glu Leu Lys Lys Arg
        275                 280                 285
Val Arg Ala Arg Arg Pro Thr Asn Leu Thr Gln Leu His Gln Leu Cys
290                 295                 300
Gln Glu Glu Trp Ala Lys Ile His Pro Thr Tyr Cys Gly Lys Leu Val
305                 310                 315                 320
Glu Gly Tyr Pro Lys Arg Leu Thr Gln Val Lys Gln Phe Lys Gly Asn
                325                 330                 335
Ala Thr Lys Tyr
        340

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TGTTTATTGC GGCACTATTC                                            20

(2) INFORMATION FOR SEQ ID NO:3:

(i) SEQUENCE CHARACTERISTICS:
        (A) LENGTH: 1023 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

ATGGGAAAAT CAAAAGAAAT CAGCCAAGAC CTCAGAAAAA AAATTGTAGA CCTCCACAAG     60

TCTGGTTCAT CCTTGGGAGC AATTTCCAAA CGCCTGAAAG TACCACGTTC ATCTGTACAA    120

ACAATAGTAC GCAAGTATAA ACACCATGGG ACCACGCAGC CGTCATACCG CTCAGGAAGG    180

AGACGCGTTC TGTCTCCTAG AGATGAACGT ACTTTGGTGC GAAAAGTGCA AATCAATCCC    240

AGAACAACAG CAAAGGACCT TGTGAAGATG CTGGAGGAAA CAGGTACAAA AGTATCTATA    300

TCCACAGTAA AACGAGTCCT ATATCGACAT AACCTGAAAG GCCGCTCAGC AAGGAAGAAG    360

CCACTGCTCC AAAACCGACA TAAGAAAGCC AGACTACGGT TTGCAACTGC ACATGGGGAC    420
```

```
AAAGATCGTA CTTTTTGGAG AAATGTCCTC TGGTCTGATG AAACAAAAAT AGAACTGTTT      480

GGCCATAATG ACCATCGTTA TGTTTGGAGG AAGAAGGGGG AGGCTTGCAA GCCGAAGAAC      540

ACCATCCCAA CCGTGAAGCA CGGGGGTGGC AGCATCATGT TGTGGGGGTG CTTTGCTGCA      600

GGAGGGACTG GTGCACTTCA CAAAATAGAT GGCATCATGA GGAAGGAAAA TTATGTGGAT      660

ATATTGAAGC AACATCTCAA GACATCAGTC AGGAAGTTAA AGCTTGGTCG CAAATGGGTC      720

TTCCAAATGG ACAATGACCC CAAGCATACT TCCAAAGTTG TGGCAAAATG GCTTAAGGAC      780

AACAAAGTCA AGGTATTGGA GTGGCCATCA CAAAGCCCTG ACCTCAATCC TATAGAAAAT      840

TTGTGGGCAG AACTGAAAAA GCGTGTGCGA GCAAGGAGGC CTACAAACCT GACTCAGTTA      900

CACCAGCTCT GTCAGGAGGA ATGGGCCAAA ATTCACCCAA CTTATTGTGG GAAGCTTGTG      960

GAAGGCTACC CGAAACGTTT GACCCAAGTT AAACAATTTA AAGGCAATGC TACCAAATAC     1020

TAG                                                                  1023

(2) INFORMATION FOR SEQ ID NO:4:

(i) SEQUENCE CHARACTERISTICS:
        (A) LENGTH: 226 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGTTGAAGTC GGAAGTTTAC ATACACTTAA GTTGGAGTCA TTAAAACTCG TTTTTCAACT       60

ACACCACAAA TTTCTTGTTA ACAAACAATA GTTTTGGCAA GTCAGTTAGG ACATCTACTT      120

TGTGCATGAC ACAAGTCATT TTTCCAACAA TTGTTTACAG ACAGATTATT TCACTTATAA      180

TTCACTGTAT CACAATTCCA GTGGGTCAGA AGTTTACATA CACTAA                    226

(2) INFORMATION FOR SEQ ID NO:5:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TTGAGTGTAT GTTAACTTCT GACCCACTGG AATGTGATG AAAGAAATAA AAGCTGAAAT        60

GAATCATTCT CTCTACTATT ATTCTGATAT TTCACATTCT TAAAATAAAG TGGTGATCCT      120

AACTGACCTT AAGACAGGGA ATCTTTACTC GGATTAAATG TCAGGAATTG TGAAAAAGTG      180

AGTTTAAATG TATTTGGCTA AGGTGTATGT AAACTTCCGA CTTCAACTG                  229

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTTCAAGTCG GAAGTTTACA TACACTTAG                                        29
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CAGTGGGTCA GAAGTTTACA TACACTAAGG                                    30
```

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CAGTGGGTCA GAAGTTAACA TACACTCAAT T                                  31
```

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
AGTTGAATCG GAAGTTTACA TACACCTTAG                                    30
```

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
CAKTGRGTCR GAAGTTTACA TACACTTAAG                                    30
```

(2) INFORMATION FOR SEQ ID NO:11:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
ACATACAC                                                             8
```

(2) INFORMATION FOR SEQ ID NO:12:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:12:

TTTCAGTTTT GGGTGAACTA TCC                            23

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGCGACRCAG TGGCGCAGTR GG                             22

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GAAYRTGCAA ACTCCACACA GA                             22

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TCCATCAGAC CACAGGACAT                                20

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TGTCAGGAGG AATGGGCCAA AATTC                          25

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:17:

CCTCTAGGAT CCGACATCAT G                                         21

(2) INFORMATION FOR SEQ ID NO:18:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TCTAGAATTC TAGTATTTGG TAGCATTG                                  28

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AACACCATGG GACCACGCAG CCGTCA                                    26

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

CAGGTTATGT CGATATAGGA CTCGTTTTAC                                30

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CCTTGCTGAG CGGCCTTTCA GGTTATGTCG                                30

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TTGCACTTTT CGCACCAA                                                    18

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GTACCTGTTT CCTCCAGCAT C                                                21

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GAGCAGTGGC TTCTTCCT                                                    18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

CCACAACATG ATGCTGCC                                                    18

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TGGCCACTCC AATACCTTGA C                                                21

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

ACACTCTAGA CTAGTATTTG GTAGCATTGC C                                     31

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GTGCTTCACG GTTGGGATGG TG                      22

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

ATTTTCTATA GGATTGAGGT CAGGGC                  26

(2) INFORMATION FOR SEQ ID NO:30:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GTCTGGTTCA TCCTTGGGAG CAATTTCCAA ACGCC         35

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CAAAACCGAC ATAAGAAAGC CAGACTACGG              30

(2) INFORMATION FOR SEQ ID NO:32:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

ACCATCGTTA TGTTTGGAGG AAGAAGGGGG AGGCTTGCAA GCCG    44

(2) INFORMATION FOR SEQ ID NO:33:

(i) SEQUENCE CHARACTERISTICS:

(A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGCATCATGA GGAAGGAAAA TTATGTGGAT ATATTG                            36

(2) INFORMATION FOR SEQ ID NO:34:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CTGAAAAAGC GTGTGCGAGC AAGGAGGCC                                    29

(2) INFORMATION FOR SEQ ID NO:35:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GTGGAAGGCT ACCCGAAACG TTTGACC                                      27

(2) INFORMATION FOR SEQ ID NO:36:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GACAAAGATC GTACTTTTTG GAGAAATGTC                                   30

(2) INFORMATION FOR SEQ ID NO:37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

GTTGAAGTCG GAAGTTTACA TACACTTAGG                                   30

(2) INFORMATION FOR SEQ ID NO:38:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

GTTTAAACCA GAAGTTTACA CACACTGTAT                                                30

(2) INFORMATION FOR SEQ ID NO:39:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:39:

CCAGTGGGTC AGAAGTTTAC ATACACTAAG                                                30

(2) INFORMATION FOR SEQ ID NO:40:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:40:

CTTGAAAGTC AAGTTTACAT ACAATAAG                                                  28

(2) INFORMATION FOR SEQ ID NO:41:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:41:

TCCAGTGGGT CAGAAGTTTA CATACACTAA GT                                             32

(2) INFORMATION FOR SEQ ID NO:42:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:42:

TCCAGTGGGT CAGAAGTTTA CATACACTAA GT                                             32

(2) INFORMATION FOR SEQ ID NO:43:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:43:

```
TGAATTCGAG CTCGGTACCC TACAGT                                              26

(2) INFORMATION FOR SEQ ID NO:44:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

ACTGTAGGGG ATCCTCTAGA GTCGAC                                              26

(2) INFORMATION FOR SEQ ID NO:45:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

AAATTTATTT AATGTGTACA TACAGT                                              26

(2) INFORMATION FOR SEQ ID NO:46:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

ACTGTATAAG AACCTTTAGA ACGAAG                                              26

(2) INFORMATION FOR SEQ ID NO:47:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

AAATTTATTT AATGTGTACA TA                                                  22

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

TAAGAACCTT TAGAACGAAG                                                     20
```

(2) INFORMATION FOR SEQ ID NO:49:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

GAATAAACAG TAGTTCAACT TACAGT                                      26

(2) INFORMATION FOR SEQ ID NO:50:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

ACTGTATATG TTTTCATGGA AAATAG                                      26

(2) INFORMATION FOR SEQ ID NO:51:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GAATAAACAG TAGTTCAACT TA                                          22

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

TATGTTTTCA TGGAAAATAG                                              20

(2) INFORMATION FOR SEQ ID NO:53:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

TCACTGACTC ATTCAACATC TACAGT                                      26

(2) INFORMATION FOR SEQ ID NO:54:

(i) SEQUENCE CHARACTERISTICS:
        (A) LENGTH: 26 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

ACTGTATTTA TTGAATGCCT GCTGAA                                        26

(2) INFORMATION FOR SEQ ID NO:55:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

TCACTGACTC ATTCAACATC TA                                            22

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

TTTATTGAAT GCCTGCTGAA                                               20

(2) INFORMATION FOR SEQ ID NO:57:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

ACTTACATAA TTATAAGTTT TACAGT                                        26

(2) INFORMATION FOR SEQ ID NO:58:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

ACTGTATATA ATGATGACAT CTATTA                                        26

(2) INFORMATION FOR SEQ ID NO:59:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:59:

ACTTACATAA TTATAAGTTT TA                                    22

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

TATAATGATG ACATCTATTA                                       20

(2) INFORMATION FOR SEQ ID NO:61:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

TATAAAGACA CATTCACATG TACAGT                                26

(2) INFORMATION FOR SEQ ID NO:62:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

ACTGTATGTT TACTGCGGCA CTATTC                                26

(2) INFORMATION FOR SEQ ID NO:63:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

TATAAAGACA CATGCACACG TA                                    22